US007838629B2

(12) United States Patent
Fiedler et al.

(10) Patent No.: US 7,838,629 B2
(45) Date of Patent: Nov. 23, 2010

(54) UBIQUITIN OR GAMMA-CRYSTALLINE CONJUGATES FOR USE IN THERAPY, DIAGNOSIS AND CHROMATOGRAPHY

(75) Inventors: Erik Fiedler, Halle/Saale (DE); Hilmar Ebersbach, Wallisellen (CH); Thomas Hey, Halle/Saale (DE); Ulrike Fiedler, Halle/Saale (DE)

(73) Assignee: Scil Proteins GmbH, Halle/Saale (DE)

( * ) Notice: Subject to any disclaimer, the term of this patent is extended or adjusted under 35 U.S.C. 154(b) by 382 days.

(21) Appl. No.: 11/732,632

(22) Filed: Apr. 4, 2007

(65) Prior Publication Data

US 2007/0248536 A1 Oct. 25, 2007

Related U.S. Application Data

(63) Continuation of application No. PCT/EP2005/010932, filed on Oct. 11, 2005.

(30) Foreign Application Priority Data

Oct. 11, 2004 (DE) .................. 10 2004 049 479

(51) Int. Cl.
*C07K 14/00* (2006.01)
(52) U.S. Cl. ...................................... 530/350
(58) Field of Classification Search ............ None
See application file for complete search history.

(56) References Cited

U.S. PATENT DOCUMENTS

| 4,873,192 | A  | 10/1989 | Kunkel |
| 5,789,166 | A  | 8/1998  | Bauer et al. |
| 5,958,684 | A  | 9/1999  | Van Leeuwen et al. |
| 6,673,901 | B2 | 1/2004  | Koide |
| 7,601,803 | B1 | 10/2009 | Fiedler et al. |
| 2004/0043386 | A1 | 3/2004 | Pray et al. |
| 2006/0058510 | A1 | 3/2006 | Skerra et al. |
| 2006/0099686 | A1 | 5/2006 | Fiedler et al. |
| 2007/0111287 | A1 | 5/2007 | Fiedler et al. |
| 2008/0171851 | A1 | 7/2008 | Fiedler et al. |

FOREIGN PATENT DOCUMENTS

| FR | 2 761 688 A | 10/1998 |
| WO | WO 97/16556 | 5/1997 |
| WO | WO 98/44121 | 10/1998 |
| WO | WO 98/54312 | 12/1998 |
| WO | WO 99/16873 | 4/1999 |
| WO | WO 01/04144 A | 1/2001 |
| WO | WO2004/106368 | 12/2004 |
| WO | WO2006/040129 | 4/2006 |

OTHER PUBLICATIONS

Baker et al. Journal of Biological Chemistry, 1994, 269(41):25381-25386.*

Ubiquitin-like Superfamily Statistics from <http://supfam.cs.bris.ac.uk/SUPERFAMILY/cgi-bin/scop.cgi?sunid=54236> obtained on Mar. 16, 2010—from Superfamily v. 1.73—HMM library and genome assignments server.*
International Search Report corresponding to PCT Application No. PCT/EP2005/010932 dated Nov. 4, 2006.
Yeh et al. *Ubiquitin-like proteins: new wines in new bottles. Gene*, vol. 248, (2000), pp. 1-14.
Notification of Transmittal of Translation of the International Preliminary Report on Patentability (Chapter I or Chapter II of the Patent Cooperation Treaty) corresponding to International Application No. PCT/EP2005/010932 dated May 3, 2007.
Abedi et al, "Green fluorescent protein as a scaffold for intracellular presentation of peptides," Nucleic Acids Research, vol. 26, No. 2 pp. 623-630 (1998).
Advisory Action corresponding to U.S. Appl. No. 10/030,605 dated Oct. 13, 2006.
Advisory Action corresponding to U.S. Appl. No. 12/072,959 dated May 18, 2010.
Bazarsuren et al., "In vitro folding, functional characterization, and disulfide pattern of the extracellular domain of human GLP-1 receptor," Biophysical Chemistry. vol. 96 pp. 305-318 (2002).
Beal et al., "Surface hydrophobic residues of multiubiquitin chains essential for proteolytic targeting," PNAS. vol. 93 pp. 861-866 (1996).
Berman et al., "The Protein Data Bank," Nucleic Acid Res. vol. 28, No. 1 pp. 235-242 (2000).
Beste, et al., "Small antibody-like proteins with prescribed ligand specificities derived from the lipocalin fold," PNAS. vol. 96 pp. 1898-1903 (1999).
Bird et al., "Single-Chain Antigen-Binding Proteins," Science. vol. 242 pp. 423-426 (1988).
Bowie et al., "Deciphering the Message in Protein Sequences: Tolerance to Amino Acid Substitutions," Science. vol. 247 pp. 1306-1310 (1990).
Brinkmann et al., "A recombinant immunotoxin containing a disulfide-stabilized Fv-fragment," PNAS. vol. 90 pp. 7538-7542 (1993).
Brinkmann et al., "Stabilization of a Recombinant Fv Fragment by Base-Loop Interconnection and $V_h$-$V_L$ Permutation," Journal of Molecular Biology. vol. 268 pp. 107-117 (1997).
Buchberger et al., "The UBX Domain: A Widespread Ubiquitin-Like Module," Journal of Molecular Biology. vol. 307, No. 1 pp. 17-24 (2001).
Burch, T.J., and Haas, A.L., "Site-directed mutagenesis of ubiquitin, Differential roles for arginine in the interaction with ubiquitin-activating enzyme," Biochemistry. vol. 33, No. 23 pp. 7300-7308 (1994) [Abstract].
Butt et al., "Ubiquitin fusion augments the yield of cloned gene products in *Escherichia coli*," PNAS. vol. 86 pp. 2540-2544 (1989).

(Continued)

*Primary Examiner*—Suzanne M. Noakes
(74) *Attorney, Agent, or Firm*—Jenkins, Wilson, Taylor & Hunt, P.A.

(57) ABSTRACT

The present invention relates to conjugates containing a covalent linkage between one or more polypeptide molecules based on gamma-crystallin or ubiquitin and one or more functional components. Furthermore, the present invention relates to a method for the preparation of such a conjugate as well as to the use of the conjugate in diagnostics, therapy and chromatography.

34 Claims, 11 Drawing Sheets

OTHER PUBLICATIONS

Campion et al., "Biochemical Properties of Site-Directed Mutants of Human Epidermal Growth Factor: Importance of Solvent-Exposed Hydrophobic Residues of the Amino-Terminal Domain in Receptor Binding," Biochemistry. vol. 29, No. 42 pp. 9988-9993 (1990).

Carter et al., "High level *Escherichia coil* expression and production of a bivalent humanized antibody fragment," Nature Biotechnology. vol. 10 pp. 163-167 (1992).

Chen et al., "Direct Interaction of Hepatitis C Virus Core Protein with the Cellular Lymphotoxin-β Receptor Modulates the Signal Pathway of the Lymphotoxin-β Receptor," Journal of Virology. vol. 71, No. 12 pp. 9417-9426 (1997).

Chirgadze et al., "Structure fo the Bovine Eye Lens γD (γIIIb)-Crystallin at 1.95 Å," Acta Cryst. vol. D52 pp. 712-721 (1996).

Choo, Y., and Klug, A., "Designing DNA-binding proteins on the surface of filamentous phage," Current Opinion in Biotechnology. vol. 6 pp. 431-436 (1995).

Colcher et al., "Pharmacokinetics and biodistribution of genetically-engineered antibodies," Q.J. Nucl. Med. vol. 42 pp. 225-241 (1998).

Connolly, "Solvent-Accessible Surfaces of Proteins and Nucleic Acids." Science. vol. 221, No. 4612 pp. 709-713 (1983).

Cortese et al., "Selection of biologically active peptides by phage display of random peptide libraries," Current Opinion in Biotechnology. vol. 7 pp. 616-621 (1996).

Crameri et al., "Molecular evolution of an arsenate detoxification pathway by DNA shuffling," Nature Biotechnology. vol. 5 pp. 436-438 (1997).

Cumber et al., "Comparative stabilities in vitro and in vivo of a recombinant mouse antibody FvCys fragment and a bisFvCys conjugate," Journal of Immunology. vol. 149, No. 1 pp. 120-126 (1992).

Daugherty et al., "Antibody affinity maturation using bacterial surface display," Protein Engineering. vol. 11, No. 9 pp. 825-832 (1998).

de Kruif et al., "Selection and Application of Human Single Chain Fv Antibody Fragments from a Semi-synthetic Phage Antibody Display Library with Designed CDR3 Regions," Journal of Molecular Biology. vol. 248 pp. 97-105 (1995).

den Dunnen et al., Database PIR_79, Accession No. A24060; Gene. vol. 38 pp. 197-204 (1985).

den Dunnen et al., Database PIR_79, Accession No. B24060; J. Mol. Biol. vol. 189 pp. 37-46 (1986).

Ebersbach et al., "Affilin-Novel Binding Molecules Based on Human γ-B-Crystallin, an All 62 -Sheet Protein," Journal of Molecular Biology. Vol. 372 pp. 172-185 (2007).

Ecker et al., "Gene Synthesis, Expression, Structures, and Functional Activities of Site-specific Mutants of Ubiquitin," The Journal of Biological Chemistry, vol. 262, No. 29 pp. 14213-14221 (1987).

European Office Action corresponding to European Patent Application No. 00 944 034.8-2401 dated Oct. 7, 2004.

European Patent Office Examination Report corresponding to Euopean Patent Application No. 06118519.5-2401 dated Apr. 2, 2007.

Exley, D., and Woodhams, B., "The Specificity of Antisera Raised by Oestradiol-17β-3-Hemisuccinyl-Bovine Serum Albumin," Steroids. vol. 27, No. 6 pp. 813-820 (1976).

Filippi et al., "Linkage and Sequence Conservation of the X-Linked Genes DX253E (P3) and DXS254E (GdX) in Mouse and Man," Genomics. vol. 7 pp. 453-457 (1990).

Finucane, F.D., and Woolfson, D.N., "Core-Directed Protein Design. II. Rescue of a Multiply Mutated and Destabilized Variant of Ubiquitin." Biochemistry. vol. 38, No. 36 pp. 11613-11623 (1999).

"Fold: beta-Grasp (ubiquitin-like)," http://scop.mrc-lmb.cam.ac.uk/scop/data/scop.b.e.ca.html, Mar. 15, 2004. [Abstract].

Folgori et al., "Vaccine-Induced T-Cell Responses Against HCV: One Step Taken, More to Follow," Gastroenterology. vol. 132, No. 4 pp. 1626-1628.

Genbank Accession No. IUBQ. Schlesinger,D.H. and Goldstein,G., "Hybrid troponin reconstituted from vertebrate and arthropod subunits," Nature. vol. 255, No. 5507 pp. 423-424 (1975).

Genbank Accession No. D10934. Wang et al., "Prevalence, genotypes, and an isolate (HC-C2) of hepatitis C virus in Chinese patients with liver disease," J. Med. Virology. vol. 40, No. 3 pp. 254-260 (1993).

Genbank Accession No. M16894. Hay et al., "cDNA clones encoding bovine gamma-crystallins," Biochem. Biophys. Res. Comm. vol. 146, No. 1 pp. 332-338 (1987).

Genbank Accession No. P07316. den Dunnen et al., "Two human gamma-crystallin genes are linked and riddle with Alu-repeats," Gene. vol. 38, Nos. 1-3 pp. 197-204 (1985).

German Examination Report dated Mar. 15, 2004.

Glockshuber et al., "A Comparision of Strategies to Sabilize Immunoglobulin Fv-Fragments," Biochemistry. vol. 29 pp. 1362-1367 (1990).

Graw et al., Database UniProt, Accession Numbe P04344; Gene. vol. 136 pp. 145-156 (1993).

Griep et al., "Fluobodies: green fluorescent single-chain Fv fusion proteins," Journal of Immunological Methods. vol. 230 pp. 121-130 (1999).

Guo et al., "Protein tolerance to random amino acid change," PNAS. vol. 101, No. 25 pp. 9205-9210 (2004).

Haaparanta, T., and Huse, W.D., "A combinatorial method for constructing libraries of long peptides displayed by filamentous phage," Mol. Diversity. vol. 1 pp. 39-52 (1995).

Hanes, J., and Pluckthun, A., "In vitro selection and evolution of functional proteins by using ribosome display," PNAS. vol. 94 pp. 4937-4942 (1997).

Hanes et al., "Picomolar affinity antibodies from a fully synthetic naive library selected and evolved by ribosome display," Nature Biotechnology. vol. 18 pp. 1287-1292 (2000).

Hanes et al., "Ribosome display efficiently selects and evolves high-affinity antibodies in vitro from Immune libraries," PNAS. vol. 95 pp. 14130-14135 (1998).

Hazes, B., and Hol, W.G.J., "Comparision the Hemocyanin β-Barrel with Other Greek Key β-Barrels: possible Importance of the 'β-Zipper' in Protein Structure and Folding," Proteins: Structure, Function, and Genetics. vol. 12 pp. 278-298 (1992).

He and Taussig, "Antibody-ribosome-mRNA(ARM) complexes as efficient selection particles for in vitro display and evolution of antibody combining sites," Nucleic Acids Research. vol. 25, No. 24 pp. 5132-5134 (1997).

Hemmingsen et al., "The tyrosine corner: A feature of most Greek key β-barrel proteins," Protein Science. vol. 3 pp. 1927-1937 (1994).

Herrmann, J.E., and Morse, S.A., "Coupling of Peroxidase to Poliovirus Antibody: Characteristics of the Conjugates and Their Use in Virus Detection," Infection and Immunity. vol. 8, No. 4 pp. 645-649 (1973).

Hoess, "Phage display of peptides and protein domains." Current Opinion in Structural Biology. vol. 3 pp. 572-579 (1993).

Holliger et al., "'Diabodies': Small bivalent and bispecific antibody fragments," PNAS. vol. 90 pp. 6444-6448 (1993).

Holliger, H., and Winter, G., "Engineering bispecific antibodies," Current Opinion in Biotechnology. vol. 4 pp. 446-449 (1993).

Hoogenboom et al., "Antibody phage display technology and its applications," Immunotechnology. vol. 4 pp. 1-20 (1998).

International Preliminary Report on Patentability corresponding to International Patent Application No. PCT/EP2004/005730 dated May 13, 2005.

International Search Report corresponding to International Patent Application No. PCT/EP2004/005730 dated Oct. 5, 2004.

International Search Report corresponding to International Patent Application No. PCT/EP2000/006698 dated Feb. 2, 2001.

Interview Summary corresponding to U.S. Appl. No. 11/283,332 dated Mar. 24, 2009.

Interview Summary corresponding to U.S. Appl. No. 11/656,646 dated Feb. 5, 2010.

Interview Summary corresponding to U.S. Appl. No. 12/072,959 dated Mar. 24, 2009.

Jaenicke, "Stability and folding of domain proteins," Progression in Biophysics and Molecular Biology. vol. 71, No. 2 pp. 155-241 (1999).

Jenkins et al., "Structure and Evolution of Parallel β-Helix Proteins," Journal of Structural Biology. vol. 122 pp. 236-246 (1998).

Jentsch, S., and Pyrowolakis, G., "Ubiquitin and its kin: how close are the family ties?" Trends in Cell Biology. vol. 10 pp. 335-342 (2000).

Jones, D., and Candido, E.P.M., "Novel Ubiquitin-like Ribosomal Protein Fusion Genes from the Nematodes *Caenorhabditis elegans* and *Caenorhabditis briggsae,*" The Journal of Biological Chemistry. vol. 268, No. 26 pp. 19545-19551 (1993).

Kieke et al., "Isolation of anti-T cell receptor scFv mutants by yeast surface display," Protein Engineering. vol. 10, No. 11 pp. 1303-1310 (1997).

Knappik et al., "Fully Synthetic Human Combinatorial Antibody Libraries (HuCAL) Based on Modular Consensus Frameworks and CDRs Randomized with Trinucleotides," Journal of Molecular Biology. vol. 296 pp. 57-86 (2000).

Koide et al., "The Fibronectin Type III Domain as a Scaffold for Novel Binding Proteins," Journal of Molecular Biology. vol. 284 pp. 1141-1151 (1998).

Ku, J., and Schultz, P.G., "Alternate protein frameworks for molecular recognition," PNAS. vol. 92 pp. 6552-6556 (1995).

Kuchner, O. and Arnold, F. H., "Directed evolution of enzyme catalysts," TIBTECH. vol. 15 pp. 523-530 (1997).

Kumar at al., "Cloning of a cDNA which encodes a novel ubiquitin-like protein," Biochemical and Biophysical Research Communications. vol. 195, No. 1 pp. 393-399 (1993).

Larsen et al., "The Ubiquitin Superfamily: Members, Features, and Phylogenies," Journal of Proteome Research. vol. 1 pp. 411-419 (2002).

Laub et al., "Localized solution structure refinement of an F45W variant of ubiquitin using stochastic boundary molecular dynamics and NMR distance restraints," Protein Science. vol. 4 pp. 973-982 (1995).

Lazar, C.N., and Wang, H., "De novo design of the hydrophobic core of ubiquitin," Protein Science. vol. 6 pp. 1167-1178 (1997).

Mandel et al., "Structure and Stability of γ-Crystallins: Denaturation and Proteolysis Behaviour," The Journal of Biological Chemsitry. vol. 262, No. 17 pp. 8096-8102 (1987).

Manns et al., "The way forward in HCV treatment—finding the right path," Nature Reviews Drug Discovery. vol. 6 pp. 991-1000 (2007).

Marx, J. "Ubiquitin Lives Up to Its Name," Science. vol. 297 pp. 1792-1794 (2002).

Mayr et al., "Domain Interactions and Connecting Peptides in Lens Crystallins," Journal of Molecular Biology. vol. 235 pp. 84-88 (1994).

McConnell et al., "Construction and screening of M13 phage libaries displaying long random peptides," Molecular Diversity. vol. 1 pp. 165-176 (1995).

McConnell, S.J., and Hoess, R.H. "Tendamistat as a Scaffold for Conformationally Constrained Phage Peptide Libraries," The Journal of Molecular Biology. vol. 250 pp. 460-470 (1995).

Michiels et al., "*fau* cDNA encodes a ubiquitin-like-S30 fusion protein and is expressed as an antisense sequence in the Finkel-Biskis-Reilly murine sarcoma virus," Oncogene. vol. 8 pp. 2537-2546 (1993).

Miura et al., "Characterization of the Binding Interface between Ubiquitin and Class I Human Ubiquitin-conjugating Enzyme 2b by Multidimensional Heteronuclear NMR Spectroscopy in Solution," Journal of Molecular Biology. vol. 290 pp. 213-228 (1999).

Muller et al., "Recombinant single-chain Fv antibody fragment-alkaline phosphatase conjugate for one-step immunodetection in molecular hybridization," Journal of Immunological Methods. vol. 227 pp. 177-185 (1999).

Müller et al., "SUMO, ubiquitin's mysterious cousin," Nat. Rev. Mol. Cell Biol. vol. 2 pp. 202-210 (2001).

Müller, H.N., and Skerra, A., "Grafting of a High-Affinity Zn(II)-Binding Site on the β-Barrel of Retional-Binding Protein Results in Enhanced Folding Stability and Enables Simplified Purification," Biochemistry. vol. 33, No. 47 pp. 14126-14135 (1994).

Murzin et al., "SCOP: A Structural Classification of Proteins Database for the Investigation of Sequences and Structures," Journal of Molecular Biology. vol. 247 pp. 536-540 (1995).

Najmudin et al., "Structure of the Bovine Eye Lens Protein γB(γII)-Crystallin at 1.47 Å," Acta Cryst. vol. D49 pp. 223-233 (1993).

Nissim et al., "Antibody fragments from a 'single pot' phage display library as immunochemical reagents," The EMBO Journal. vol. 13, No. 3 pp. 692-698 (1994).

Nord et al., "Binding proteins selected from combinatorial libraries of an α-helical bacterial receptor domain," Nature Biotechnology. vol. 15 pp. 772-777 (1997).

Notice of Allowance corresponding to U.S. Appl. No. 10/030,605 dated Apr. 14, 2009.

Notification of Transmittal Translation of the International Preliminary Report on Patentability (Chapter I of the Patent Cooperation Treaty) corresponding to International Patent Application No. PCT/EP2004/005730 dated Apr. 13, 2006.

Nygren, P., and Uhlen, M., "Scaffolds for engineering novel binding sites in proteins," Current Opinion in Structural Biology. vol. 7 pp. 463-469 (1997).

Odegrip et al., "CIS display: in vitro selection of peptides from libraries of protein-DNA complexes," PNAS vol. 101, No. 9 pp. 2806-2810 (2004).

Official Action corresponding to U.S. Appl. No. 10/030,605 dated Sep. 21, 2004.

Official Action corresponding to U.S. Appl. No. 10/030,605 dated Feb. 15, 2005.

Official Action corresponding to U.S. Appl. No. 10/030,605 dated Aug. 10, 2005.

Official Action corresponding to U.S. Appl. No. 10/030,605 dated Apr. 12, 2006.

Official Action corresponding to U.S. Appl. No. 10/030,605 dated Feb. 28, 2007.

Official Action corresponding to U.S. Appl. No. 10/030,605 dated Nov. 16, 2007.

Official Action corresponding to U.S. Appl. No. 10/030,605 dated Jul. 1, 2008.

Official Action corresponding to U.S. Appl. No. 11/283,332 dated Jan. 9, 2008.

Official Action corresponding to U.S. Appl. No. 11/283,332 dated May 30, 2008.

Official Action corresponding to U.S. Appl. No. 11/283,332 dated Nov. 28, 2008.

Official Action corresponding to U.S. Appl. No. 11/283,332 dated Sep. 4, 2009.

Official Action corresponding to U.S. Appl. No. 11/283,332 dated Mar. 3, 2010.

Official Action corresponding to U.S. Appl. No. 11/656,646 dated Sep. 1, 2009.

Official Action corresponding to U.S. Appl. No. 11/656,646 dated Nov. 13, 2009.

Official Action corresponding to U.S. Appl. No. 11/656,646 dated May 25, 2010.

Official Action corresponding to U.S. Appl. No. 12/072,959 dated Jul. 24, 2008.

Official Action corresponding to U.S. Appl. No. 12/072,959 dated Jan. 27, 2009.

Official Action corresponding to U.S. Appl. No. 12/072,959 dated Jan. 5, 2010.

Pack, P., and Pluckthun, A., "Miniantibodies: Use of Amphipathic Helices to Produce Functional, Flexibly Linked Dimeric Fv Fragments with High Avidity in *Escherichia coli,*" Biochemsitry. vol. 31, No. 6 pp. 1579-1584 (1992).

Palme et al., "Mutational analysis of hydrophobic domain interactions in γβ-crystallin from bovine eye lens," Protein Science. vol. 6 pp. 1529-1536 (1997).

Pannekoek et al, "Functional display of human plasminogen-activator inhibitor 1 (PAI-1) on phages: novel perspectives for structure-function analysis by error-prone DNA synthesis," Gene. vol. 128 pp. 135-140 (1993).

Pantoliano et al., "Conformational Stability, Folding, and Ligand-Binding Affinity of Single-Chain Fv Immunoglobulin Fragments Expressed in *Escherichia coli,*" Biochemistry. vol. 30 pp. 10117-10125 (1991).

Pickersgill et al., "Crystal Structure of Polygalacturonase from *Erwinia caratovora* ssp. *carotovora,*" The Journal of Biological Chemistry. vol. 273, No. 38 pp. 24600-24664 (1998).

Raetz, C.H.R., and Roderick, S.L., "A Left-Handed Parallel β Helix in the Structure of UDP-*N*-Acetylglucosamine Acyltransferase," Science. vol. 270, No. 5238 pp. 997-1000 (1995).

Reiter, Y., and Pastan, I., "Recombinant Fv immunotoxins and Fv fragments as novel agents for cancer therapy and diagnosis," TIBTECH. vol. 16 pp. 513-520 (1998).

Richardson et al., "Looking at proteins: representations, folding, packing, and design," Biophysical Journal. vol. 63 pp. 1186-1209 (1992).

Riddle et al., "Functional rapidly folding proteins from simplified amino acid sequences," Nature Structural Biology. vol. 4, No. 10 pp. 805-809 (1997).

Rudinger, "Characteristics of the amino acids as components of a peptide hormone sequence," Peptide Hormones, University Park Press, Baltimore, MD. pp. 1-7 (1976).

Rudolph et al., "Folding of an all-β protein: Independent domain folding in γll-crystallin from calf eye lens," PNAS. vol. 87 pp. 4625-4629 (1990).

Saviranta et al., "Engineering the steroid-specificity of an anti-17β-estradiol Fab by random mutagenesis and competitive phage panning," Protein Engineering. vol. 11, No. 2 pp. 143-152 (1998).

Schaffitzel et al., "In Vitro Selection and Evolution of Protein-Ligand Interactions by Ribosome Display," Protein-Protein Interactions, A Molecular Cloning Manual, E. Golemis, Ed. Cold Spring Harbor Laboratory Press, New York. Chapter 30 pp. 535-567 (2001).

Seffernick et al., "Melamine Deaminase and Atrazine Chlorohydrolase: 98 Percent Identical but Functionally Different," Journal of Bacteriology, Apr. 2001, vol. 183, No. 8, pp. 2405-2410.

Shrake and Rupley, "Environment and Exposure to Solvent of Protein Atoms. Lysozyme and Insulin," J. Mol. Biol. vol. 79 pp. 351-371 (1973).

Skerra, "Engineered protein scaffolds for molecular recognition," Journal of Molecular Recognition. vol. 13, No. 4 pp. 167-187 (2000).

Skerra and Plückthun, "Assembly of a Functional Immunoglobulin Fv Fragment in *Escherichia coil*," Science vol. 240 pp. 1038-1041 (1988).

Slingsby, "Structural variation in lens crystallins," TIBS. vol. 10 pp. 281-284 (1985).

Slingsby, C., and Clout, N. J., "Structure of the Crystallins," Eye (London). vol. 13 pp. 395-402 (1999).

Smith, "Filamentous Fusion Phage: Novel Expression Ventors That Display Cloned Antigens on the Virion Surface," Science. vol. 228 pp. 1315-1317 (1985).

Smith et al., "Small Binding Proteins Selected from a Conbinatorial Repertoire of Knottins Displayed on Phage," Journal of Molecular Biology. vol. 277, No. 2 pp. 317-332 (1998).

Stahl, S., and Uhlen, M., "Bacterial surface display: trends and progress," TIBTECH. vol. 15 pp. 185-192 (1997).

Stemmer, "Rapid evolution of a protein in vitro by DNA shuffling," Nature. vol. 370 pp. 389-391 (1994).

Vijay-Kumar et al., "Structure of Ubiquitin Refined at 1.8 Å Resolution," J. Mol. Biol. vol. 194 pp. 531-544 (1987).

Vijay-Kumar et al., "Three-dimensional structure of ubiquitin at 2.8 Å resolution," PNAS. vol. 82 pp. 3582-3585 (1985).

Voet and Voet, Biochemistry. Chapter 7. Three-Dimensional Structures of Proteins. pp. 171 and 175 (1990).

Wang et al., "Prevalence, Genotypes, and an Isolate (HC-C2) of Hepatitis C Virus in Chinese Patients With Liver Disease," Journal of Medicinal Virology. vol. 40 pp. 254-260 (1993).

Wells, "Additivity of Mutational Effects in Proteins," Biochemistry. vol. 29, No. 37 pp. 8509-8517 (1990).

Wells and Lowmann, "Rapid evolution of peptide and protein binding properties in vitro," Current Opinion in Biotechnology. vol. 3 pp. 355-362 (1992).

Winter, "Synthetic human antibodies and a strategy for protein engineering," FEBS Letters. vol. 430 pp. 92-94 (1998).

Wintrode et al., "Thermodynamics of Ubiquitin Unfolding," Proteins: Structure, Function and Genetics. vol. 18 pp. 246-253 (1994).

Wistow et al., "X-ray Analysis of the Eye Lens Protein y-ll-Crystallin at 1.9 A Resolution," Journal of Molecular Biology. vol. 170 pp. 175-202 (1983).

Wistow, G.J., and Piatigorsky, J., "Lens crystallins: the evolution and expression of proteins for a highly specialized tissue," Annual Review of Biochemistry. vol. 57 pp. 479-504 (1988).

Xia et al., "Crystal structure of the receptor-binding domain of adenovirus type 5 fiber protein at 1.7 A resolution," Structure. vol. 2 pp. 1259-1270 (1994).

You, L., and Arnold, F.H., "Directed evolution of subtilisin E in *Bacillus subtills* to enhance total activity in aqueous dimethylformamide," Protein Engineering. vol. 9, No. 1 pp. 77-83 (1994).

Young et al., "Thermal stabilization of a single-chain Fv antibody fragment by introduction of a disulphide bond," FEBS Letters. vol. 377 pp. 135-139 (1995).

Zhang et al., "Directed evolution of a fucosidase from a galactosidase by DNA shuffling and screening," PNAS. vol. 94 pp. 4504-4509 (1997).

\* cited by examiner

UBIQUITIN OR GAMMA-CRYSTALLINE CONJUGATES FOR USE IN THERAPY, DIAGNOSIS AND CHROMATOGRAPHY

RELATED APPLICATIONS

This application is a continuation of PCT International Patent Application No. PCT/EP2005/010932, filed Oct. 11, 2005, which claims priority to German Patent Application No. 102004049479.7, filed Oct. 11, 2004, the disclosures of each of which are incorporated herein by reference in their entirety.

TECHNICAL FIELD

The present invention relates to conjugates which contain a covalent linkage between one or more polypeptide molecules based on gamma-crystallin or ubiquitin and one or more functional component. The present invention furthermore relates to a method for the preparation of a conjugate of this type as well as to the use of the conjugate in diagnostics, therapy and chromatography.

BACKGROUND ART

Gamma-II-crystallin belongs to the family of beta-gamma-crystallins and is a structural protein of the eye lens with ubiquitary distribution in vertebrates (Jaenicke & Slingsby, 2001). Beta-gamma-crystallins form a highly homologous protein family characterized by two structurally identical domains and consisting largely of beta sheet structures (Wistow & Piatigorsky, 1988). The superimposed structural motif of the beta-gamma-crystallins is the so-called greek key topology. It consists of four antiparallel beta strands two of which—lying one over the other—form a domain of the crystallins (Blundell et al., 1981).

The natural function of the crystallins is based on the generation of a high refractive index in the lens of the eye which is achieved by an extremely high local protein concentration of up to 860 mg/ml (Kumaraswamy et al., 1996). Due to their spatial structure, crystallins are very stable and readily soluble proteins having a high protease resistance. Furthermore, the localization in the interior of the eye lens has the effect that gamma-crystallins are not subject to protein turnover. Therefore, beta-gamma-crystallins have one of the highest half-lives known for proteins (Jaenicke, 1996).

The best characterized member of this protein family is bovine gamma-crystallin. The spatial structure could be determined for the wild type of the protein at different resolutions as well as for a whole range of point mutants (Najmudin et al., 1993; Kumaraswamy et al., 1996; Norledge et al., 1996). This revealed that the protein is stabilized via a hydrophobic cleft between the two domains. This cleft is formed by intramolecular interactions of six hydrophobic residues consisting of three residues in the N-terminal domain and the three topologically identical residues in the C-terminal domain (Wistow et al., 1983). Die stability to chemical agents is largely independent of the short peptide linking the two domains (Mayr et al., 1994).

Bovine gamma-crystallin has a size of approx. 20 kDa and is characterized by an extraordinarily high stability. It is resistant to 8 M urea at a neutral pH. In a pH range of 1 to 9 it is present in its native state (Rudolph et al., 1990; Sharma et al., 1990), and even up to a temperature of 75° C. the protein is stable in 7 M urea (Jaenicke, 1994). The recombinant cytosolic expression of gamma-crystallins in *E. coli* is successful with very high yields (Mayr et al., 1994).

The protein-chemical properties—high stability, low molecular weight, high cytosolic expression rates—makes the protein class of gamma-crystallins attractive candidates for the generation of alternative binding molecules.

A phagemide library (GCUC1) has been established by Fiedler & Rudolph on the basis of the bovine gamma-II-crystallin as a scaffold protein wherein eight surface-exposed amino acids at positions 2, 4, 6, 15, 17, 19, 36 and 38 (without the starting methionine) were randomized on the DNA level. After several rounds of selection by means of phage display, variations with specific binding to estradiol and an affinity in the μM range could be detected. These results have shown that binding properties which did not exist before can be generated de novo on the bovine gamma-II-crystallin and that gamma-crystallins are generally suitable as scaffold proteins (scaffold) for the isolation of alternative binding molecules (see patent DE19932688 A1).

In subsequent works a new library was established on the basis of the human gamma-II-crystallin. The selection of the human gamma-II-crystallin as the scaffold and the accompanying construction of a new library hat important advantages: 1. Compared to the bovine protein the human gamma-II-crystallin has a significantly higher stability to denaturing influences, 2. the human origin of the protein should result in a very low immunogenicity of the respective variations in therapeutic applications and 3. a newly constructed library having a higher complexity should enable the isolation of binding molecules with higher affinity (Ling 2003). Similar to the GCUC1 library the same eight amino acid positions (without the starting methionine position 2, 4, 6, 15, 17, 19, 36, 38) were selected for randomization. The new library CR20 established according to described methods (patent DE19932688 A1) on the basis of the human gamma-II-crystallin has a theoretical size of $5 \times 10^8$ independent variations each of which is represented about 130 times in the library. After sequencing of more than 200 independent variations it was found that more than 80% of all variations had substitutions only in the eight randomized positions. Furthermore, the sequences of the variations in the substituted positions except the third codon position showed an almost identical distribution of all possible nucleotides. Thus, this library which has all 32 possible codons in the eight randomized positions is of high quality.

As a second scaffold protein for the generation of alternative binding molecules use is made of human ubiquitin. Ubiquitin is a small, monomeric and cytosolic protein which—highly conserved in its sequence—is present in all known eukaryotic cells from protozoa to vertebrates. In the organism, it plays a fundamental role in the regulation of the controlled degradation of cellular proteins.

The polypeptide chain of ubiquitin consists of 76 amino acids which are folded in an extraordinarily compact alpha/beta structure (Vijay-Kumar, 1987): Almost 87% of the polypeptide chain are involved in the formation of the secondary structural elements via hydrogen bonds. As the prominent is secondary structures three and a half alpha-helical turns as well as an antiparallel beta sheet consisting of five strands can be mentioned. The characteristic arrangement of these elements—an antiparallel beta sheet exposed to a surface of the protein onto the back side of which an alpha helix is packed which lies vertically on top of it—is generally considered as so-called ubiquitin-like folding motif. Another structural feature is a marked hydrophobic region in the interior of the protein between the alpha helix and the beta sheet.

Because of its small size, the artificial preparation of ubiquitin can be carried out both by chemical synthesis and by means of biotechnological methods. Due to the favorable folding properties, ubiquitin can be produced by genetic engineering using microorganisms such as e.g. *E. coli* in relatively large amounts either in the cytosol or in the periplasmic space.

Due to the simple and efficient bacterial preparation, ubiquitin can be used as a fusion partner for other foreign proteins to be prepared the production of which is problematic. By means of the fusion to ubiquitin an improved solubility and thereby an improved yield can be achieved (Butt et al., 1989).

On the basis of available data on the crystal structure (PDB data base entry 1UBI) using computerized analysis the positions of those amino acids in the ubiquitin protein scaffold could be localized the side chains of which are exposed to the surface i.e. to the solvent or a potential binding partner. The positions selected are localized in spatial proximity to each other at the beginning of the first aminoterminal beta sheet strand (pos. 2, 4, 6) as well as in the loop (pos. 62, 63) and at the beginning of the carboxyterminal beta sheet strand (pos. 64, 65, 66), respectively, forming with their amino acid side chains a contiguous region on the surface of ubiquitin. In this way, a surface-exposed hypervariable region was generated by random amino acid substitutions in the analyzed region on the still intact protein structure of ubiquitin (PCT/EP2004/005730, unpublished).

The generation of an artificial binding surface on a beta sheet protein represents a novel and interesting alternative to conventional antibodies. Evidence was obtained that a new, artificially generated binding site on the surface of gamma-crystallins or ubiquitin-like proteins results in functional binding molecules (DE 19932688 A1) (PCT/EP2004/005730, unpublished).

However, up to now there was no suggestion or indication as to the coupling of these polypeptide molecules to another component to form a conjugate rendering them useful for diagnostic, therapeutic and analytic applications without encountering a loss of function of one of the two or of both components.

SUMMARY

Thus, the object underlying the presently disclosed subject matter is to provide a conjugate between a polypeptide based on gamma-crystallin or ubiquitin and a functional component wherein the respective polypeptide molecule has a binding property for the specific binding to a ligand which is altered as compared to the wild type polypeptide wherein both components of the conjugate after they have been coupled to each other have their functionality retained or even enhanced by such coupling.

It is another object of the present invention to provide a method by which such conjugates can be identified, prepared and examined for their functional properties.

These objects are achieved by the subject matter of the independent claims. Preferred embodiments can be seen from the dependent claims.

DETAILED DESCRIPTION

Figure 1:
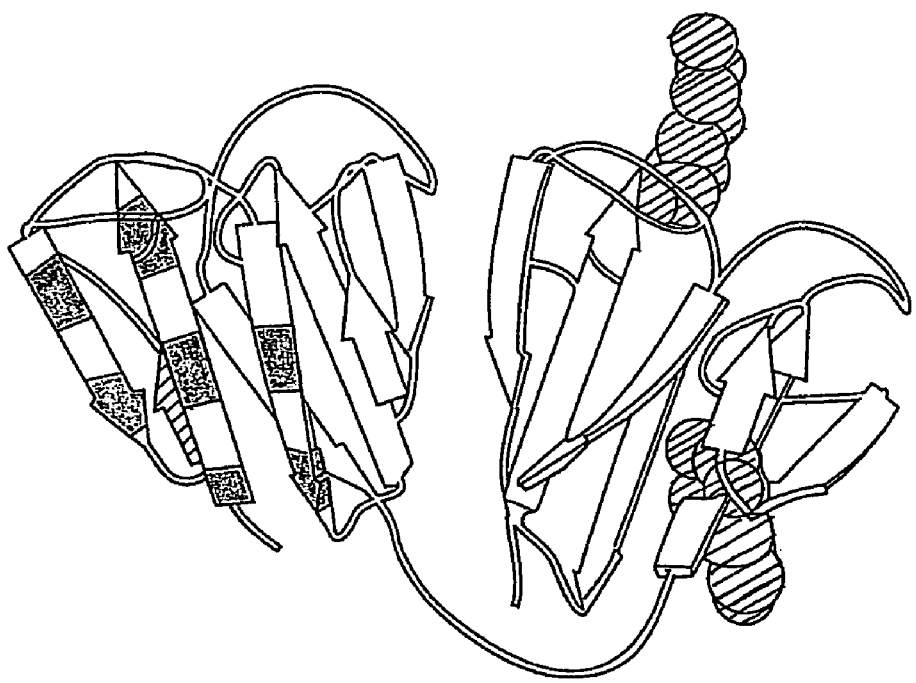
FIG. 1: Spatial structure of gamma-II-crystallin. The de novo generated binding surface in the N-terminal domain is shown by shading. The C-terminal position of the lysine residues localized outside of the binding surface is emphasized by cross-hatched calottes.

The present invention relates to the site-specific and selective, undirected coupling of novel binding proteins based on gamma-crystallin and ubiquitin to various molecules such as e.g. proteins (chromophore proteins and enzymes), matrices (e.g. dextrane, polymethacrylate, agarose, sepharose, polystyrene derivatives and cellulose) and small molecules (for example fluorescent markers, biotin, digoxigenin, radioisotopes, antibiotics among others). These so-called Affilin™ molecules are characterized by the de novo design of a binding region in beta sheet structures of the proteins. Thus, they differ from the most prominent class of binding proteins in nature, the antibodies, in which the binding region is localized in flexible loop areas (CDR's) of the protein. Another difference between Affilin™ and antibodies is the size of the molecules. The two polypeptides employed as the basis of the first component of the conjugates according to the invention have a molecular weight of 20 (gamma-crystallin) and 10 kDa (ubiquitin), respectively, while antibodies have a molecular weight of 150 kDa (IgG).

The present invention comprises processes for the preparation of conjugates from these polypeptides and the respective coupling partners as well as the use thereof in different applications and surprisingly shows that these coupling methods neither result in a loss of the biological activity of the coupling partner nor in a loss of the binding properties of the polypeptides to their ligands.

Exemplarily for the invention, the coupling of the polypeptide components to a dextrane matrix in the BIACORE system, the coupling to the fluorescent dye Oyster®556, the chromophore protein phycoerythrin (PE) and the horseradish peroxidase enzyme as well as the immobilization of a polypeptide to a support material for use in affinity chromatography are described. According to the invention, the couplings were performed either directly to the polypeptide molecule, e.g. to nucleophilic side chains of the proteins, or in a targeted manner to C-terminal peptide linkers. Surprisingly, the coupling methods could be applied to both scaffolds and did not result in an impairment of the binding properties of these molecules. It was especially unexpected that the relatively small polypeptide molecules (10 and 20 kDa, respectively) could be coupled to large proteins such as e.g. phycoerythrin (240 kDa) while retaining their binding activity.

Surprisingly, the conjugates obtained in this manner do not limit the binding capability of the Affilin™ molecules, in contrast an increase in the macroscopic dissociation constant (avidity effect) could be observed with certain conjugates enabling other possibilities of use of the polypeptide molecules e.g. in therapy. Furthermore, it was found that these polypeptide molecules show binding activity also after coupling to water-insoluble matrices and that they can be regenerated, i.e. their binding properties can be restored, after treatment with denaturating agents such as urea, guanidinium, ethanol, sodium hydroxide or hydrochloric acid.

A detailed analysis of the structural data of molecules based on gamma-crystallin and ubiquitin provided for the possibility to render the unspecific coupling selective by specifically targeting lysine residues. Structural analysis showed that in gamma-crystallin lysines are present in the C-terminal domain of the protein and thus should be suitable for coupling (FIG. 1). Also in ubiquitin it was possible to identify such lysine residues. However, before performing these coupling strategies it must be ensured that there are no other lysines in the binding region.

For the present invention, polypeptides with specific binding to IgG Fc (of human origin) or proNGF were selected from a human gamma-crystallin library (CR20) and an NGF-binding polypeptide was selected from the human ubiquitin library (UB10), and they were subsequently purified. By introducing a specific C-terminal peptide linker of defined length which included a cysteine it was possible to modify polypeptide molecules in a manner that selective coupling without impairment of the binding activity was obtained. For efficient coupling it is necessary to eliminate all remaining accessible cysteines. By the unspecific coupling method of the polypeptide molecules it was surprisingly possible to retain the binding activity of the polypeptides and moreover to achieve an increase in the affinity by means of avidity and thus to prepare a very attractive polypeptide-based molecule conjugate for diagnostics and therapy.

Such alternative binding molecules find many uses in therapy, diagnostics and chromatography. By the coupling of polypeptides to various partners an even broader field of use will be provided for these novel binding molecules.

The present invention particularly comprises the following aspects and embodiments:

According to a first aspect the present invention relates to a conjugate comprising the following components:

one or more polypeptide molecules based on gamma-crystallin or ubiquitin (I) each having a binding property for specific binding to a ligand which is newly generated or altered as compared to the corresponding wild type polypeptide and, covalently linked thereto, one or more functional components (II) wherein after coupling of (I) to (II) the functionality of all components is retained.

In other words, the conjugate according to the invention does not comprise ubiquitin or gamma-crystallin in their wildtype form but only in a form adapted to specific ligands. This specifically adapted form provides for altered (improved) or newly generated binding properties to the respective ligands as compared to the wildtype form. As a common principle of the polypeptide molecules based on gamma-crystallin or ubiquitin it shall be pointed out that in both an artificial binding surface on a beta sheet structure is generated to enable specific binding to a ligand of interest. Therefore, the presence of at least one beta sheet structure to provide an artificial binding surface is an essential feature of the invention.

In this context, a conjugate refers to the posttranslational, covalent linkage of a polypeptide molecule to another component and therefore differs e.g. from a fusion of polypeptides on the genetic level. Fusion polypeptides are the result of a so-called fusion.

According to the invention the polypeptide molecule based on ubiquitin is preferably selected from the group consisting of proteins of the protein superfamily of "ubiquitin-like proteins", proteins having an ubiquitin-like folding motif as well as fragments or fusion proteins thereof which have an ubiquitin-like folding motif wherein due to one or more modifications of amino acids in at least one surface-exposed region of the protein comprising at least one beta sheet strand of the beta sheet region and optionally non-beta sheet regions the protein has a binding affinity to a predetermined binding partner or ligand, respectively, which was not present before while the ubiquitin-like folding motif is retained.

Thus, the invention comprises a protein modified by substitution, insertion, deletion, chemical modification or combinations thereof selected from the group consisting of proteins of the protein superfamily of "ubiquitin-like proteins", proteins having an ubiquitin-like folding motif as well as fragments or fusion proteins thereof each of which having an ubiquitin-like folding motif wherein the protein due to this modification shows a binding affinity with respect to a predetermined binding partner that did not exist previously which is obtainable by the following method:

a) selecting a protein to be modified;
b) determining a binding partner;
c) selection of amino acids in at least one surface-exposed region of the protein including at least one beta sheet strand of the beta sheet region and optionally non-beta sheet regions;
d) modifying the selected amino acids by substitution, insertion, deletion and/or chemical modification while the ubiquitin-like folding motif is retained;
e) contacting the modified protein with the binding partner determined in step b);
f) detecting those proteins having a binding affinity to the binding partner predetermined in step b).

Furthermore, the respective methods for the preparation of the above-mentioned ubiquitin-based modified proteins and uses of these modified proteins are described.

Accordingly, the ubiquitin-based polypeptide molecule (I) employed in the conjugate according to the invention is preferably prepared by modification of proteins or polypeptides, respectively, having an ubiquitin-like folding motif as defined in the present application. These include the proteins of the protein superfamily of "ubiquitin-like-proteins", all proteins having an ubiquitin-like folding motif and fragments or fusion proteins of these proteins, with the proviso that they also have an ubiquitin-like folding motif. Starting is from these proteins or polypeptides, respectively, one or more amino acids in the original protein or polypeptide, respectively, are modified. The modifications particularly comprise the substitution of amino acids, but also insertions and deletions of one or more amino acids as well as chemical modifications of amino acids. These modifications are performed in at least one surface-exposed region of the protein to be modified. The modification of at least one amino acid comprises at least one beta sheet strand of the beta sheet region wherein the beta sheet strand must be localized at the surface of the protein so that it is accessible to the binding partner or the ligand, respectively, which is able to bind to the modified protein with an affinity which can be determined. In another embodiment of the invention, in addition to the alterations in the beta sheet strand of the beta sheet region also non-beta sheet regions are modified which preferably are surface-exposed in order to affect, particularly to increase, the binding affinity with respect to the predetermined binding partner and thus to enhance the specificity.

Various techniques known per se for the modification of one or more amino acids are available to those skilled in the art. These will be described in more detail in the following. In addition, reference is made to the publications of Ausuebel et al., 1994, as well as Sambrook et al., 1989.

Modifications of amino acids of the non-surface-exposed core region of ubiquitin are already known (Finucane et al., 1999; Lazar et al., 1997). The alterations made therein are directed to positions which due to their localization within the hydrophobic core are not involved in binding since they are not accessible to the solvent or to possible binding partners.

The meaning of the term "binding property that did not exist previously" and de novo generated artificial binding site and "binding property for specific binding to a ligand altered as compared to the wild type protein", is respectively, in the context of this invention will be explained in the following. These terms are intended to mean that the modified protein in the modified region has previously shown no binding property to a predetermined binding partner or to a natural binding partner of ubiquitin.

The binding partners which can also be defined as ligands have a measurable affinity to the protein modified according to the invention. A dissociation constant for the complex formed of $K_D=10^{-5}$ M or smaller can be regarded as a minimal value according to the invention for the presence of a quantifiable binding property, i.e. the affinity with which the partner is bound. A value of $10^{-5}$ M and below can be considered as a quantifiable binding affinity. Depending on the application a value of $10^{-6}$ M to $10^{-12}$ M is preferred, further preferably $10^{-7}$ to $10^{-11}$ M for e.g. chromatographic applications or $10^{-9}$ to $10^{-12}$ M for e.g. diagnostic or therapeutic applications. Further preferred binding affinities are in the range of $10^{-7}$ to $10^{-10}$ M, preferably up to $10^{-11}$ M. The methods for the determination of the binding affinities are known per se and are described further on the following pages. Modification according to the invention is intended to mean substitutions of amino acids, insertions, deletions or chemical modifications.

As the proteins to be modified according to the invention proteins of the superfamily of "ubiquitin-like proteins" can be used. According to the invention, this superfamily comprises the subgroups listed in Murzin et al. (1995). These include for example the protein families of "ubiquitin-related proteins", "UBX domain", "GABARAP-like", "RAS-binding domain", etc. Preferably, proteins of the protein family of "ubiquitin-related proteins" are 3.0 used. According to the invention also those proteins are comprised which have an ubiquitin-like folding motif. Examples of these are SUMO-1, FAU, NEDD-8, UBL-1, and GDX as well as Rub1, APG8, ISG15, URM1, HUB1, elongin B, PLIC2 (N-terminal domain), human parkin (N-terminal domain).

The proteins which may be used according to the invention from the superfamily of ubiquitin-like proteins have been characterized to a high extent. Only by way of example reference is made to the world-wide web page for the Weizmann Institute of Science. According to this site, the family of ubiquitin-like proteins is defined as a superfamily to which the family of ubiquitin-related proteins belongs. All members of this superfamily are characterized primarily by β sheets arranged in an antiparallel manner and subdivided into α and β segments. The folding is defined as beta-Grasp and thus as ubiquitin-like. The core region is defined as follows: beta(2)-alpha-beta(2) wherein the numbers indicate the number of strands and the totality of strands forms the β sheet. The arrangement of the mixed beta sheet is 2143 referring to the position of the strands if the sheet is seen from the top from left to right (amino terminus at the bottom, carboxy terminus on top). A characteristic feature of the members of the ubiquitin-like proteins thus is an antiparallel β sheet exposed to one surface of the protein onto the back side of which an α helix is packed which lies perpendicularly on top of it. This ubiquitin-like folding motif is a characteristic feature of the proteins which can be used and modified according to the invention and clearly distinguishes the members of the family from other proteins. In view of this definition, also the ubiquitin-like N-terminal domain of PLIC-2 and the ubiquitin-like domain of parkin are comprised by the invention.

Those skilled in the art can, either by using sequence comparisons, so-called alignments, or by means of structure superimpositions, preliminarily judge whether the proteins are a member of the protein superfamily of ubiquitin-like proteins or not. Naturally, the last evidence is always provided by a structural analysis, for example a structural analysis by X-ray crystallography or multidimensional nuclear magnetic resonance spectroscopy. Recently also structural analyses using genetic algorithms have achieved good predictions.

Further information with respect to the ubiquitin superfamily can be found for example in the publication of Larsen et al., 2002. In addition, reference is also made to the publication by Buchberger et al., 2001. Buchberger describes the typical β Grasp fold as a characteristic feature of ubiquitin-like proteins having a secondary structure of the organization beta-beta-alpha-beta-beta-alpha-beta, i.e. an arrangement of five beta-strands in the form of a "mixed sheet" in a 21534 arrangement. In this respect, it has to be pointed out that UBX has no significant homology in its primary sequence to e.g. ubiquitin (Buchberger et al., 2001) but in spite of this fact—due to its three-dimensional structure which is identical to that of e.g. ubiquitin—is grouped among the ubiquitin-like proteins. In this respect it shall be mentioned that in ubiquitin also the amino acids at positions 48 and 49 are sometimes considered as a distinct beta strand (Vijay-Kumar, 1987). This fifth strand which would be localized behind the helix in the ubiquitin structure and provide the "mixed sheet" with the 21534 arrangement, however, consists of only two amino acids, and it is actually doubtful whether this strand of two amino acids can be called a beta sheet strand or not. However, as explained above according to Buchberger et al. (2001) also proteins having a 21534 arrangement could be classified without any problems into the superfamily of ubiquitin-like proteins. For the present invention, the definition 21543 which is described in more detail above was selected for the arrangement of the beta strands in ubiquitin.

The proteins of the above-mentioned family and superfamily are usually highly conserved. According to what is known to date, ubiquitin has an identical amino acid sequence in all mammals for example. Ubiquitin of yeast differs in only three amino acids from this sequence. Human ubiquitin or ubiquitin of mammals, respectively, consist of 76 amino acids and have the structure described in the beginning.

The modified protein employed according to the invention should have at least 30%, preferably at least 40% or 50%, further preferably at least 60%, at least 70%, at least 80%, at least 90%, or at least 95% identity in its amino acid sequence to the starting protein which is modified, e.g. to human ubiquitin wherein in any case the protein has an ubiquitin-like folding motif as detailed above.

According to the present invention, the protein selected for the preparation of the modified protein is preferably human ubiquitin or ubiquitin of a different origin, for example a different mammalian ubiquitin. As the mammalian ubiquitins there can be particularly used ubiquitins of rodents, of domestic animals and agricultural animals in the field of mammals. If the field of use of the proteins prepared according to the invention is known, i.e. if the modified protein shall be for example used as a pharmaceutical composition for the treatment of diseases in humans, a human protein can be preferably used as the starting protein to be modified; this applies to other fields of use in an analogous manner.

Human and mammalian ubiquitin, respectively, has 76 amino acids. The amino acids of the four beta strands which contribute to the formation of the antiparallel beta sheet according to the structure 1UBQ in the PDB data base (available at the world-wide web page for the Research Collaboratory for Structural Bioinformatics) are the following amino acid positions according to the invention:

First strand (aminoterminal): 2 to 7; second beta sheet strand: 12 to 16; third strand: 41 to 45; fourth strand (carboxyterminal): 66 to 71. The position of the strands if the sheet is viewed from the top (amino terminus at the bottom, carboxy terminus on top) from left to right is: 2nd, 1st, 4th, 3rd strand wherein the polypeptide chain between the 1st and 4th strands forms the alpha helix.

Selection and Modification of the Amino Acids to be Modified:

On the basis of corresponding structural data such as e.g. those freely available in Protein Data Bank™ (Berman et al., 2000; the world-wide web page for the Research Collaboratory for Structural Bioinformatics) the positions of those amino acids in the starting protein, e.g. in the ubiquitin protein scaffold, whose side chains are surface-exposed, i.e. directed towards the solvent or a potential binding partner, can be localized by means of computerized analysis. Furthermore, those amino acids in the starting protein, e.g. in ubiquitin, whose random substitution presumably would have no or only a slightly negative effect on the stability of the protein scaffold can be identified by computerized analysis.

This information can provide a first indication as to the suitability of every single amino acid as an element of a binding site which then requires practical examination. In a preferred embodiment of the present invention for example the amino acids at positions 2, 4, 6, 62, 63, 64, 65, and 66 in human ubiquitin were selected due to their exposition to the surface and the tolerance of the overall structure to their random substitution.

The above-mentioned positions are localized in spatial proximity to each other at the beginning of the first amino-terminal beta sheet strand (pos. 2, 4, 6) as well as in the loop (pos. 62, 63) or at the beginning of the carboxyterminal beta sheet strand (pos. 64, 65, 66), respectively, and form with their amino acid side chains a contiguous region on the surface of ubiquitin (FIG. 1). By means of random amino acid substitutions ("randomization") in the region analyzed there can thus be generated—in a manner analogous to the antigen binding site of antibodies—a hypervariable surface-exposed region on the otherwise intact protein structure of ubiquitin.

Figure 2A:
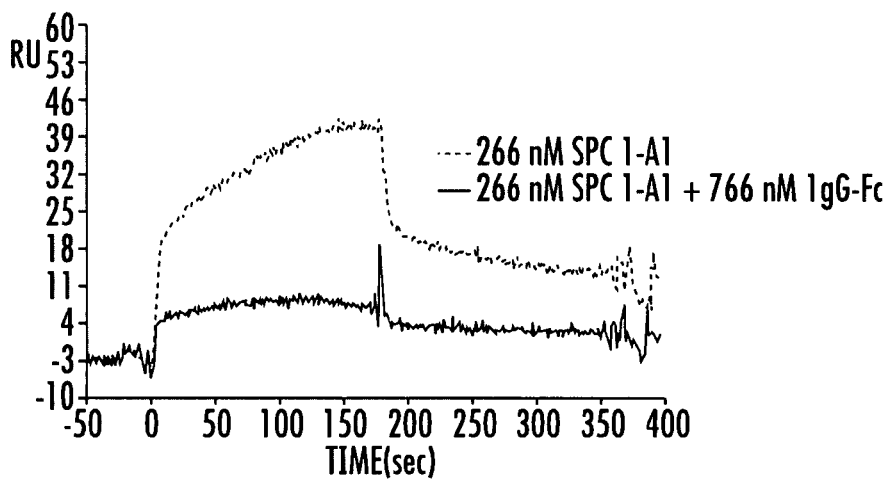
FIG. 2: Sensorgrams of the Biacore experiments for competing the binding of the Affilin™ variations SPC1-A1 (A), SPC1-A7 (B) and SPC-1-G3 (C) to a CM5 chip with immobilized IgG Fc. For the experiments 180 RU of polyclonal IgG Fc were immobilized. For the competition of the binding the indicated concentrations of the variations and of IgG Fc were employed. HBS-EP with a flow rate of 30 µl/min was used as the running buffer.
Figure 2B:
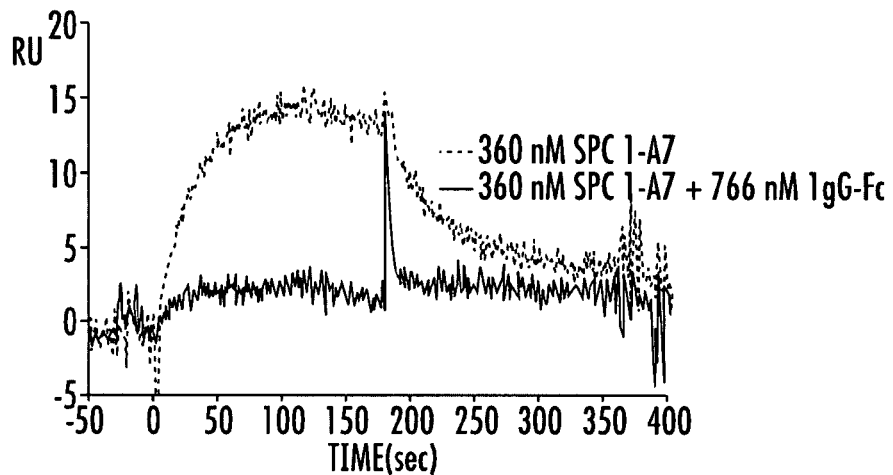
Figure 2C:
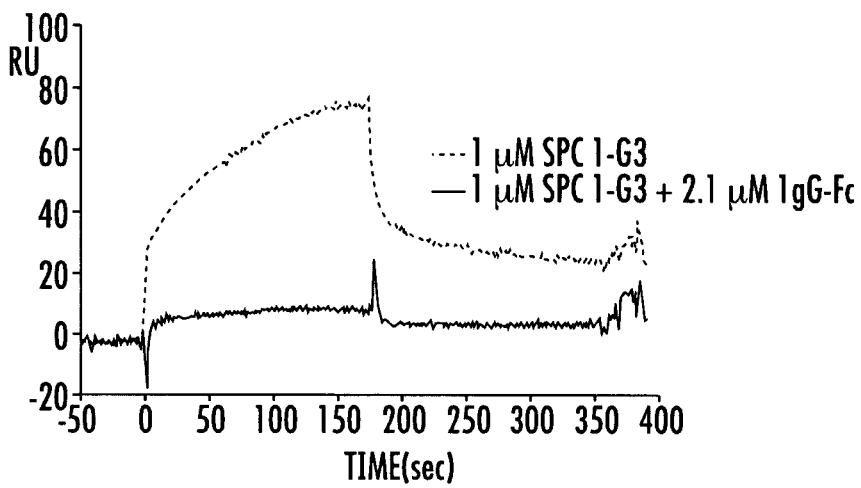

Using the ProSAII software ("Protein Structure Analysis"; Proceryon Biosciences, Salzburg) for example the protein stability in comparison to ubiquitin (WT) could be determined for $10^4$ variations and for an equal number of randomly taken samples of variations in which the residues of a "control epitope" (randomized positions 24, 28, 31, 32, 35, 37, 38, 39) were substituted. In this case about 19% of the variations generated in silico which were randomly substituted in the region of the binding site have a stability which is at least as high as that of ubiquitin (WT) while about 90% are more stable than those carrying the "control epitope" (FIG. 2). This computer-based result can then be used as a basis for the selection of suitable amino acids.

Starting with the available structural data of human ubiquitin, eight amino acid positions in the region of the binding site to be generated were preferably selected first. By means of random alterations of the primary sequence in this region (random mutagenesis) and subsequent specific selection those variations were obtained which showed the desired binding activity with respect to a predetermined hapten or antigen or generally to a predetermined binding partner, respectively. Although in this manner a de novo binding property is conferred to the resulting modified proteins their structure and protein-chemical properties remain to a high degree identical to those of the starting protein. Therefore, they exert advantages such as e.g. small size, high stability, cost-effective preparation as well as easy modification together with high affinity and specificity for a previously defined ligand. In this respect, the suitability of ubiquitin as a scaffold structure for the generation of artificial binding proteins could not be expected since 1) the tolerance of the scaffold with respect to the extensive amino acid substitutions could not be expected because of the small size of ubiquitin and 2) the functionality of the artificial binding site involving the beta sheet which is considered as rigid and inflexible did not seem possible beforehand.

Alternatively, polypeptide molecules based on gamma-crystallin are used according to the invention.

As mentioned in the beginning, gamma-crystallins, a class of crystallins in vertebrates, are monomeric proteins having a molecular mass of about 22 is kDa. The main structural motif of gamma-crystallins is the antiparallel beta sheet (Hazes and Hol, 1992, Richardson et al., 1992, Hemmingsen et al., 1994). Gamma-crystallins consist of two very similar globular domains, one N- and one C-terminal domain linked to each other by a V-shaped linker peptide. The folding pattern characteristic for gamma-crystallins ("Greek Key" motif, Slingsby, 1985, Wistow and Piatigorsky, 1988) is most likely the reason for the substantial thermostability as well as for the stability to denaturating agents (Mandal et al., 1987).

In its normal folded state, gamma-II-crystallin fails to show any binding properties. The alteration (mutagenesis) of a selected solvent-exposed region of this protein consisting of the beta sheet structural motif surprisingly resulted in an alteration of the surface structure and the charge pattern of the protein and thus to the generation of new binding properties. In this case, only regions or amino acid positions were selected which are not substantially involved in maintaining the structure of the protein. The mutagenesis of a small beta sheet protein (Riddle et al., 1997) has shown that a high percentage of proteins can form the native structure of the beta sheet despite substantial sequence alterations.

In the process described herein a targeted mutagenesis is performed on a protein lacking any binding properties in the rigid region of the beta sheet. In this way, a protein with substantial stability and with specific binding properties comparable to antibody molecules has been generated.

The phage display system serves as a suitable system for the isolation of mutagenized beta sheet proteins with newly generated binding properties. The system enables a very efficient screening of a large repertoire of protein variations for specific binding properties (Smith, 1985). For this purpose, each protein variation is prepared on the surface of a filamentous phage and can interact with the target molecules immobilized on a solid phase. Proteins binding to the target molecule can be obtained by elution of the phages. After isolation of the phage DNA the DNA sequence of the specifically binding protein variations can be determined. Besides the phage display system also other selection systems such as e.g. the bacterial display (Stahl and Uhlen, 1997) or the ribosomal display (Hanes et al., 1997) may find use.

By means of the procedure described it is surprisingly possible to alter the very stable beta sheet protein gamma-II-crystallin for example by means of a targeted site-specific mutagenesis in the beta sheet at the surface in a manner that the non-binding protein is changed into a protein having specific binding properties. Thus, by randomization of eight amino acid positions there is for the first time performed a mutagenesis in a scaffold molecule within a relatively rigid region of the protein. Therefore, "antibody-like" protein species—with respect to their specific binding properties—are prepared from the beta sheet protein gamma-II-crystallin. Gamma-II-crystallin or other small, stable beta sheet proteins can be generally used with the processes as described as novel scaffold molecules for the design of novel binding properties.

The modeled beta sheet proteins can be substituted for e.g. recombinant antibodies in different applications.

Other and more detailed information in this respect can be found in WO 01/04144 which is incorporated herein by reference in its entirety.

The term "ligand" as defined herein refers to a substance which is specifically bound by a polypeptide molecule based on gamma-crystallin or ubiquitin.

As this binding partner—the so-called ligand—all biochemically, biotechnologically, diagnostically and therapeutically relevant molecules can be employed. The list of possible ligands comprises several substance classes such as polypeptides and proteins (e.g. immunoglobulins and immunoglobulin derivatives, proteins which can be obtained from blood plasma, blood clotting factors and inhibitors, growth factors, interleukins, cytokines, receptor proteins, viral proteins and cell surface markers such as CD14, CD25, CD34), peptides (e.g. affinity tags such as S-Tag, T7-Tag, His-Tag, Strep-Tag, Myc-Tag, FLAG-Tag and peptides of viral origin), low molecular weight substances (e.g. steroids, cholesterol and noxious substances such as halogenated hydrocarbons), lipids (e.g. bacterial lipopolysaccharides, liposomes and lipoproteins), sugars (e.g. cell surface markers such as Lewis Y), nucleic acids (DNA, RNA) organic and inorganic polymers as well as derivatives of these substances. In this respect see also the preferred embodiments described herein below.

The term "functional component" as used herein defines the second component of the conjugate which covalently binds to the polypeptide molecule based on gamma-crystallin or ubiquitin. The term "functional" is intended to mean that it is a component suitable for use in diagnostics, therapy, chromatography and analytics and which possibly is already known. Generally spoken, a "functional component" is defined as any component with measurable properties, e.g. an enzyme activity, a spectroscopically measurable property or a toxic property. Apart from that, the structure and function of the functional component in the present conjugate is not limited. The only requirement is that after covalent binding of the polypeptide molecule and the functional component the functionality of all components is retained. In the case of the polypeptide molecule, this functionality is the binding capability to the specific ligand, in the case of the functional component it is for example its effect as dye.

According to the invention, one or even more, e.g. two, functional components can be bound to a polypeptide molecule (as defined above). To achieve specific binding of the components to the polypeptide molecule, for example, one of the components can be formed for specific binding to a lysine residue, the other can be formed for specific binding to a cysteine is residue in the polypeptide molecule. Examples of two components of this type are fluorescent dyes in which one serves as the fluorescence donor, the other as the fluorescence acceptor.

Details of the nature of the binding of the components to each other as well as of the binding components which are preferably used are described in the following.

The detection of the binding activity of the polypeptide molecules to the ligand and the activity of the coupling partner (functional component) is an important feature—as mentioned above. The detection of the binding activity to the ligand can be performed by different methods. In the ELISA technique the binding is detected by means of antibody-peroxidase conjugates whereas the Biacore system utilizes the surface plasmon resonance phenomenon for detection. Other techniques such as fluorescence titration, fluorescence polarization or fluorescence correlation spectroscopy (FCS) are based on the fluorophore properties of Affilin™. For the detection of the activity of the coupling partner, the so-called further functional component, the known properties thereof are of importance. Thus, chromophore or fluorophore molecules such as fluorescent dyes or phycoerythrin are analyzed by means of their spectral properties. Enzymes such as peroxidase or alkaline phosphatase are tested by their turnover of model substrates. Other molecules such as toxins can be tested for their biological activity directly in cell culture experiments. In the case of radioisotopes the radioactivity can be measured using appropriate counters. For a range of other molecules such as sugars and nucleic acids there are commercially available detection reagents.

According to one embodiment the binding property which is newly generated or altered compared to the wildtype polypeptide—as mentioned above—is based on one or more amino acid substitutions in a surface-exposed region of a β sheet of the polypeptide molecule (I). For this purpose, a number of about 6-10, preferably 8 amino acids per polypeptide molecule (I) is substituted. This applies equally to the polypeptide molecules (I) based on ubiquitin and on gamma-crystallin.

It shall be pointed out that the coupling of (I) to (II) is preferably carried out in a region outside of the surface-exposed region of the β sheet of the polypeptide molecule (I) intended for specific binding to a ligand. It has been found that in this manner an important requirement for the conjugate according to the invention, namely retaining of the functionality of all components, is achieved.

Here, coupling to Lys 29, 33 of ubiquitin which is localized outside of the binding surface for the ligand and more precisely even outside of the beta sheet which responsible for the binding to den ligand (Lys 29, 33 are localized in the alpha helix) is mentioned as an example. A coupling via this amino acid side chain which is spaced apart from the binding site to the ligand does not lead to an impairment of the functionality of the components of the conjugate.

In this view, it is particularly preferred to perform the coupling of (I) to (II) in a region outside of the β sheet of the polypeptide molecule (I) having the newly generated or altered binding property for specific binding to a ligand. In the case mentioned above, this region is e.g. the alpha helix of the ubiquitin molecule or, with respect to gamma-crystallin, the other of the beta sheets, i.e. the beta sheet not involved in the binding to the ligand. This is particularly clear from FIG. 1 in which the N-terminal domain (beta sheet) of crystallin has a newly generated binding surface for the ligand wherein the lysine residues localized in the C-terminal portion (highlighted) are suitable for coupling to the functional component (II).

According to an embodiment the coupling or linkage, respectively, of (I) to (II) occurs via amino acid residues of (I). In other words, a coupling is achieved here via amino acid residues which are present in the polypeptide molecule (I) per se.

In this case, the coupling is performed site-specifically or selectively in an undirected manner via cysteine or lysine side chains in (I). The term "site-specifically" means here that a cysteine or lysine is present or is introduced at a precisely defined site in the molecule (I) to define an exact predetermined binding site. "Selectively in an undirected manner" means that several of such residues are present so that due to their number binding to these residues, although it occurs selectively, is also subject to a certain random factor.

With respect to the coupling of the two components of the conjugate according to the invention, i.e. the covalent linkage thereof, the following explanations are given:

Proteins contain a plurality of functional groups by which the coupling to other molecules may be achieved. Distinct examples of these will be mentioned below. By covalent linkage of the partners, e.g. via a suitable cross-linking reagent, it is possible to combine different activities in one molecule. As an example antibodies are mentioned which are often coupled to dye molecules and in this manner have been found to provide easily detectable detection reagents that subsequently can be used in diagnostics.

In an analogous manner, antibodies are also conjugated with other proteins, preferably so-called reporter enzymes such as alkaline phosphatase or peroxidase. These reporter enzymes convert a substrate whereby a signal is obtained which can be detected by absorption, fluorescence or luminescence.

By the selection of suitable cross-linking reagents proteins, i.e. also the polypeptide molecules according to the invention, can also be coupled to other functional components from many other substance classes: A plurality of organic and also inorganic polymers, proteins, peptides, nucleic acids, lipids, sugars and also low molecular weight substances can be used for this purpose. Preferred coupling partners from the class of polymers are e.g. dextrane, polymethacrylate, sepharose, agarose, polystyrene, polyvinyl, silica gel, cellulose or polyethylene glycol (PEG). The latter modification is for example used for the modulation of the pharmacokinetic properties of biotherapeutics. A large selection of PEG derivatives having functional groups which are suitable and already pre-activated for coupling are commercially available (Nektar Therapeutics). The other polymeric materials mentioned serve as carrier substances in many biochemical, biotechnological and diagnostic processes. Particular mention shall be made here e.g. of chromatographic applications, particularly affinity chromatography, where these polymeric substances find use as gel matrix. For this purpose the surface of polymer beads carrying suitable chemical groups is functionalized and activated to enable the coupling, e.g. of a protein, with a desired activity. In this manner, also binding proteins with a specificity for a particular ligand can be immobilized and the resulting gel matrix can then be used for efficient and rapid enrichment of the ligand from a complex substance mixture. This enrichment can be performed either by column chromatography or also on the surface of filters. Furthermore, also those polymeric beads which have magnetic properties (magnetic BEADS) and thus can be efficiently separated from a mixture can be advantageously used for affinity enrichment.

An important example is the large-scale purification of antibodies for therapeutic purposes from the supernatant of eukaryotic cells which is performed by affinity chromatography to matrix-coupled protein A, a bacterial protein with an intrinsic affinity for antibody molecules.

There are many examples besides the antibody-reporter enzyme fusions mentioned above for the coupling of two protein components. Thus, in one of is the easiest cases homodimers or -multimers can be generated by the coupling of two or more identical protein molecules.

In the case of binding proteins, avidity effects can be achieved by multimerization, i.e. the affinity of the multimers for the target substance is significantly increased compared to the affinity of the monomeric binding protein. By coupling two binding proteins with specificities for different target substances, however, so-called bispecific binding molecules can be obtained which can e.g. be used as an adapter to bring the respective target substances in spatial proximity to each other.

Also proteins having toxic properties for living cells, so-called toxins (e.g. ricin, choleratoxin, *Pseudomonas* exotoxin among others) represent interesting coupling partners for antibodies or other binding molecules. Following coupling, this bifunctional conjugate can selectively dock at a specific target substance, e.g. on the surface of a tumor cell, via the binding protein and afterwards the targeted cell will be destroyed by the cytotoxic activity.

Other relevant coupling partners of protein nature are protein chromophores such as e.g. GFP and derivatives or pigment-containing proteins such as phycoerythrins. Being well detectable reporter substances, the resulting chromophoric or fluorescent coupling products themselves are valuable tools for research or diagnostics.

However, as already mentioned above chromophoric or fluorescent protein conjugates are also available by the coupling of low molecular weight dye molecules. A plurality of suitable dye molecules with cross-linking groups is commercially available e.g. from Invitrogen company. Other low molecular weight coupling partners yielding protein conjugates for the use in diagnostics and therapy are e.g. biotin, digoxigenin, heavy metal derivatives, chelating agents, radioisotopes, cytotoxic substances and antibiotics.

The functional groups contained in proteins and also in the polypeptide molecules according to the invention as well as in functional components suitable for coupling predominantly are amino, carboxy, hydroxy and sulfhydryl groups but also the phenol function of tyrosine and the aromatic ring systems can serve as sites for the attack of coupling reagents. Amino acid residues suitable for coupling are characterized by specific properties: On the one hand they must have a reactive side chain accessible to the coupling reagent. In an ideal case, this functional group is localized at the protein surface and is exposed to the solvent. Furthermore, the modification of this residue should not interfere with the function of the protein. Preferably, the residues to be modified are in a significant distance from the active site of an enzyme or from the binding surface of the polypeptide molecule according to the invention; furthermore, these regions should also be void of amino acid residues of the same type which after modification could result in a loss of function of the protein. Advantageous are therefore also amino acid residues which are rare in the respective protein.

As already mentioned above, for the polypeptide molecule (I) based on ubiquitin a coupling via lysine residues 29 and 33 of the ubiquitin molecule is preferably considered. A bit less preferably, but still possible is coupling via lysine residues 11 and 48 which are both localized at a shorter distance to the binding surface to the ligand than the residues 29 and 33.

In the case of the polypeptide molecules (I) based on gamma-crystallin the peptide domain with the binding property for specific binding to a ligand which is newly generated or altered as compared to the wildtype polypeptide is the N-terminal domain and the coupling of (I) to (II) is performed via the C-terminal domain. This also applies to the possibility of a C-terminal peptide fusion which preferably contains cysteine and also for amino acid side chains such as lysine which are present in the C-terminal domain and available for coupling to the functional component. Residues 91 and 163 of is gamma-crystallin are preferably used (see FIG. 1).

Among the proteinogenic amino acids there must be primarily pointed out lysine having an epsilon amino group in its side chain as well as cysteine with its sulfhydryl function. These functional groups are particularly reactive and therefore well suited as partners for a specific coupling of a polypeptide molecule according to the invention to a functional component. Thus, reagents are described in the literature which specifically react only with sulfhydryl groups and therefore can be used according to the invention, e.g. maleinimide, iodoacetate, hydroxymercuribenzoate, Ellman's reagent among others. Further examples can be found in respective text books such as Voet & Voet (1995) or Lottspeich & Zorbas (1998).

These describe also numerous lysine-specific side chain reagents such as e.g. acid anhydrides (acetic anhydrid, N-hydroxysuccinimide among others which find also use in the present invention). Besides their reactivity, lysines have other advantageous properties for coupling: Because the side chain is charged it is mostly localized at the surface of the protein, i.e. accessible to the solvent which in biologic systems is primarily water. This accessibility is also required for the coupling reagent and thus should be present.

Free cysteines exposed to the surface are relatively rare in proteins, in extracellular proteins these cysteines are mostly involved in disulfide bonds which often also stabilize dimeric interactions. However, disulfide bonds can be cleaved by reduction so that the cysteines contained are rendered accessible to modification. If a polypeptide molecule according to the invention does not contain cysteine residues accessible to a coupling reagent it is possible to introduce such residues at a suitable site by mutagenesis. In this respect, knowledge of the spatial structure of the protein is of advantage since this facilitates a prediction of the surface-exposed amino acid positions suitable for coupling. However, if several cysteine residues are present in a protein which makes a site-specific is coupling (to a defined cysteine residue, see above) impossible these can be eliminated by means of site-directed mutagenesis. In this case, a substitution by a serine residue having similar properties to the cysteine residue is preferred.

However, it is often impossible to obtain suitable amino acid residues for coupling by mutagenesis in the protein sequence of interest. If the protein tolerates insertions of amino acid residues or fusions at the N- or C-terminus peptide sequences which contain amino acid residues suitable for coupling can be introduced at these sites on the genetic level.

Therefore, according to another embodiment the coupling of (I) to (II) is carried out via amino acid residues in an additional terminal peptide fusion to (I).

An examination of the accessibility of these terminal peptide fusions can be performed e.g. by using a side chain-specific coupling reagent with chromophore properties, e.g. Ellmann's reagent for cysteine (see also the examples). Among others, the accessibility of these terminal peptide fusions can be regulated by their length. An increase in the accessibility of the amino acid side chain to be coupled is possible e.g. by the insertion of so-called spacers between the amino acid side chain to be coupled and the protein, in the case of peptide fusions these are additional, inert amino acid residues. Particularly suitable are glycine and serine residues since they are of a small size and thus can assume a very flexible structure.

Depending on the number of functional groups in the protein which are accessible to the coupling reagent and its specificity different types of coupling can be distinguished. For example, if a cysteine-specific coupling reagent is used only cysteine residues will react selectively; however, if e.g. several cysteine residues are present the precise site of coupling cannot be predetermined; this is called a selective, but undirected coupling. If, however, only one cysteine exists which is accessible to the coupling reagent the coupling occurs site-specifically.

A plurality of suitable coupling reagents is commercially available (e.g. from Pierce company). A specific form of coupling reagents which can be used according to the invention is referred to a cross-linker or simply as linker (Herrmann & Morse, 1973; Takamiya et al., 1975; Reichlin, 1980).

A linker is defined as a substance linking two (or more) molecules by a covalent bond. Linkers contain two (or more) reactive (activated) functional groups the spatial distance of which can be regulated by further chemical groups linking them. Linker having identical functional groups are referred to as homo-bifunctional in contrast to hetero-bifunctional linkers having different functional groups. Therefore, by suitable selection of linker substances it is also possible to link completely different substance classes to each other.

As an example of a linker which can be employed according to the invention reference is made to the C-terminal portion of SPC-1-A7-Cys, see Table 2 below.

A specific case of the coupling of proteins, however, does not require activated linkers: the formation of disulfide bonds e.g. in the dimerization of proteins. Under oxidizing conditions sulfhydryl residues have a reactivity which is sufficiently high to form a disulfide, i.e. a covalent bond between the two sulfur atoms.

A coupling reaction can proceed according to the invention either as a one-step reaction or also in several steps. In the case of a simple dimerization of two identical molecules each having only one reactive residue it is sufficient to incubate the coupling components with a homo-bifunctional linker to obtain a defined conjugate. In the case of different coupling partners also carrying different reactive groups the one-step reaction is only possible with an appropriate hetero-bifunctional linker.

Alternatively, the coupling between different coupling partners (reactants) with identical reactive groups can also proceed in a multi-step process. For this purpose, at first only one reaction partner is incubated in most cases with an excess of the linker, and the resulting monovalent reactant-linker conjugate is isolated before it is linked to the second reactant via the remaining free functional group of the linker. A plurality of chemical substances finding use in biochemistry and biotechnology are commercially available in a so-called activated form, i.e. already linked to a still reactive linker (Pierce company, Invitrogen company).

The degree of coupling, i.e. the relative ratio of the individual components in the conjugate can be regulated to a certain extent by the stoichiometry of the reactants employed if more than one reactive group is present. A defined multiple coupling with different coupling partners is possible by sequential coupling or by the use of different coupling chemistries, e.g. by coupling of the first functional component to cysteine, while the functional component 2 is attached to lysines of the respective polypeptide. A typical example is attaching of fluorescence donor/acceptor pairs for FRET measurements. Combinations of dye molecules suitable for this purpose are available from Invitrogen company.

Independent of the coupling mechanism selected which results in the conjugate according to the invention it shall be again be pointed out that the functional capability of the present conjugates was unexpected and surprising. Accordingly, reference is made also to what is explained herein above.

Moreover, it shall be mentioned that it was unexpected for those skilled in the art that conjugates as disclosed in the present invention can be generated while the full functionality of the individual components is retained or even enhanced.

The size ratios between the polypeptide molecules according to the invention on the one hand and the functional components on the other hand are very different. Sometimes the molecules to be bound, for example phycoerythrin, are 10-12 times larger than the polypeptide molecules, but sometimes also small such as the fluorescent dye Oyster. Surprisingly, both the structure of the polypeptide molecules and also the binding affinity to the ligand are retained, in particular in the much larger molecules bound. This could not be expected in this way.

As already explained above the side chains for the coupling to the functional component are preferably localized outside of the binding surface of (I) to the ligand so that the functionality of binding to the ligand is not impaired.

According to another preferred embodiment the terminal peptide fusion to (I) contains—as mentioned above—one or more cysteine residues or one or more lysine residues wherein these amino acid residues preferably are not involved in the interaction of (I) with the ligand.

The functional component (II) is preferably selected from the group consisting of polypeptides and proteins, organic and inorganic polymers, nucleic acids, lipids, sugars, low molecular weight substances, peptides as well as derivatives of these substances. With respect to the principles of binding and coupling reagents see also the explanations above.

According to a preferred embodiment the functional component (II) is a peptide, polypeptide or a protein, preferably a protein chromophore, an enzyme, an immunoglobulin, an immunoglobulin derivative, a toxin or a polypeptide according to I.

If the functional component (II) is a polymer it is preferably selected from dextrane, polymethacrylate, sepharose, agarose, polyvinyl, polystyrene, silica gel, cellulose or polyethylene glycol, or a polymer derivative.

If the functional component (II) is a low molecular weight substance this is preferably a dye, biotin, digoxigenin, a heavy metal, a chelating agent, a radioisotope, an antibiotic or a cytotoxic substance.

According to a preferred embodiment the ligand which specifically binds to component (I) is preferably selected from the group consisting of polypeptides, peptides, low molecular weight substances, lipids, sugars, nucleic acids, organic and inorganic polymers as well as derivatives of these substances.

If this ligand is a polypeptide or a protein, immunoglobulins and immunoglobulin derivatives, proteins obtained from blood plasma, blood clotting factors and inhibitors, growth factors, interleukins, cytokins, receptor proteins, viral proteins and cell surface markers, preferably CD14, CD25, CD34, are preferably employed.

If the ligand is a peptide it is preferably an affinity tag, preferably S-Tag, T7-Tag, His-Tag, Strep-Tag, Myc-Tag, or FLAG-Tag, or a peptide of viral origin.

The ligand can also be a low molecular weight substance, preferably steroids, cholesterol and noxious substances such as for example halogenated hydrocarbons or a lipid or lipid derivative, preferably bacterial lipopolysaccharides, liposomes and lipoproteins.

According to a preferred embodiment the component (II) of the conjugate according to the invention is one or more polypeptides based on gamma-crystallin or ubiquitin which is identical to (I) and covalently linked thereto whereby an increase in the affinity to the ligand of (I) is achieved by means of avidity effects. For a detailed explanation see the description above.

Furthermore, component (II) preferably is a polypeptide, protein or polymer to which component (I) is covalently linked in a multiple manner whereby an increase in the affinity to the ligand of (I) is achieved by means of avidity effects. Alternatively, component (II) is a polypeptide or polymer which after covalent linkage to component (I) undergoes covalent or non-covalent binding to other conjugates of this type whereby an increase in the affinity to the ligand of (I) is achieved by means of avidity effects.

According to a preferred embodiment component (I) is one of the molecules SPC1-A1 (SEQ ID NO: 2), SPC1-A7 (SEQ ID NO: 3), SPU11-3-A1 (SEQ ID NO: 12 and 13), SPC1-G3 (SEQ ID NO: 4), and SPC7-E9 (SEQ ID NO: 8).

However, the invention not only comprises the exact nucleic acid sequences but also variations thereof. "Variations" according to the invention are particularly such nucleic acids which one or more substitutions, insertions and/or deletions are present in comparison to the nucleic acids defined in the SEQ ID NO. In these variations preferably at least 1 but also 2, 3, 4 or more nucleotides are deleted on one or both ends of the nucleic acids or also in the inner portion of the nucleic acids or are replaced by other nucleotides.

Thus, the nucleic acids of the present invention also comprise nucleic acids having sequences which are substantially equivalent to the nucleic acids of the respective SEQ ID NO. Nucleic acids according to the invention can have e.g. at least about 80%, typically at least about 90% or 95% sequence identity to the nucleic acids of the SEQ ID NO.

The term "nucleic acid sequence" relates to a heteropolymer of nucleotides or to the sequence of these nucleotides. The term "nucleic acid" as used herein comprises both RNA, DNA, including cDNA, genomic DNA and synthetic (for example chemically synthesized) bases as well as also bases bound to other polymers such as PNA.

The invention comprises also such variations which hybridize to the nucleic acids according to the invention under moderately stringent conditions.

Stringent hybridization and washing conditions generally refers to the reaction conditions under which only duplex molecules between oligonucleotides and desired target molecules (perfect hybrids) are formed or only the desired target organism is detected. Stringent hybridization conditions in this respect particularly means 0.2×SSC (0.03 M NaCl, 0.003 M sodium citrate, pH 7) at 65° C. In the case of shorter fragments, for example oligonucleotides of up to 20 nucleotides, the hybridization temperature is below 65° C., for example higher than 55° C., preferably higher than 60° C., but in any case below 65° C. Stringent hybridization temperatures are dependent on the size or length, respectively, of the nucleic acid and on their nucleotide compositions and can be determined by those skilled in the art by manual experimentation. Moderately stringent conditions are for example achieved at 42° C. and by washing in 0.2×SSC/0.1% SDS at 42° C.

The respective temperature conditions can be different depending on the selected experimental conditions and dependent on the nucleic acid sample to be examined and in this case must be adjusted appropriately. The detection of the hybridization product can be performed for example by autoradiography in the case of radiolabeled molecules or by fluorimetry if fluorescence-labeled molecules are employed.

Those skilled in the art can adapt the conditions to the method of examination selected in a manner known per se to actually achieve moderately stringent conditions and enable a specific method of detection. Suitable stringency conditions can be determined for example by means of reference hybridizations. A suitable nucleic acid or oligonucleotide concentration must be employed. The hybridization must take place at a suitable temperature (the higher the temperature the weaker the binding of the hybrids).

According to a second aspect the present invention relates to a method for the preparation of a conjugate as defined above starting with component (I) having a known sequence which comprises the following steps:

Identification of suitable amino acid residues for coupling by analysis of the spatial structure of the protein, preferably of residues outside of the surface of interaction of (I) with the ligand;
activation of a coupling partner by a suitable coupling reagent;
performing the coupling reaction;
isolation of the conjugate; and
detection of the functionality of both components of the conjugate.

A modified process for the preparation of a conjugate of the invention—starting with component (I) having a known sequence in which no amino acid residues suitable for coupling were identified—comprises the following steps:

Introduction of amino acid residues suitable for coupling by substitution, insertion or fusion, preferably of residues exposed to the surface outside of the surface of interaction of (I) with the ligand;
detection of the accessibility of the amino acid residues introduced;
detection of the functionality of the components (I) altered in this manner;
activation of a coupling partner by a suitable coupling reagent;
performing the coupling reaction;
isolation of the conjugate; and
detection of the functionality of both components of the conjugate.

For a more detailed explanation of the coupling methods etc. see above.

According to a third aspect the present invention provides a conjugate which can be prepared according to the processes mentioned above.

Furthermore, the present invention comprises a diagnostic kit containing a conjugate as defined above.

Another aspect of the present invention is a pharmaceutical composition comprising a conjugate according to the invention and a pharmaceutically acceptable carrier.

In the pharmaceutical composition the conjugate is admixed with suitable carriers or carrier substances in such doses that the disease is treated or at least alleviated. A composition of this type can contain (in addition to the active agents and the carrier) diluting agents, filling materials, salts, buffers, stabilizers, solubilizing agents and other materials well known in the state of art. The term "pharmaceutically acceptable" defines a non-toxic material which does not impair the effectiveness of the biologic activity of the active ingredient or active agent, respectively. The selection of the carriers depends on the route of administration.

The pharmaceutical composition can additionally contain other agents enhancing the activity of the active agent or supplementing the activity or use thereof in the treatment. Such additional factors and/or agents can be contained in the pharmaceutical composition to achieve a synergistic effect or to minimize side effects or adverse effects, respectively.

Techniques for the formulation and preparation, respectively, and the administration of the conjugates of the present application can be found in "Remington's Pharmaceutical Sciences", Mack Publishing Co., Easton, Pa., latest edition. A therapeutically effective amount furthermore relates to an amount of the compound which is sufficient to achieve an improvement of the symptoms, for example a treatment, cure, prevention or improvement of such conditions. Suitable routes of administration can include for example oral, rectal, transmucosal or intestinal administration and parenteral administration, including intramuscular, subcutaneous, intramedullar injections and also intrathekal, direct intraventricular, intravenous, intraperitoneal or intranasal injections. Intravenous administration to a patient is preferred.

According to another aspect the present invention relates to the use of a conjugate as defined herein, of kits or composition in diagnostics, therapy and affinity chromatography.

The coupling methods presented and the data obtained therewith enable various applications of the conjugates including the use of the conjugates in affinity chromatography. Examples for this use is the replacement of protein A for the purification of antibodies and the purification of blood plasma proteins, growth factors or influenza vaccines by means of affinity chromatography as well as the purification of proteins prepared by genetic engineering with affinity tags or the depletion of endotoxins and albumins, respectively. Furthermore, by coupling to matrices a use in blood plasmapheresis or bioremediation can be considered.

Another field of use is in diagnostics. In this respect, the use in the screening of blood banks for bacterial or viral infections or in classical detection techniques such as ELISA or new developments such as in a Luminex system can be considered. In diagnostics, but also in therapy, such conjugates can be employed in the separation of cells.

The use of the conjugates according to the invention in therapy is also possible, particularly the general use as transport molecules. Other applications in therapy would be in gene therapy in the directed targeting by a polypeptide molecule according to the invention and the coupling to systems for gene transfer. By directed targeting and coupling to a bacterial toxin the use as an immunotoxin in therapy would be obtained as well.

In the following, the present invention will be explained with respect to several Figures and the accompanying Examples which however are not intended to limit the scope of the invention but merely shall illustrate the invention.

Example 1

Selection of Affilin™ Variations Binding to IgG Fc and proNGF from the Human Gamma-II-Crystallin Library, Expression and Purification Starting with the human gamma-crystallin library CR20 a selection process was carried out by means of the phage display system. Even after the first round several Affilin™ variations could selected and isolated which showed specific binding to IgG Fc in the single phage ELISA. It should be noted that the term "Affilin™" as used herein corresponds to the polypeptide molecule component according to the invention of the conjugate which is based on ubiquitin or gamma-crystallin and has an altered binding property for specific binding to a ligand compared to the wildtype. Following cloning of the genes into the pET20b expression vector (Novagen) the Affilin™ variations were overexpressed in E. coli (BL21(DE3), Stratagene) in a recombinant manner and subsequently purified in two chromatographic steps (IMAC and gel filtration). In a protein concentration-dependent ELISA and in BIACORE experiments a specific binding to IgG Fc with a dissociation constant in the nM range could be determined.

For the selection of Affilin™ variations binding to IgG Fc 1 ml of the CR20 library ($6.5 \times 10^{10}$ cfu) was incubated in 1 l of 2×YT medium with 2% glucose and 100 µg/ml ampicillin at 37° C. and 220 rpm up to an optical density of $OD_{600}$=0.4. Afterwards, the bacterial culture was incubated with a 10-fold excess of the helper phage M13KO7 (Invitrogen, Karlsruhe, Germany) for infection for 1 h at 37° C. and 100 rpm. The bacterial suspension was then centrifuged for 20 min at 1000×g and the pellet was resuspended in 1 l of 2×YT medium with 8 mM GSH, 100 µg/ml ampicillin and 50 µg/ml kanamycin. The phage production or phage release, respectively, was carried out at 30° C. and 200 rpm over night. For the isolation of the phages the protocol described by Kay, Winter & McCafferty (1996) was used.

1 ml of the isolated phages ($1.4 \times 10^{14}$ cfu) were blocked with 1 ml 6% BSA in PBS for 1 h at room temperature (RT). Meanwhile, 10 wells of a microtiter plate (NUNC) coated over night at RT with 100 µl of a 10 µg/ml solution of monoclonal IgG Fc (Roche) in PBS were washed three times with PBS; 0.1% Tween 20. Afterwards, free binding sites in each of the wells were blocked with 300 µl PBS (3% BSA, 0.5% Tween 20) for 2 h at RT followed by washing of the wells three times with PBS (0.1% Tween 20). After an addition of 100 µl of the blocked phage per well an incubation for 1 h at RT and 20 rpm was carried out. Unbound and weakly bound phage, respectively, were removed by washing twice with 2×PBS, twice with 2×PBS, 3% BSA and finally 2× with 2×PBS. The still bound phages were eluted by the addition of 100 µl/well 100 mM triethylamine and incubation for 10 min at RT. For the neutralization of the phages eluted in basic medium these (a total of 1 ml) were added with 500 µl of 1 M Tris/HCl pH 7.4. Subsequently the wells were washed three times with PBS.

Tightly bound phage which remained in the microtiter plate despite the elution with triethylamine were directly incubated for re-infection with 100 µl of an exponentially growing cell culture ($OD_{600}$=0.4) of XL1-Blue for 30 min at 37° C. For the re-infection of XL1-Blue cells with the phages eluted in basic medium 750 µl of the neutralized eluate were incubated for 30 min at 37° C. with 9 ml of XL1-Blue cells having an $OD_{600}$=0.4. Afterwards, the re-infected cells of phages eluted in basic medium and of tightly bound phages were combined, plated onto 16×16 cm plates containing SOBAG medium (including ampicillin) and incubated over night at 37° C. After a panning process approx. 2000 clones were obtained which were floated off the plates with about 12.5 ml of 2×YT medium; 20% glycerol and stored at −80° C.

For the cultivation of single phages the cell pool obtained after the first round of panning was plated on selection medium (SOBAG) and incubated over night at 37° C. From the SOBAG plate 92 single clones were transferred into 24×5 ml deep well plates each containing 2 ml/well of 2×YT medium with 2% glucose and 100 µg/ml of amp and incubated over night at 37° C. and 180 rpm. In addition, one single colony (XI1-blue) per plate containing the gene for the human wildtype gamma-crystallin in the phagemid vector was used as a control. Sterile 24×5 ml deep well plates containing 2.5 ml/well of 2×YT medium with 2% glucose and 100 µg/ml amp were each inoculated with 1% of inoculum of the over-night culture and the bacterial cultures were incubated at 37° C. and 180 rpm up to an $OD_{600}$ of approx. 0.4. Afterwards, the cultures were infected with 2.5 µl per well of helper phage M13K07 with $10^{13}$ cfu/ml and incubated for 1 h at 37° C. and 100 rpm whereafter the bacteria were pelleted by centrifugation, the supernatant was discarded and the pellets were resuspended in 2.5 ml per well of 2×YT medium, 8 mM GSH, 100 µg/ml ampicillin, 50 µg/ml kanamycin and incubated over night at 30° C. and 200 rpm. To obtain the phage supernatant a centrifugation of the plates at 4600 rpm was carried out. Precipitation and pelleting of the phages were carried out as described in Kay, Winter & McCafferty, and the phage pellet was resuspended in approx. 200 µl PBS, 3% BSA, pH 7.4. By this procedure the phages could be concentrated and subsequently employed in an ELISA.

For this purpose, the wells of a NUNC plate were coated with 100 µl of antigen solution (10 µg/ml of human monoclonal IgG Fc or BSA, respectively) over night at 4° C. On the next day, the ELISA plate was incubated with blocking buffer (PBS, 3% BSA, 0.5% Tween 20, pH 7.4) for 2 h at room temperature. After washing of the wells with washing buffer (PBS, 0.1% Tween 20, pH 7.4) 100 µl each of the blocked phage preparations were added to the wells and incubated for 1 h at RT. After another washing of the wells with washing buffer (PBS, 0.1% Tween 20, pH 7.4) the monoclonal anti-M13 antibody (POD-conjugated; MoBiTec, Gottingen) was applied in a dilution of 1:5000 in PBS, pH 7.4 (100 µl/well) and again incubated for 1 h at RT. Afterwards the wells were washed 3× with washing buffer (PBS, 0.1% Tween 20, pH 7.4) and 3×PBS and the color reaction with TMB Plus (Kementec, DK) was initiated (100 µl/well). After 20 minutes the color reaction was stopped by the addition of 0.2 M $H_2SO_4$. The yellow color obtained was read at 450 nm (reference wavelength: 620 nm) and noted.

From those phage preparations which showed a clear signal with respect to the binding to monoclonal IgG Fc and a hardly detectable binding to BSA the genes of the gamma-II-crystallin variations were sequenced using the primer pCAN700. Three clones resulting therefrom, SPC1-A1, SPC1-A7 and SPC1-G3, were subcloned into the pET20b expression vector using the restriction sites NcoI and BstEII and introduced into the expression strain BL21(DE3), pUBS520 (Stratagene).

The cells were cultured in 2×YT medium with 100 µg/ml ampicillin and 50 µg/ml kanamycin up to an optical density of $OD_{600}$=0.6-0.8 at 37° C. and 200 rpm, and subsequently the recombinant protein expression was induced with IPTG (1 mM final concentration). After growth for four hours at 30° C. and 200 rpm the cells were harvested by centrifugation (6000×g, 20 min, 4° C.). The cell disruption was carried out in NPI-10 buffer (Qiagen) by means of lysozyme (0.1 mg/ml) and sonication (6×15 sec, under cooling with ice) in the presence of 5 mM of beta-mercaptoethanol. After centrifugation (40.000×g, 30 min, 4° C.) the supernatant was applied to an IMAC column (HiTrap Chelating HP, Amersham Bioscience) and washed with NPI-20 (Quiagen, +5 mM beta-mercaptoethanol) (20 column volumes). The elution was carried out by a linear gradient with NPI-500 (Quiagen, +5 mM beta-mercaptoethanol) in 30 column volumes. The fractions containing gamma-II-crystallin were analyzed by means of SDS PAGE, the respective samples were pooled and applied to a gel filtration column (1.6×60, Sephadex 75, Amersham Biosciences). PBS, at a flowrate of 0.75 ml/min, served as the running buffer. The analysis of the gel filtration was carried out by means of SDS PAGE, the fractions containing gamma-II-crystallin were combined and stored at 4° C. After this purification procedure the Affilin™ variations had a purity of >95% (SDS PAGE).

The binding properties of the purified proteins were now tested as described above in a concentration-dependent ELISA. For this purpose, different concentrations (100 nM-10 µM) of the Affilin™ variations were employed and an anti-gamma-II-crystallin antibody (monoclonal antibody conjugate with POD) was employed as the detection antibody. It was found that all three Affilin™ variations tested show specific binding to human IgG Fc and that unspecific binding to BSA or to the microtiter plate was not detectable. The human wildtype gamma-II-crystallin used as the control showed no binding to IgG Fc, BSA, or the microtiter plate.

In BIACORE experiments the dissociation constants of the three Affilin™ variations were determined. For this purpose, approx. 180 RU of human IgG Fc (50 µg/ml in 50 mM Na citrate, pH 5.0) was immobilized on a CM5 chip. Free binding sites were finally inactivated by 1 M ethanolamin (pH 8.5).

Then, at a flow of 30 µl/min, 6 different concentrations (166 nM-1 µM) were passed over the chip for 180 sec. Afterwards, at the same flow the chip was rinsed with HBS, 0.005% Surfactant P20 (Biacore) for 180 sec. From the resulting sensorgrams using the BiaEvaluation Software (Biacore, Uppsala, Sweden) the following dissociation constants of the Affilin™ variations to IgG Fc could be determined: SPC1-A1 with 230 nM, SPC1-A7 with 280 nM and SPC1-G3 with 800 nM. In competition experiments the specific binding of the Affilin™ variations to IgG Fc and not to the chip matrix could be detected (FIG. 2).

Figure 3:
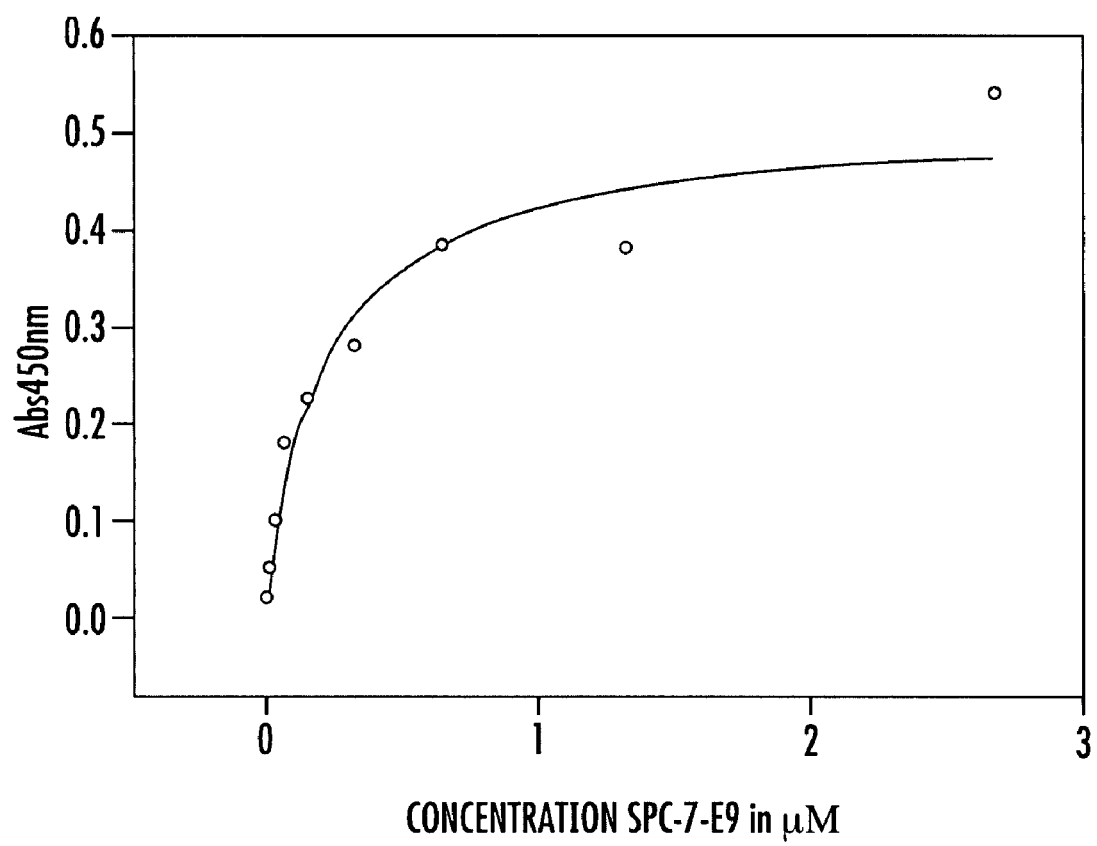
FIG. 3: Concentration-dependent ELISA for the detection of the binding of SPC7-E9 to proNGF. The microtiter plate was coated with 10 µg/ml of proNGF. As the detection antibody served an anti-human gamma-II-crystallin antibody-POD conjugate in a dilution of 1:1000. The absorption values presented are mean values of two parallel measurements. An apparent $K_D$ value of 200 nM could be calculated.

In a manner analogous to the selection of the variations SPC1-A1, SPC1-A7 and SPC1-G3 the Affilin™ variation SPC7-E9 which is directed against the target molecule proNGF was isolated. The dissociation constant could be determined by means of BIACORE-Messungen to 1-6 nM (FIG. 3).

Example 2

Selection of Affilin™ Variations from the Human Ubiquitin Library (U810) Against a Cysteine Knot Protein—Expression and Purification Provision of a Synthetic Ubiquitin Gene for the Selection of Modified Proteins Having a Newly Generated Binding Affinity Genetic engineering work was performed according to standard protocols known to those skilled in the art such as e.g. those of Sambrook et al. (1989).

For the preparation of the DNA sequence (Seq ID No. 2) for a modified ubiquitin protein scaffold having the substitutions Ile44Ala, Lys48Arg, Arg54Leu, Val70Ala, Arg72Leu, Gly75Ala as well as the deletion of Gly76 as a starting point for the preparation of artificial binding proteins the procedure was as follows: for gene synthesis a PCR reaction was performed in a 3.0 volume of 50 µl in which 2.5 µl each of the six oligodeoxynucleotides (Seq ID No. 26, Seq ID No. 27, Seq ID No. 28, Seq ID No. 29, Seq ID No. 30, Seq ID No. 31; 0.1 µM each) representing together in their base pair sequence the gene to be synthesized were present as templates. The sequences of the oligodeoxynucleotides employed each corresponded to segments of the is coding and the non-coding DNA strand, respectively, of the artificial gene with a length of 40 to 50 base pairs alternatingly overlapping at their 3' and 5' ends by approx. 15 bases. In addition, the sample contained 2.5 µl each of flanking primers (Seq ID No. 32, Seq ID No. 33; 10 µM) as well as 5 µl of 10×Taq buffer (100 mM Tris/HCl pH 9.0, 500 mM KCl, 1% (v/v) Triton X-100), 3 µl 25 mM $MgCl_2$, and 4 µl dNTP mix (2.5 mM each of dATP, dCTP, dGTP, dTTP). After filling up with $H_2O$ the reaction sample was heated in the thermocycler for 2 min to 94° C. for denaturation. Then, 2.5 U of Taq polymerase (Promega) were added during heating (hot start) and the PCR program was started. Incubation was performed for 25 cycles each for 1 min at 94° C., 1 min at 55° C., and for 1.5 min at 72° C. A final incubation was carried out for 5 min at 72° C.

The desired PCR product was identified by means of analytical agarose gel electrophoresis and purified from the sample using the MinElute Reaction Cleanup kit (Qiagen). 1.0 ng of the isolated DNA were used as a template for a second amplification which was carried out this time using Pfu polymerase (Promega) also in a volume of 50 µl. For this purpose, 5 µl of the supplied 10×Pfu buffer (200 mM Tris/

HCl, pH 8.8, 20 mM MgCl$_2$, 100 mM KCl, 100 mM (NH$_4$)$_2$SO$_4$, 1% (v/v) Triton X-100, 1 mg/ml BSA) as well as 4 µl dNTP mix were used and filled up with H$_2$O. In addition, the sample contained flanking primers (Seq ID No. 32, Seq ID No. 33; 10 µM) for the introduction of suitable restriction sites. The desired PCR product was isolated by means of preparative agarose gel electrophoresis and was inserted into the cloning vector pCR®4Blunt-TOPO® using the Zero Blunt® TOPO® PCR Cloning kit (Invitrogen) according to the manufacturer's instructions. The chemically competent cells supplied were transformed with the corresponding ligation reaction sample and spread on an agar plate in LB/amp/kan medium. The plate was incubated for 16 hrs. at 37° C., and the colonies grown were analysed for the desired ligation product. For this purpose, plasmid DNA was prepared on a mini scale using the plasmid isolation kit of Quiagen company according to the manufacturer's instructions, and was subjected to a restriction digest with the NdeI and XhoI DNA endonucleases (New England Biolabs) for which the recognition sequences had been introduced into the PCR product by means of the flanking primers. With plasmids showing the expected cleavage pattern a DNA sequence analysis was performed in the region of the gene cassette inserted using Taq DNA polymerase. For this purpose, the CycleReader™ AutoDNA Sequencing kit (Fermentas) was used according to the manufacturer's instructions as well as 0.5 µg of plasmid DNA and 1.0 pmoles of the respective fluorescence-labeled primer. The newly synthesized DNA strand was labeled during the polymerase reaction and terminated statistically, but in a base-specific manner by the incorporation of dideoxynucleotides. The resulting fluorescent DNA fragments were then separated in a liquor sequencing apparatus by polyacrylamide-urea gel electrophoresis and visualized as a band pattern for A, C, G, T in adjacent lanes.

Gene cassettes having the correct DNA sequence were cut out of the cloning vector pCR®4Blunt-TOPO® by preparative NdeI/XhoI restriction digest and isolated by preparative agarose gel electrophoresis. The insertion of the gene for the modified ubiquitin protein scaffold is carried out into the expression vector pET20B(-) (Novagen) to produce the corresponding protein or into the phasmid vector pMUBI-1, respectively, for the construction of a library of ubiquitin variations.

Preparation of a Library of Ubiquitin Variations

For random site-specific mutagenesis of 8 codons at the amino and carboxy terminus, respectively, of the synthetic ubiquitin gene two successive PCR reactions were performed. The first amplification step was performed using Pfu polymerase (Promega) in a volume of 10×50 µl. For this purpose, 5 µl of the 10×Pfu buffer supplied as well as 4 µl dNTP mix were used per each sample and filled up with H$_2$O. Furthermore, each sample contained 2.5 µl of flanking primers (Seq ID No. 34, Seq ID No. 35; 10 NM) for the introduction of the desired base pair substitutions. As a template, 1.0 ng of pMUBI-1 were used which carries the non-mutated synthetic ubiquitin gene. Following the addition of 2.5 U of Pfu polymerase (see above) an incubation was performed for 25 cycles each for 1 min at 94° C., 1 min at 60° C. and for 1.5 min at 72° C. A final incubation was carried out for 5 min at 72° C. For the selective degradation of the template DNA employed 10 U of DpnI were added per reaction sample and incubated for 1 hour at 37° C. The PCR product desired was isolated by means of preparative agarose gel electrophoresis and the QIAquick gel extraction kit (Qiagen).

The second amplification step was performed in a sample volume of 1,000 µl wherein approx. 1.0 ng of the product obtained in the first PCR reaction were used and Taq polymerase was employed. The reaction sample was pipetted—adjusted to 20 times the volume—as detailed above consisting of 10×Taq buffer, 25 mM MgCl$_2$, dNTP mix as well as the flanking primers (Seq ID No. 36, Seq ID No. 37; 10 µM) which were biotinylated at their 5' ends and each carrying recognition sequences for the SfiI endonuclease which were not compatible with each other. After filling up with H$_2$O, 2.5 U of Taq polymerase were added in the heat (see above) and the PCR program was started. An incubation was performed for 25 cycles each for 1 min at 94° C., 1 min at 60° C. and for 1.5 min at 72° C. A final incubation was carried out for 5 min at 72° C.

The subsequent cleavage of the resulting amplification product is carried out directly in the PCR reaction sample. For this purpose, in total volume of 4,000 µl the complete PCR reaction solution was mixed with the corresponding volume of 10× buffer II supplied (100 mM Tris/HCl, pH 7.9, 100 MgCl$_2$, 500 mM NaCl, 10 mM dithiothreitol), 10×BSA solution and H$_2$O. Furthermore, 4,000 U of the restriction enzyme SfiI (New England Biolabs) is were added and incubated for 16 hrs. at 50° C. The DNA was isolated from the sample using the MinElute Reaction Cleanup kit (Qiagen) and resuspended in 400 µl of sterile H$_2$O. For the separation of the PCR product which was not cleaved by SfiI the isolated DNA was mixed with the same volume of "Binding Solution" (Dynal) containing 1.0 mg/ml magnetic beads having streptavidine coupled to their surface ("Dynabeads Kilobase Binder") and incubated for 4.5 hrs. on a roller mixer at room temperature (RT). The beads bound to the optionally still present biotinylated DNA were precipitated whereas DNA which was completely cleaved by SfiI should no longer have biotinylated ends and remained in the supernatant and was precipitated over night. The resulting ubiquitin gene cleaved by SfiI and mutagenized at the desired positions was dissolved in sterile H$_2$O, desalted again using the QIAquick PCR Purification Kit (Qiagen) and finally had a concentration of 200 fmoles/µl in H$_2$O.

For the preparation of the recipient vector the phasmid pMUBI-1 was cut with SfiI according to the manufacturer's instructions and the larger (vector-) fragment was isolated by means of preparative agarose gel electrophoresis and the QIAquick Gel Extraction Kit (Qiagen). To avoid intramolecular ligation the 5' ends thereof were dephosphorylated. For this purpose, 0.5 U of alkaline phosphatase from shrimp (Pandalus borealis) as well as the buffer supplied were used in a total volume of 200 µl. The mixture was incubated for 90 min at 37° C., the DNA was isolated from the sample using the QIAquick PCR Purification Kit (Qiagen) and desalted again (QIAquick PCR Purification Kit). Finally, the DNA of the vector fragment had a concentration of 50 fmoles/µl in H$_2$O.

For the ligation, 1.6 µmol of the PCR fragment and 8.0 µmol of the vector fragment of pMUBI-1 were incubated in the presence of 2 U of T4 DNA ligase (GibcoBRL) in a total volume of 1,600 µl (50 mM Tris/HCl, pH 7.6, 10 mM MgCl$_2$, 1 mM ATP, 1 mM DTT, 5% (w/v) PEG-8,000) for three days at 16° C. After heating the sample to 65° C. for 15 min the DNA was precipitated. For this purpose, 100 µl each of the reaction solutions were mixed with 100 µl ethanol as well as 10 µl of 5 M NaAc, pH 3.0 and kept for 16 hrs. at −20° C. Subsequently, a centrifugation was carried out (60 min, 12,500 g), the sample was washed with ethanol (70% v/v, −20° C.), re-centrifugated, and finally the precipitated DNA was dissolved in 60 µl of sterile H$_2$O.

For electroporation the Gene Pulser® II system (Biorad) as well as cuvettes having an electrode spacing of 1.0 mm (Biozym) were used at 4° C. in the cold room. Using 3.5 µl each of the solutions obtained above electrocompetent *E. coli* XL1 Blue (Stratagene) were transformed according to the manufacturer's instructions. The cell suspension obtained was plated onto five agar plates (20×20 cm) containing LB/chloramphenicol medium. The plates were incubated for 16 hrs. at 37° C. and the colonies grown were counted. Accordingly, the library constructed included $2.8 \times 10^7$ independent clones each of which should be present 10,000 times in the library. Then, the colonies were floated off in a total of 100 ml of SOC medium containing 10% (v/v) glycerol and was stored in 1.0 ml aliquots at −80° C. From the resulting clones the phasmid vector was isolated from 12 randomly selected clones using the DNA Miniprep Kit sold by Qiagen company and the DNA sequence was analyzed in the region of the mutagenized ubiquitin gene. All of these clones showed functional sequences—i.e. no reading frame shifts by insertions or deletions—as well as qualitatively completely different substitutions at the mutagenized positions. No random substitutions outside of the mutagenized regions were present.

On the basis of this library based on the human ubiquitin a selection was carried out in a manner analogous to example 1 by means of the method of the phage display system known to those skilled in the art. Small modifications were introduced merely with respect to the selection of the antibiotic used (chloramphenicol instead of ampicillin).

A growth factor from the family of cysteine knot proteins served as the target. The ubiquitin Affilin™ SPU11-3-A1 had a dissociation constant in the nM range as determined by ELISA and was used for coupling studies in the BIACORE system.

One of the variations selected therefrom, SPU11-3-A1, was cloned into the pET20b expression vector using the restriction sites NdeI and XhoI. The culture conditions and purification procedure were identical to that used for SPC Affilin™ (IMAC, gel filtration) as described in example 1. For detection of the binding properties a concentration-dependent ELISA was carried out. For this purpose, different concentrations (10 nM-1 µM) of the Affilin™ variations were applied to the microtiter plate (MTP) coated with the target molecule and a polyclonal anti-ubiquitin antiserum (Sigma) was employed as primary detection reagent. After incubation (1 h) at RT the wells of the MTP were washed 3× with PBS and in a second step a monoclonal antibody conjugate (anti-IgG, Sigma) with POD was employed as detection antibody. It was found that the Affilin™ variation tested shows specific binding to human NGF and that unspecific binding to BSA or to the microtiter plate were not detectable. The humane wild-type ubiquitin serving as a control showed no binding to NGF, BSA, or to the microtiter plate.

Example 3

C-Terminal Fusion of Affilin™ with a Cysteine-Containing Peptide Linker for Selective Coupling to Different Molecules The following example demonstrates that the Affilin™ variation SPC1-A7 binding to IgG Fc could be selectively coupled to different molecules via a C-terminal cysteine.

Besides the 7 cysteines localized in the interior of the protein, the Affilin™ variation SPC1-A7 employed already bears a solution-accessible and thus free cysteine in the variable position 4. This was first substituted by a serine using QuickChange® PCR. Starting with this modified Affilin™ (SPC1-A7BB) two glycine and a cysteine as well as four other histidines in addition to the six histidines already present were inserted C-terminally by means of Quick-Change® PCR. The purpose of the affinity tag extended to 10 histidines was to enable an improved purification. Titration experiments with Ellmann's reagent have shown that the cysteine introduced is unsuitable for coupling experiments due to cysteine shuffling events with other cysteines present in the Affilin™ variation. For this reason the cysteine was substituted on the DNA level by a serine (TCT), and starting from this construct a new cysteine was introduced after a $Gly_4Ser$ linker. This served to enlarge the distance of the inserted cysteine from the cysteines in the protein and to suppress cysteine shuffling. Eventually, the resulting construct was sequenced, and titration experiments with Ellmann's reagent showed that it was suitable for coupling experiments.

For the substitution of the cysteine in position 4 by a serine in the Affilin™ variation SPC1-A7 the QuickChange® PCR method (Stratagen, La Jolla, USA) was used with the primers A7Cys4Ser_for and A7Cys4Ser_rev. For the PCR reaction 5 µl of 10× reaction buffer (100 mM KCl, 100 mM $(NH_4)_2SO_4$, 200 mM Tris-HCl, pH 8.8, 20 mM $MgSO_4$, 1% Triton® X-100, 1 mg/ml BSA), 125 ng each of the two primers, 1 µl Pfu Turbo DNA polymerase, 1µl dNTP mix and $H_2O$ up to a total volume of 50 µl were employed. As the template DNA served the gene of the Affilin™ variation SPC1-A7 in the pET20b vector. The reaction was started with a first denaturation step of 3 min at 95° C. followed by 18 repeated cycles of denaturation, primer annealing and synthesis. The denaturation at 95° C. was carried out for a period of 30 sec, the primer annealing was carried out for 1 min at 60° C. The duration of the synthesis steps was 5 min at 68° C. At the end of the PCR a final synthesis for 5 min at 68° C. was carried out. The amplification was monitored by agarose gel electrophoresis. After successful amplification a restriction digest of the template DNA employed by means of the restriction enzyme DpnI was performed. 1 µl of the enzyme (10 U/µl) was pipetted into the PCR sample, mixed and incubated for 1 h at 37° C. The vector was then introduced into a competent strain (XI-1 blue, Stratagene) by means of electroporation. For this purpose, 1 µl of the DpnI-treated restriction sample on ice was pipetted to 50 µl of electrocompetent XL-1 blue cells, mixed and pulsed in an ice-cooled electroporation cuvette (0.1 mm) at 2.5 kV, 25 µF and 200Ω. The cells were resuspended in 1 ml SOC medium and incubated for 60 min at 37° C. under agitation at 500 rpm. Afterwards, the cells were plated on selection medium (2×YT, 100 µg/ml ampicillin) and incubated at 37° C. for 16 h. 12 of the resulting clones were separately sequenced with pETTerm primer to check for correct insertion. The vector of a correct clone served as the template DNA for the next QuickChange® PCR in which two glycines, a cysteine and four additional histidines were introduced at the C-terminus. As described above, a Quick-Change® PCR with the two primers A7Gly2Cys_for and A7Gly2Cys_rev, the subsequent DpnI digest and the transformation of the XL1-Blue strain by means of electroporation were carried out. To control for correct introduction, again the plasmids of 12 clones were sequenced. The plasmid of a correct clone (SPC-1-A7JJ) was introduced into the BL21 expression strain carrying plasmid pUBS520 to subsequently express and purify the Affilin™ variation SPC1-A7BB in two chromatographic steps (affinity chromatography on Ni-NTA and gel filtration on Sephadex 75) as described above (example 1).

To examine the accessibility (Haber, 1972) of the cysteine residues introduced all free SH groups should be titrated by means of Ellmann's reagent (DTNB solution). For this purpose, to 1 ml of protein solution of the Affilin™ variation SPC1-A7JJ (50-350 µg protein in 100 mM Tris/HCl; pH 8.0) 30 µl of DTNB solution (4 mg/ml DTNB in 100 mM Tris/HCl; pH 8.0) were added. As the blank value 1 served 1 ml protein solution with 30 µl buffer (100 mM Tris/HCl; pH 8.0). As the blank value 2 served 1 ml buffer (100 mM Tris/HCl; pH 8.0) with 30 µl DTNB solution. The samples were incubated for 15 min at room temperature and the absorption at 410 nm was is measured. The absorptions of the blank values 1 and 2 were subtracted from the absorption of the test sample. From the resulting absorption value the molar concentration of free SH groups was calculated using the extinction coefficients of DTNB-SH ($\epsilon_{410\ [DTNB-SH]}$=13,600 M$^{-1}$ cm$^{-1}$) and divided by the protein concentration employed. The number of free thiol groups per protein molecule was obtained as a result. Free cysteine residues could be titrated in the Affilin™ variation SPC1-A7JJ 3-4 constructed. One free cysteine residue was expected since the cysteines present in the protein are not accessible as evidenced by the control of the titration with the Affilin™ variation SPC-1-A7Cys4Ser. This indicates cysteine shuffling of the C-terminal cysteine introduced with cysteines buried in the protein and thus suggests that the distance of the cysteine introduced to the protein is too short. For this reason the C-terminal cysteine of the Affilin™ variation SPC-1-A7JJ was substituted by a serine in a QuickChange® PCR as described above using the primers A7Gly2Ser_for and A7Gly2Ser rev. After verification of correct introduction, this construct served as a template for a PCR to introduce a Gly$_4$Ser-linker followed by a cysteine. A PCR was carried out using the primers Gly4SerCys_HindIII and A7Cys4Ser_Nde. For the PCR reaction, 5 µl 10× reaction buffer (100 mM KCl, 100 mM (NH$_4$)$_2$SO$_4$, 200 mM Tris-HCl, pH 8.8, 20 mM MgSO$_4$, 1% Triton® X-100, 1 mg/ml BSA), 125 ng each of the two primers, 1 µl Pfu Turbo DNA polymerase, 1 µl dNTP mix and H$_2$O up to a total volume of 50 µl were employed. Furthermore, 2 µl DMSO were added to the reaction mixture to resolve secondary structures of the primers. In contrast to the procedure described above 25 repeated steps of denaturation, primer annealing and synthesis were carried out at a different primer annealing temperature of 58° C. The amplification of the PCR product of this Affilin™ variation (SPC1-A7_Cys) was checked by means of agarose gel electrophoresis. Table 2 gives an overview of the constructs described herein (Tab. 2). Primer A7Cys4Ser_Nde contains an integrated restriction site for the enzyme NdeI and primer Gly4SerCys_HindIII one for the enzyme HindIII whereby it is possible to ligate the PCR product after its purification and restriction by the two enzymes into vector pET20b which is also treated with NdeI and HindIII. The restriction by the two enzymes was carried out simultaneously in a double digest. For this purpose, approx. 1 µg of the PCR product of the Afffilin™ variation SPC1-A7_Cys or 1 µg of vector pET20b, respectively, were incubated with 1 µl of the restriction enzyme NdeI (New England Biolabs, Frankfurt am Main, Germany, 20 U/µl) and 1 µl of the restriction enzyme HindIII (New England Biolabs, Frankfurt am Main, Germany, 20 U/µl) as well as 10 µl of 10× reaction buffer NEB buffer 2 (50 mM NaCl, 10 mM Tris-HCl, pH 7.9, 10 mM MgCl$_2$, 1 mM DTT) in a total volume of 100 µl for 4 h at 37° C. The resulting fragments were purified separately via a preparative agarose gel electrophoresis. For the ligation, 20 ng of the purified and NdeI/HindIII treated fragments of the vector pET20 and 120 ng of the similarly treated fragment of the Affilin™ variation SPC1-A7Cys as well as 2 µl of 10× reaction buffer (300 mM Tris-HCl, pH 7.8, 100 mM MgCl$_2$, 100 mM DTT, 10 mM ATP) and 0.5 µl of T4 DNA ligase (Promega, Mannheim, Germany, 1-3 U/µl) were employed in a total volume of 20 µl. The reaction sample was incubated for 16 h at 16° C. and the resulting vector was introduced in XL-1 blue cells by electroporation as described above. Correct introduction of the gene was verified from 12 clones obtained after transformation by sequencing with the primer pETTerm. E. coli cells (BL21(DE3), +pUBS520) were subsequently transformed with the vector of the Affilin™ variation SPC1-A7_Cys having the correct sequence. After expression and purification as described for the Affilin™ variation SPC1-A7 (example 1), the free cysteine residues were again titrated for the Affilin™ variation SPC1-A7_Cys by means of Ellmann's reagent as described above. Only one cysteine residue could be detected as expected confirming the successful introduction of a C-terminal cysteine accessible to the solvent at a sufficient distance to the protein for selective coupling to appropriate partners (Table 1). This detection of a single accessible cysteine is the basis for the selective coupling of Affilin™ to suitable coupling partners and matrices.

To provide Affilin™ SPU11-3-A1 with a C-terminal cysteine the gene for SPU11-3-A1 was cloned into pET20b modified for Affilin™ SPC1-A7 (see above) via the NcoI and XhoI restriction sites. Expression and purification of Affilin™ SPU11-3-A1_Cys was identical to the procedure for SPC1-A7_Cys.

Example 4

Analysis of the Binding Properties of the Affilin™ Variation SPC1-A7 Cys Modified with a Peptide Linker (C-Terminal Cysteine)

Figure 4:
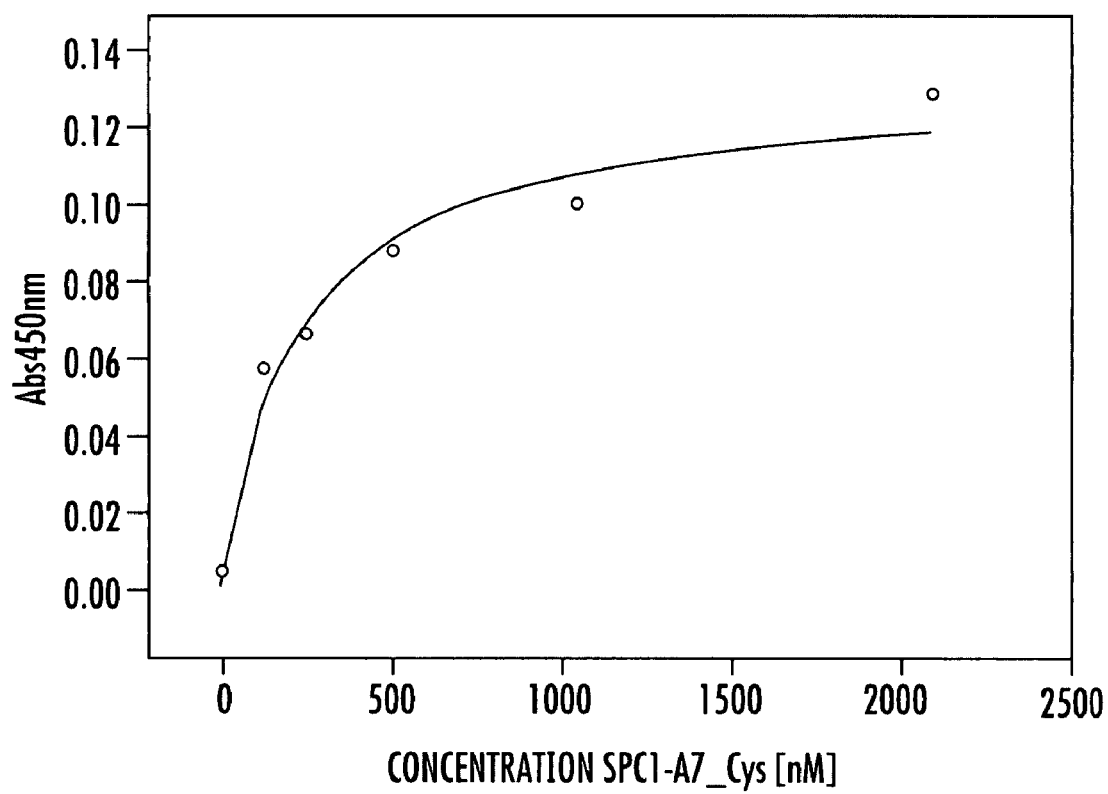
FIG. 4: Concentration-dependent ELISA for the detection of the binding of SPC1-A7_Cys to human IgG Fc. The microtiter plate was coated with 10 µg/ml IgG Fc. As the detection antibody served an anti-human gamma-II-crystallin antibody-POD conjugate in a dilution of 1:1000. The absorption values presented are mean values from two parallel measurements. An apparent $K_D$ value of 233 nM could be calculated.

The binding properties of Affilin™ SPC1-A7_Cys purified as in example 3 were tested in a concentration-dependent ELISA. For this purpose, the wells of a NUNC plate were coated with 100 µl of antigen solution (10 µg/ml of human monoclonal IgG Fc portion, Roche) over night at 4° C. On the next day, the ELISA plate was blocked with PBS (3% BSA, 0.5% Tween 20) for 2 h at room temperature. After washing of the wells with PBS (0.1% Tween 20) the modified Affilin™ was added to the wells in a concentration-dependent manner (concentration range of 10 µM-0 µM) and incubated for 1 h at RT. After another washing of the wells with PBS (0.1% Tween 20) the monoclonal anti-hGC antibody (POD-conjugated; Biogenes, Berlin) was applied in a dilution of 1:1000 (50 µl/well) and again incubated for 1 h at RT. Afterwards, the wells were washed 3× with PBS (0.1 Tween 20) and 3×PBS and the color reaction with TMB Plus (Kementec, DK) was initiated (50 µl/well). After incubation for 20 minutes at room temperature the color reaction was stopped by addition of 0.2 M H$_2$SO$_4$ (50 µl/well). The yellow color obtained was read at 450 nm (reference wavelength: 620 nm) and recorded. (FIG. 4) The evaluation of the measured values revealed an apparent KD value of 233 nM what is about equal to the unmodified Affilin™ SPC1-A7 and SPC1-A7BB (280 nM). Thus, the C-terminal modification of Affilin™ SPC1-A7 with a peptide linker including cysteine has no effect on the binding capability of the variation.

Example 5

Selective Coupling of the IgG-Binding Affilin™ SPC1-A7 Cys to Phycoerythrin (PE)

Figure 5:
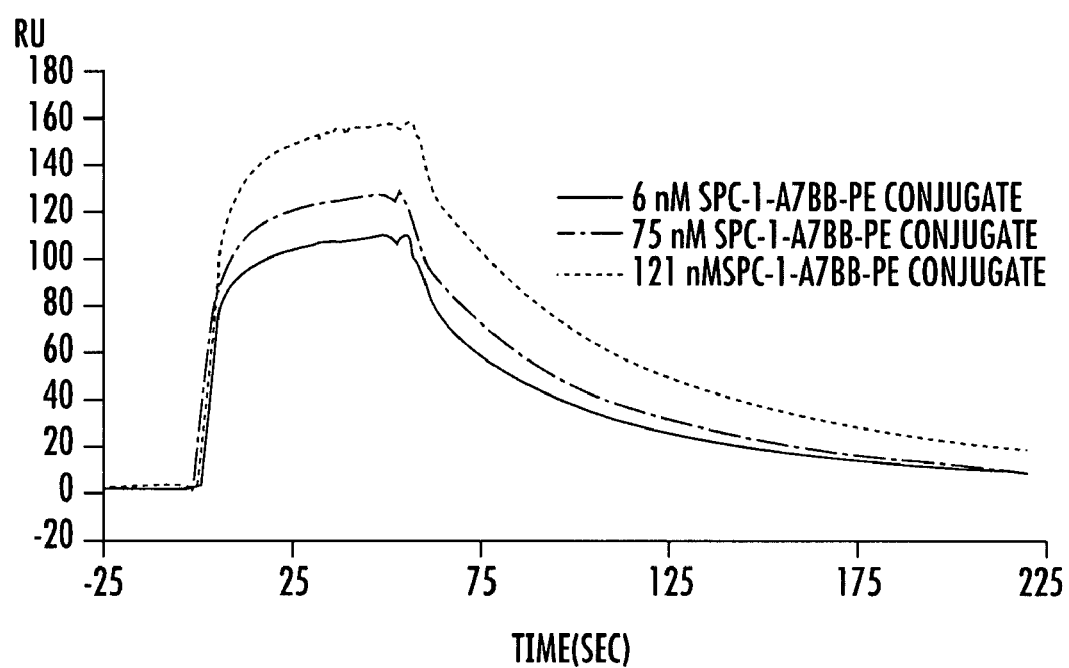
FIG. 5: Sensorgrams of the Biacore experiments for binding of the SPC1-A7BB-PE conjugate to a CM5 chip with immobilized IgG Fc. 3000 RU of IgG Fc were immobilized and the concentrations of 121 nM (dotted line), 75 nM (dashed/dotted line) and 6 nM (solid line) of SPC1-A7BB-PE conjugate were passed over the chip. The association phase was 1 min, followed by a 3 min dissociation phase. As the running buffer served HBS-EP with a flow rate of 30 µl/min. A macroscopic $K_D$ value of 15 nM could be calculated from the curves.

The coupling of Affilin™ SPC1-A7_Cys which binds to IgG to activated PE was carried out as follows:

1 mg/ml of SPC1-A7_Cys (in PBS) were reduced with 10 mM DTT for 30 min at room temperature. During the reduction phase a PD-10 column (Amersham Biosciences) was rinsed with 5 column volumes of PBS. After the reduction was carried out the reaction mixture was applied to the equilibrated PD-10 column to separate the excess DTT. The SPC1-A7_Cys reduced in this way was added with maleimid-activated phycoerythrin (Prozyme) in a molar ratio of 5:1 and incubated for 1 h at room temperature under slight agitation. Afterwards, free sulfhydryl groups of the Affilin™ which had not reacted were blocked by the addition of NEM (N-ethyl-maleimid) for 20 min at RT. The reaction mixture was subsequently purified by means of gel filtration (Sephadex S-200 HR) and the corresponding fractions were combined and stored at 4° C. The analysis of the conjugate was carried out spectroscopically. For this purpose, absorption spectra in the range of 250-750 nm were measured and the concentrations of PE and Affilin™ were determined by means of the extinction coefficients determined or supplied, respectively. The resulting conjugate of Affilin™ SPC1-A_Cys and PE (SPC1-A_Cys_PE) was tested in the BIACORE for its binding properties to IgG Fc. For this purpose, a CM5 chip coupled to IgG Fc was used at a continuous flow of 30 µl/min and with HBS-EP as running buffer. Different concentrations of SPC1-A_Cys_PE were passed one after the other over the chip and the sensorgrams obtained were analyzed with the BIACORE Evaluation Software. It was found that an avidity effect was obtained by the coupling which resulted in a decrease in the macroscopic dissociation constant from $K_D=10^{-7}$ M to $K_D=10^{-8}$ M (FIG. 5).

Example 6

Unspecific Coupling of the Fluorescent Dye Oyster® 556 to the IgG-Binding Affilin™ SPC1-A7BB The fluorescent dye Oyster® 556 (Molecular Probes) was coupled to the IgG-binding Affilin™ SPC1-A7BB (without free cysteine!) and examinations regarding binding were carried out.

Figure 6:
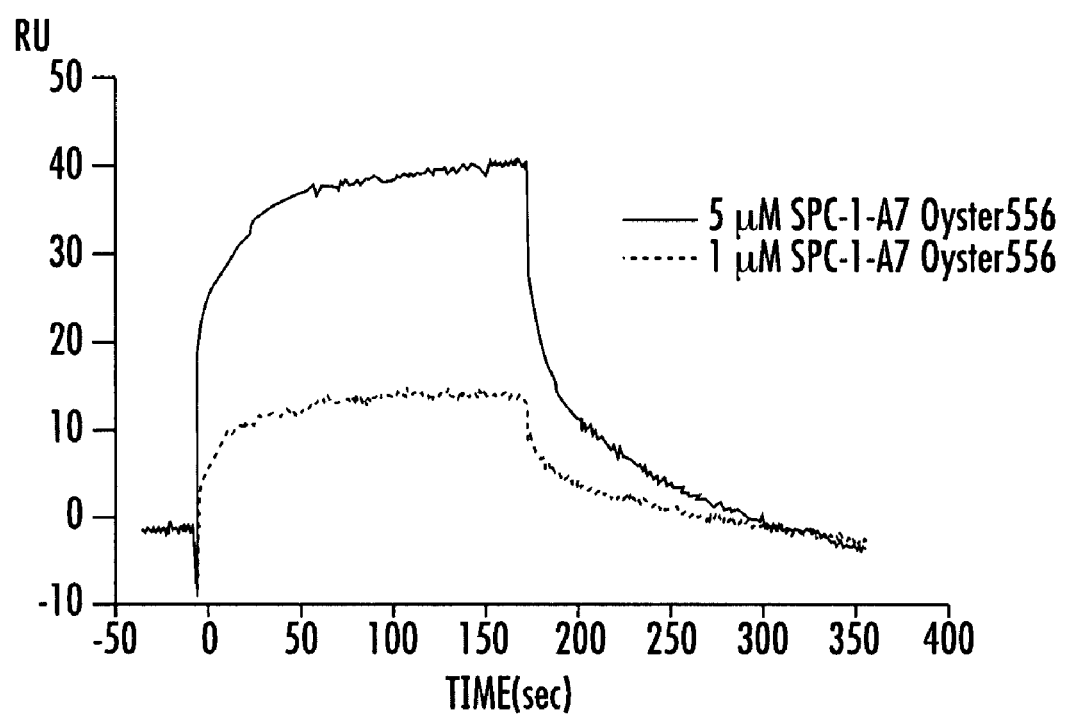
FIG. 6: Sensorgrams of the Biacore experiments for examining the binding of SPC1-A7 Oyster556 to a CM5 chip with immobilized IgG Fc. 1000 RU IgG Fc were immobilized on the chip and SPC1-A7Oyster556 in concentrations of 1 µM (dotted line) and 5 µM (solid line) was passed over the chip. The association and dissociation phase in each case was 3 min. As the running buffer served HBS-EP with a flow rate of 30 µl/min.

The coupling procedure was carried out as follows: 1 mg/ml of SPC1-A7BB in 10 mM phosphate buffer (pH 8.5) were added with the fluorescent dye Oyster® 556 (dissolved in 20 µl of dry DMF) in a molar ratio of 1:2 and incubated for 30 min at RT. The coupling reaction was stopped by the addition of 1 volume of 10% glycine solution and the sample was purified over a PD-10 column. Afterwards, the degree of coupling was quantified spectroscopically. For this purpose, the concentration of the conjugate was determined by means of the absorption at 280 nm and corrected with a correction factor supplied (Molecular Probes). The degree of coupling was then obtained from the quotient of the concentrations of Oyster®556 and the conjugate and could be determined to be 1 molecule Affilin™/0.8 molecule Oyster®556. The analysis of the binding capability of the resulting conjugate was carried out by a concentration-dependent ELISA (performed as in example 1) as well as by Biacore measurements (FIG. 6). It was found that the binding capability of Affilin™ SPC1-A7BB is unaffected after coupling to the fluorescent dye Oyster®.

Example 7

Unspecific Coupling of the Horseradish Peroxidase Enzyme (POD) to the IgG-Binding Affilin™ SPC1-A7BB The Affilin™ variation SPC1-A7BB could be unspecifically coupled to the POD enzyme, and binding studies showed that the binding activity of the Affilin™ as well as the enzymatic activity of POD is retained. The conjugate was prepared according to the following protocol:

5 mg of lyophilized horseradish peroxidase (POD, Sigma) were dissolved in 250 µl of pure water, added with 37.5 µl 0.1 M of sodium periodate solution and incubated for 10 min at 20° C. Afterwards, 25 µl ethylene glycol were added and incubated for further 5 min at 20° C. The peroxidase was dialyzed by gel filtration (G25, NAP-5 column) against pure water.

Figure 7:
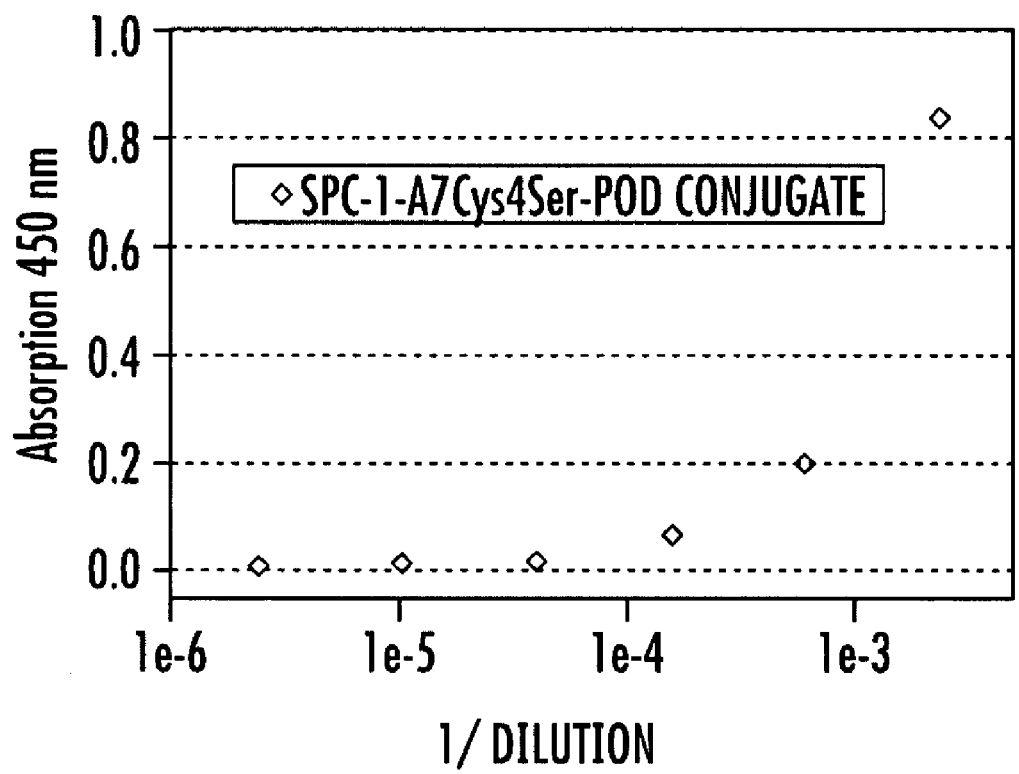
FIG. 7: Detection of the binding of an Affilin™-POD conjugate to IgG by ELISA. 10 µg/ml of human IgG were immobilized on a microtiter plate. Different dilutions of the Affilin™-POD conjugate in PBS were incubated on the microtiter plate for 1 h. After a washing step the activity of the bound POD was detected by a TMB substrate solution.

250 µl of purified Affilin™ SPC1-A7BB (IMAC, gel filtration, 4 mg/ml PBS) were added with 100 µl 0.1 M carbonate buffer (pH 9.6) and 1 mg of activated peroxidase (Sigma) was added (about 100 µl). The coupling mixture was incubated under agitation for 2 h at 20° C. Afterwards, 10 µl of 0.5 M sodium borohydride were added per ml of coupling mixture, mixed briefly and incubated for another 2 h at 4° C. without agitation. The reaction sample was buffered against PBS using a G25 column. Thiomersal (Roth), 0.1%, was added for conservation. The study of the binding activity of the conjugate to human IgG was carried out as follows:

The labeled Affilin™ was diluted in PBS (0.5% BSA, 0.05% Tween 20, 0.01% thiomersal) and the solutions were applied to a microtiter plate coated with human IgG (10 µg/ml, 100 µl/ml). The incubation time was 1 h at room temperature. Afterwards, the wells were washed 3 times with 250 µl PBS (0.1% Tween 20, 0.01% Thiomersal) each and again incubated with 100 µl TMB for 10-20 min at room temperature. The reaction was stopped by the addition of 100 µl 0.5 M sulfuric acid. The absorption (450 nm against 620 nm as reference) was measured in a microtiter plate photometer (FIG. 7). POD activity could be detected up to a dilution of 1:10,000 of the reaction sample which showed successful coupling of POD to SPC1-A7BB. By control measurements was excluded that uncoupled POD disturbs the signals.

Example 8

Specific and Unspecific Coupling of Gamma-II-Crystallin- and Ubiquitin-Based Affilin™ to Matrices The coupling of Affilin™ to matrices could be obtained by the following methods:

1.) Coupling of Affilin™ SPU3-A1_Cys via a C-terminal cysteine to a dextrane matrix, 2.) coupling of Affilin™ SPC7-E9 via primary amino groups to the dextrane matrix of the BIACORE system, and 3.) unspecific coupling of Affilin™ SPC7-E9 by means of EDC/NHS to a polymethacrylate matrix.

Figure 8:
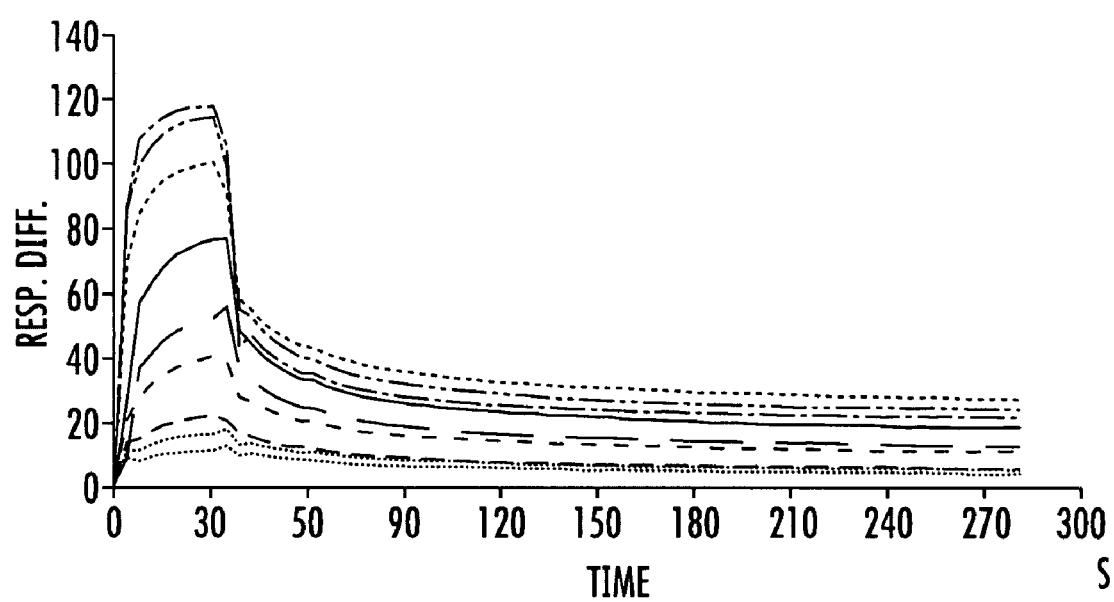
FIG. 8: Sensorgrams of the Biacore experiments for the binding of SPU11-3-A1_Cys to NGF. 200 RU of SPU11-3-A1_Cys were coupled to the CM5 chip by means of PDEA and different concentrations of NGF were passed over the chip. As the running buffer served PBS (1 mM EDTA, 0.005% Surfactant P20) with a flow rate of 30 µl/min. From the curves a $K_D$ value of 46 nM could be calculated.

1.) The coupling of SPU3-A1_Cys to the dextrane matrix of the BIACORE system was performed selectively via the C-terminal cysteine introduced. For this purpose the carboxyl groups of the dextrane matrix were activated with NHS/EDC during a contact time of 2 min and subsequently added with the thiol coupling reagent PDEA (2-(2-pyridinyldithio) ethanamine in 0.1 M borate buffer pH 8.5). After a reaction time of 4 min purified SPU3-A1_Cys (in 20 mM phosphate buffer, pH 6.0) was added to the dextrane chip modified in this manner and the reaction was continued for 7 min. The deactivation of unreacted PDEA groups was carried out with 50 mM L-cysteine (1 M NaCl) for 4 min. With this method 350 units (RU) of SPU3-A1_Cys could be immobilized on the chip and used for further kinetic analyses. After kinetic measurements the chip was regenerated with 0.1 glycin (pH 2.2), 6 M Gua/HCl, 6 M urea and 20% ethanol. In this way, the 3.0 binding activity of the Affilin™ chip was unchanged even after 20-30 regeneration cycles (FIG. 8).

Figure 9:
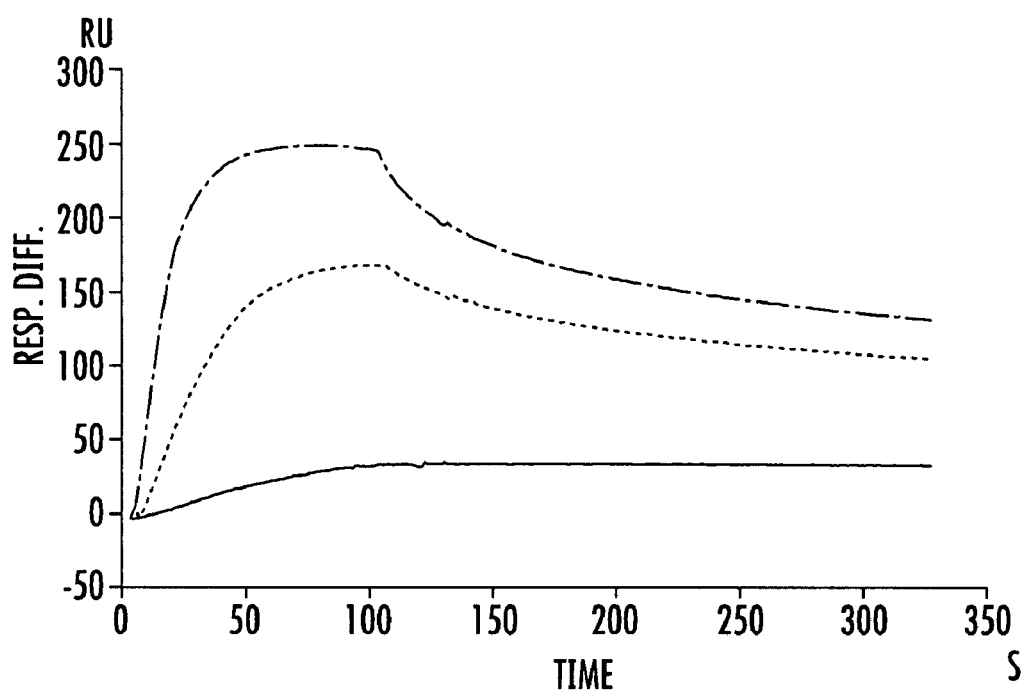
FIG. 9: Sensorgrams of the Biacore experiments for the binding of SPC7-E9 to a CM5 chip with proNGF. 280 RU of proNGF were immobilized and different concentrations of proNGF passed over the chip. As the running buffer served HBS-EP with a flow rate of 30 µl/min. From the curves a $K_D$ value of 1.4 nM could be calculated.
Figure 10:
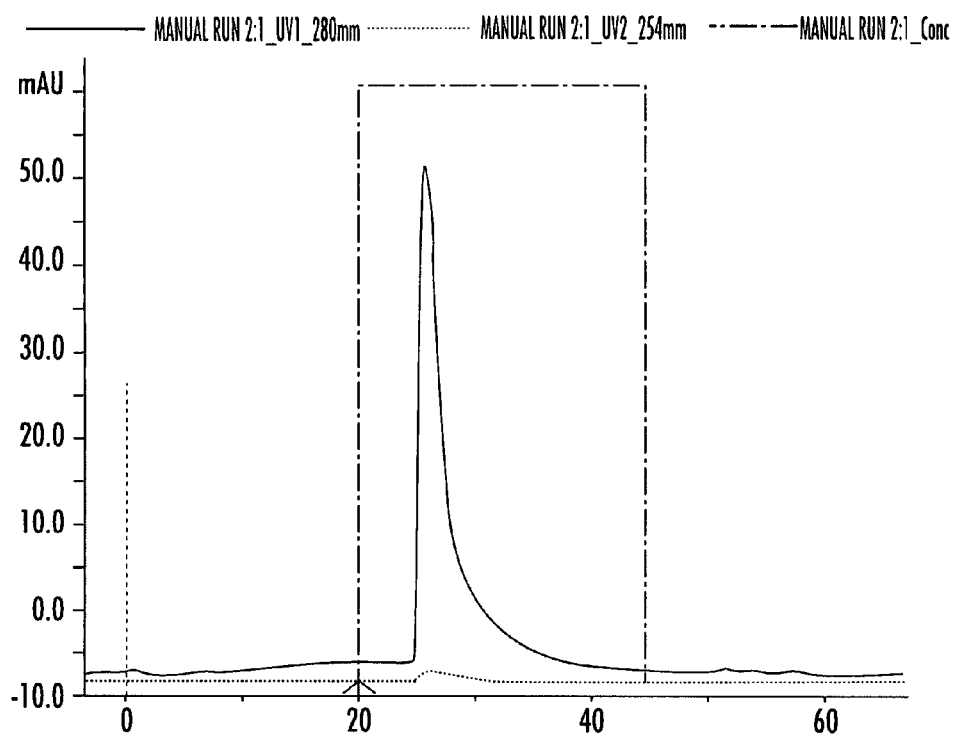
FIG. 10: Elution of proNGF from a SPC7-E9 affinity column. 400 µg of purified proNGF were applied (time 0, dotted line), and subsequently rinsing was performed with 20 column volumes of running buffer. The elution was carried out with 0.1 M glycine pH 2.2 (dashed/dotted line). The run was carried out at a flow of 1 ml/min. The detection of the proteins was carried out at 280 nm (solid line).
Figure 11:
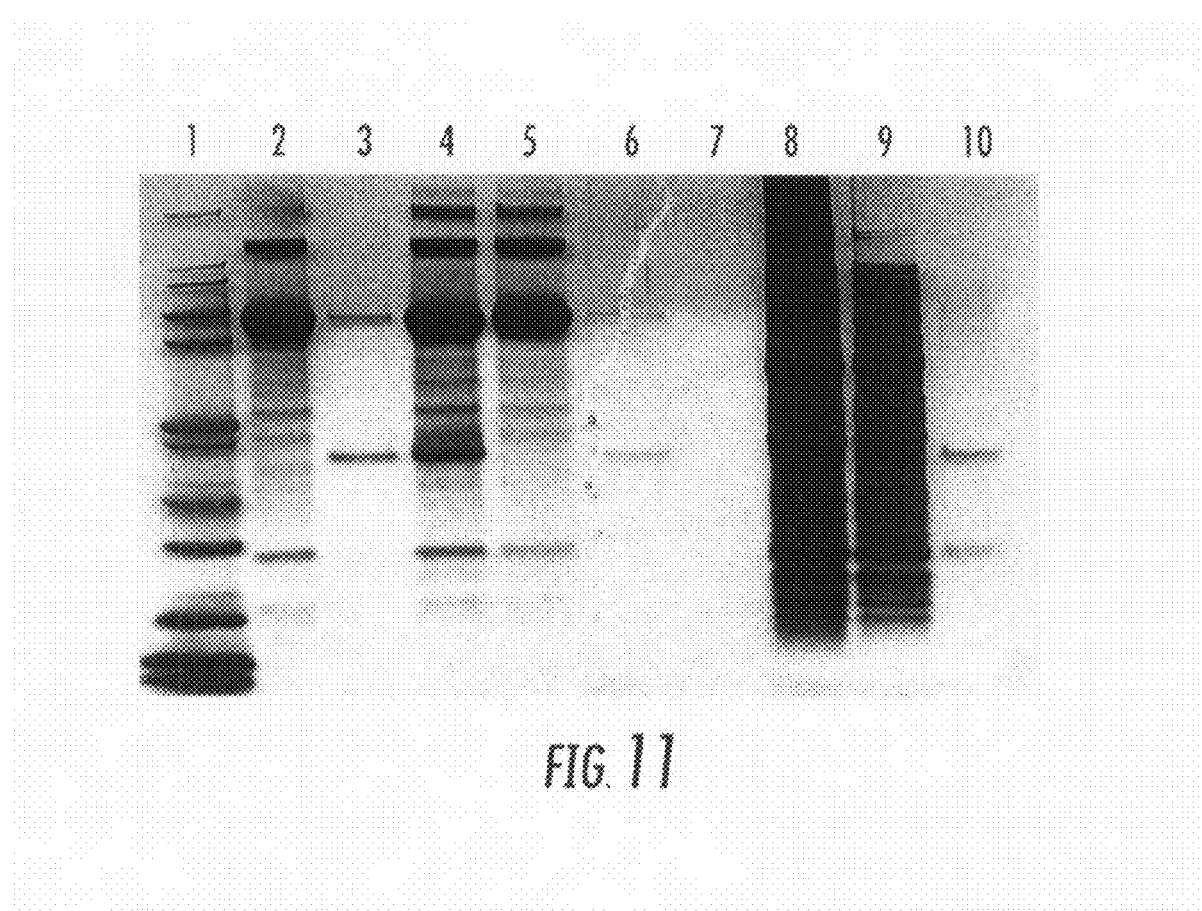
FIG. 11: SDS PAGE of the separation of proNGF from a BSA solution and from *E. coli* crude extract. (from left to right) lane 1: marker proteins, lane 2: BSA standard, lane 3: proNGF standard, lane 4: mixture of BSA and proNGF standards (start), lane 5: flowthrough, lane 6: elution with 0.2 M glycine (pH 2.2), lane 7: empty, lane 8: mixture of *E. coli* crude extract (BI 21) and proNGF standard, lane 9: flowthrough, lane 10: elution with 0.2 M glycine (pH 2.2)

2.) Furthermore, SPC7-E9 could be coupled unspecifically via surface-exposed amino groups (lysines) by means of NHS/EDC to the carboxyl is groups of the BIACORE dextrane matrix in the following manner: The CM5 chip was activated for 7 min with NHS/EDC, and afterwards purified SPC7-E9 (in 20 mM Na phosphate buffer, pH 6.0) was passed over the chip for further 7 min. After the coupling was carried out the remaining reactive groups were deactivated for 7 min with 1 M ethanolamine (pH 8.5). For the analysis of dissociation constants the target proNGF was passed over the chip in different concentrations, the binding was monitored online (FIG. 9), and the curves were subsequently evaluated with the BiaEvaluation Software. In this manner, the $K_D$ value could be determined to be 1.4 nM. After kinetic measurements the chip was regenerated with 0.1 glycin (pH 2.2), 10 mM HCl, 10 mM NaOh, 6 M Gua/HCl, 6 M urea and 20% ethanol. In this way, the binding activity of the Affilin™ chip was unchanged even after several regeneration cycles 3.) Purified SPC7-E9 protein (4 mg) was buffered in 0.1 M borate buffer (0.5 M $Na_2SO_4$, pH 9) over a PD-10 column (Amersham) and coupled to Fractogel® EMD Epoxy (M). For this purpose the gel (0.5 g) was incubated in 0.1 M borate buffer (0.5 M $Na_2SO_4$, pH 9) for 2 h at RT and afterwards washed several times with this buffer. The coupling reaction was initiated by the addition of SPC7-E9 to the epoxy matrix and continued at RT for 24 h under continuous agitation. A reference column without SPC7-E9 served as control and was treated in an identical manner. By means of 1 M ethanolamine (pH 9.5) the reaction was stopped for 48 h at RT and the gel matrix was washed with sodium acetate buffer (0.1 M, pH 4.0), 1 M NaCl and PBS (50 column volumes each). The Affilin™ SPC7-E9 affinity matrix generated in this manner was filled into a C column (Amersham Biosciences, 1×10 cm) and connected to a chromatography system (Akta Explorer, Amersham Biosciences). In all cases PBS (0.5 mM EDTA) at a flowrate of 1 ml/min was used as the running buffer. To test the binding capability of the Affilin™ column generated in this way purified proNGF was applied. After rinsing the column with 10-20 column volumes of running buffer bound proNGF was eluted with 0.1 M glycine (pH 2.2) (FIG. 10). Furthermore, it was possible to separate proNGF from substance mixtures with BSA and from *E. coli* crude extract. For this purpose 1 ml BSA solution (5 mg/ml, Sigma) was mixed with 0.5 ml proNGF (1.3 mg/ml) and applied to the Affilin™ column. After rinsing the column with 20 column volumes of running buffer bound proNGF was eluted with glycine (0.1 M, pH 2.2). After regeneration of the column with 10 column volumes of 6 M Gua/HCl furthermore a mixture of 1 ml *E. coli* crude extract (soluble supernatant after cell disruption (lysozyme/benzonase/sonication) of the bacterial pellets of 50 ml BI21 overnight culture) and 0.5 ml proNGF (1.3 mg/ml) was applied to the Affilin™ column. After rinsing the column with 20 column volumes of running buffer bound proNGF was also eluted with glycine (0.1 M, pH 2.2). The column was subsequently regenerated with 0.1 M glycine (pH 2.2), 10 mM HCl, 10 mM NaOH, 6 M Gua/HCl, 6 M urea and 20% ethanol. The eluted fractions from the separation of proNGF from BSA and *E. coli* crude extracts were analyzed by means of gel electrophoresis (FIG. 11). After 10 test runs an unaltered binding of proNGF to the SPC7-E9 column could be observed.

TABLE 1

| Variation | $A_{410}$ | Blank value 1 | Blank value 2 | Corr. $A_{410}$ | Concentration employed [µg/ml] | Number of cysteines in the protein | Theor. accessible cysteines | Number of titrated cysteines |
|---|---|---|---|---|---|---|---|---|
| SPC-1-A7BB | 0.2142 | 0.0897 | 0.1232 | 0.0013 | 50 | 7 | 0 | 0 |
|  | 0.2254 | 0.1003 | 0.1232 | 0.0019 | 100 |  |  |  |
| SPC-1-A7JJ | 0.3154 | 0.0832 | 0.1232 | 0.109 | 50 | 8 | 1 | 4 |
|  | 0.4412 | 0.0738 | 0.1232 | 0.2442 | 100 |  |  |  |
| SPC-1-A7_Cys | 0.235 | 0.0834 | 0.1232 | 0.0286 | 50 | 8 | 1 | 1 |
|  | 0.272 | 0.0966 | 0.1232 | 0.0522 | 100 |  |  |  |

TABLE 2

SPC-1-A7
5'-ATGGGTCTGATCTGT [gamma-Kristallin] CTCGAGCACCACCACCACCACCAC-3'
$NH_2$-M G L I C                          L E H H H H H H-COOH SPC-1-A7BB
5'-ATGGGTCTGATCTCT [gamma-Kristallin] CTCGAGCACCACCACCACCACCAC-3'
$NH_2$-M G L I S                          L E H H H H H H-COOH SPC-1-A7JJ
5'-ATGGGTCTGATCTCT [gamma-Kristallin] CTCGAGTGCGGCGGCCATCACCATCACCACCACCACCACCAC-3'
$NH_2$-M G L I S                          L E C G G H H H H H H H H-COOH SPC-1-A7_Cys
5'-ATGGGTCTGATCTCT [gamma-Kristallin] CTCGAGTCCGGCGGCGGGGGGGAGGATCTTGCCATCACCATCACCACCACCACCACCAC
$NH_2$-M G L I S                          L E S G G G G G G S C H H H H H H H H-COOH DNA Sequence of the Human Gamma-II-Crystallin Library CR20 (SEQ ID NO: 1)
ATGGGTNNKATCNNKTTCNNKGAAGACCGTGCTTTCCAGGGTCGTNNKTA
CNNKTGCNNKACCGACTGCCCGAACCTGCAGCCGTACTTCTCCCGTTGCA
ACTCCATCNNKGTTNNKTCCGGTTGCTGGATGATCTACGAACGTCCGAAC
TACCAGGGTCACCGTCACCAGTACTTCCTGCGGCGTGGGGAGTACCCCGA
CTACCAGCAATGGATGGGCCTCAGCGACTCCATCCGCTCCTGCTGCCTCA
TCCCCCCCCACTCTGGCGCTTACAGAATGAAGATCTACGACAGAGATGAA
TTGAGGGGACAAATGTCAGAGCTCACAGACGACTGTCTCTCTGTTCAGGA
CCGCTTCCACCTCACTGAAATT
CACTCCCTCAATGTGCTGGAGGGCAGCTGGATCCTCTATGAGATGCCCAA
CTACAGGGGAGGCAGTATCTGCTGAGGCCGGGGGAGTACAGGAGGTTTC
TTGATTGGGGGCTCCAAATGCCAAAGTTGGCTCTCTTAGACGAGTCATG
GATTTGTACGCG DNA-Sequences of Gamma-II-Crystallin-Based Affilin™

SPC1-A1 (SEQ ID NO: 2)
ATGGGTTTTATCTGGTTCATGGAAGACCGTGCTTTCCAGGGTCGTAGGTA
CGATTGCGGTACCGACTGCCCGAACCTGCAGCCGTACTTCTCCCGTTGCA
ACTCCATCAAGGTTAAGTCCGGTTGCTGGATGATCTACGAACGTCCGAAC
TACCAGGGTCACCGTCACCAGTACTTCCTGCGGCGTGGGGAGTACCCCGA
CTACCAGCAATGGATGGGCCTCAGCGACTCCATCCGCTCCTGCTGCCTCA
TCCCCCCCCACTCTGGCGCTTACAGAATGAAGATCTACGACAGAGATGAA
TTGAGGGGACAAATGTCAGAGCTCACAGACGACTGTCTCTCTGTTCAGGA
CCGCTTCCACCTCACTGAAATTCACTCCCTCAATGTGCTGGAGGGCAGCT
GGATCCTCTATGAGATGCCCAACTACAGGGGAGGCAGTATCTGCTGAGG
CCGGGGGAGTACAGGAGGTTTCTTGATTGGGGGCTCCAAATGCCAAAGT
TGGCTCTCTTAGACGAGTCATGGATTTGTACGCG

SPC1-A7 (SEQ ID NO: 3)
ATGGGTCTGATCTGTTTCTCTGAAGACCGTGCTTTCCAGGGTCGTAGGTA
CATGTGCCTGACCGACTGCCCGAACCTGCAGCCGTACTTCTCCCGTTGCA
ACTCCATCAATGTTTGGTCCGGTTGCTGGATGATCTACGAACGTCCGAAC
TACCAGGGTCACCGTCACCAGTACTTCCTGCGGCGTGGGGAGTACCCCGA
CTACCAGCAATGGATGGGCCTCAGCGACTCCATCCGCTCCTGCTGCCTCA
TCCCCCCCCACTCTGGCGCTTACAGAATGAAGATCTACGACAGAGATGAA
TTGAGGGGACAAATGTCAGAGCTCACAGACGACTGTCTCTCTGTTGAGGA
CCGCTTCCACCTCACTGAAATTCACTCCCTCAATGTGCTGGAGGGCAGCT
GGATCCTCTATGAGATGCCCAACTACAGGGGAGGCAGTATCTGCTGAGG
CCGGGGGAGTACAGGAGGTTTCTTGATTGGGGGCTCCAAATGCCAAAGT
TGGCTCTCTTAGACGAGTCATGGATTTGTACGCG

SPC1-G3 (SEQ ID NO: 4)
ATGGGTTCTATCATTTTCCTTGAAGACCGTGCTTTCCAGGGTCGTATTTA
CGGTTGCACTACCGACTGCCGGAACGTGCAGGCGTACTTCTCCCGTTGCA
ACTCGATCGTGGTTCAGTCCGGTTGCTGGATGATCTACGAAGGTCCGAAC
TACCAGGGTCACCGTCACCAGTACTTCCTGGGGCGTGGGGAGTACCCCGA
CTACCAGCAATGGATGGGCCTCAGCGACTCCATCCGCTGCTGCTGCCTCA
TCCCCCCCCACTCTGGCGCTTACAGAATGAAGATCTACGACAGAGATGAA
TTGAGGGGACAAATGTCAGAGCTCACAGACGACTGTCTCTCTGTTCAGGA
CCGCTTCCACCTGACTGAAATTCACTCCCTCAATGTGCTGGAGGGCAGCT
GGATCCTGTATGAGATGCCCAACTACAGGGGGAGGCAGTATCTGCTGAGG
CCGGGGGAGTACAGGAGGTTTCTTGATTGGGGGGTCCAAATGCCAAAGT
TGGCTCTGTTAGACGAGTCATGGATTTGTACGCG

SPC1-A7BB (SEQ ID NO: 5)
ATGGGTCTGATCTCTTTCTCTGAAGAGGGTGCTTTCCAGGGTCGTAGGTA
CATGTGCCTGACCGACTGCCCGAACCTGCAGCCGTACTTCTCCCGTTGCA
ACTCCATCAATGTTTGGTCCGGTTGCTGGATGATCTACGAACGTCCGAAC
TAGCAGGGTCACGAGTACTTCCTGCGGCGTGGGGAGTACGCCGACTACCA
GCAATGGATGGGCCTCAGCGACTCCATCCGCTCCTGCTGCCTCATCCCCC
CCCACTCTGGCGCTTACAGAATGAAGATCTACGACAGAGATGAATTGAGG
GGACAAATGTCAGAGCTGACAGACGACTGTCTCTGTGTTCAGGAGCGCTT
CCAGCTCACTGAAATTCACTCCCTCAATGTGCTGGAGGGCAGCTGGATCC
TCTATGAGATGCCCAAGTACAGGGGGAGGCAGTATCTGCTGAGGCCGGGG
GAGTACAGGAGGTTTCTTGATTGGGGGCTCCAAATGCCAAAGTTGGCTC
TCTTAGACGAGTCATGGATTTGTACCTCGAG<u>CACCACCACCACCAC</u>

SPC1-A7JJ (including His10) (SEQ ID NO: 6)
ATGGGTCTGATCTCTTTCTCTGAAGACCGTGCTTTCCAGGGTCGTAGGTA
CATGTGCCTGACCGACTGCCCGAACCTGCAGCCGTACTTCTCCCGTTGCA
ACTCCATCAATGTTTGGTCCGGTTGCTGGATGATCTACGAAGGTCCGAAC
TACCAGGGTGACCAGTACTTCCTGCGGGGTGGGGAGTACCCCGACTACCA
GCAATGGATGGGCCTCAGCGACTCCATCCGCTCCTGCTGCCTCATCCCCC
CCCACTCTGGCGCTTACAGAATGAAGATCTACGACAGAGATGAATTGAGG
GGACAAATGTCAGAGCTCACAGACGACTGTCTCTCTGTTCAGGACCGCTT
CCACCTCACTGAAATTCACTCCCTCAATGTGCTGGAGGGCAGCTGGATCC
TCTATGAGATGCCCAACTACAGGGGAGGCAGTATCTGCTGAGGCCGGGG
GAGTACAGGAGGTTTCTTGATTGGGGGCTCCAAATGCCAAAGTTGGCTC
TCTTAGACGAGTCATGGATTTGTACCTCGAGTGCGGCGGC<u>CATCACCATC
ACCACCACCACCACCAC</u>

SPC1-A7_Cys (including His10) (SEQ ID NO: 7)
ATGGGTCTGATCTCTTTCTCTGAAGACCGTGCTTTCCAGGGTCGTAGGTA
CATGTGCCTGACCGACTGCCCGAACCTGCAGCCGTACTTCTCCCGTTGGA

```
ACTCCATCAATGTTTGGTCCGGTTGCTGGATGATCTACGAACGTCGGAAC

TACCAGGGTCACCAGTACTTCCTGCGGCGTGGGGAGTACCCCGACTACCA

GCAATGGATGGGGCTCAGCGACTCGATCCGCTCCTGCTGCCTCATCCCCC

CGCACTCTGGCGCTTACAGAATGAAGATCTACGAGAGAGATGAATTGAGG

GGACAAATGTCAGAGCTCACAGAGGACTGTCTCTCTGTTCAGGACCGCTT

CCACGTCACTGAAATTCACTCCCTCAATGTGCTGGAGGGCAGCTGGATCC

TCTATGAGATGCCCAACTACAGGGGAGGGAGTATCTGCTGAGGCCGGGG

GAGTACAGGAGGTTTCTTGATTGGGGGCTCGAAATGCGAAAGTTGGCTC

TCTTAGACGAGTCATGGATTTGTACCTCGAGTCCGGCGGCGGGGGGGAG

GATCTTGCCATCACCATCACCACCACCACCACCAC

SPC7-E9 (including His6)
                                            (SEQ ID NO: 8)
ATGGGTTTTATCTGTTTCTTGGAAGACCGTGCTTTCCAGGGTCGTTCTTA

CGCTTGCGATACTGACTGCCCGAACCTGCAGCCGTACTTCTCCCGTTGCA

ACTCCATCAGTGTTCTGTCCGGTTGCTGGATGATCTACGAACGTCCGAAC

TACCAGGGTCACCAGTACTTCCTGCGCGTGGGGAGTACCCCGACTACCA

GCAATGGATGGGCCTCAGCGACTCCATCCGCTCCTGCTGCCTCATCCCCC

CCCACTCTGGCGCTTACAGAATGAAGATCTACGACAGAGATGAATTGAGG

GGACAAATGTCAGAGCTCACAGACGACTGTCTCTCTGTTCAGGACCGCTT

CCACCTCACTGAAATTCACTCCCTCAATGTGCTGGAGGGGAGCTGGATCC

TCTATGAGATGCCCAACTACAGGGGAGGCAGTATCTgCTGAGGCCGGGG

GAGTACAGGAGGTTTCTTGATTGGGGGCTCCAAATGCCAAAGTTGGCTC

TCTTAGACGAGTCATGGATTTGTACCTCGAG<u>CACCACCACCACCACCAC</u>

Ubiquitin wildtype
                                            (SEQ ID NO: 9)
ATGCAGATCTTCGTGAAGAGCCTGACGGGCAAGACCATCACTCTGGAGGT

GGAGCCCAGTGACACCATCGAAAATGTGAAGGCCAAGATCCAAGATAAAG

AAGGCATTCCGCCCGACCAGCAGAGGCTCATCTTTGCAGGCAAGCAGCTG

GAAGATGGCCGGACTCTTTCTGACTACAACATCCAGAAAGAGTGGACCCT

GCAGCTGGTCCTCCGCCTGAGGGGCGGC

Modified ubiquitin (MUBI)
                                            (SEQ ID NO: 10)
ATGCAAATCTTCGTTAAACCCTGACGGGAAAGACTATCACCCTGGAGGT

AGAACCGTCCGACACCATCGAAAATGTCAAAGCTAAAATCCAAGACAAAG

AAGGAATTGCACCTGACCAGCAACGCCTAGCTTTCGCAGGACGACAAGTA

GAGGACGGGCTCACCCTGTCTGACTACAACATCCAAAAAGAATCCACCCT

CCACGTGGCACTCCTCCTGCGGGCC

UB10 (library)
                                            (SEQ ID NO: 11)
ATGNNKATCNNKGTTNNKACCCTGACGGGAAAGACTATCACCCTGGAGGT

AGAACCGTCCGACACGATCGAAAATGTGAAAGCTAAAATCCAAGACAAAG

AAGGAATTCCACCTGACCAGCAACGCCTAGCTTTCGCAGGACGACAACTA

GAGGACGGGCTCACCCTGTCTGACTACAACATCNNKNNKNNKNNKNNKCT

CCACCTGGCACTCCTCCTGCGGGCC
```

DNA Sequences of Ubiquitin-Based Affilin™

```
SPU11-3-A1 (including His6)
                                            (SEQ ID NO: 12)
ATGCGGATCCGTGTTGCTACCCTGACGGGAAAGACTATCACCCTGGAGGT

AGAACCGTCCGACACCATCGAAAATGTCAAAGGTAAAATCCAAGACAAAG

AAGGAATTCCACCTGACCAGCAACGGGTAGCTTTCGCAGGACGACAACTA

GAGGACGGGCTCACGCTGTCTGACTACGACATCCGTCATGGTACGTCGCT

CGACCTGGCACTCCTCCTGCGGGCCCTCGAG<u>CACCACCACCACCACCAC</u>

SPU11-3-A1_Cys (inklusive His10)
                                            (SEQ ID NO: 13)
ATGCGGATCCGTGTTGCTACCCTGACGGGAAAGACTATCACCCTGGAGGT

AGAACCGTCCGACACCATCGAAAATGTCAAAGCTAAAATCCAAGACAAAG

AAGGAATTCCACCTGACCAGCAACGCCTAGCTTTCGCAGGACGACAACTA

GAGGACGGGCTCACCCTGTCTGACTACGACATCCGTCATGGTACGTCGCT

CCACCTGGCACTCCTCCTGCGGGCCCTCGAGTCCGGCGGCGGGGGGGAG

GATCTTGCCATCACCATCACCACCACCACCACCAC
```

Primers

```
pCAN700
                                            (SEQ ID NO: 14)
(5'-CCA TGA TTA CGC CAA GCT TTG GAG CC-3')

A7Cys4Ser_for
                                            (SEQ ID NO: 15)
(5'-CCA TGG GTC TGA TCT CTT TCT CTG AAG ACC G-3')

A7Cys4Ser_rev
                                            (SEQ ID NO: 16)
(5'-CGG TCT TCA GAG AAA GAG ATC AGA CCC ATG G-3')

pETTerm
                                            (SEQ ID NO:17)
(5'-GCT AGT TAT TGC TCA GCG GTG GC-3')
```

-continued

A7Gly2Cys_for
(SEQ ID NO: 18)
(5'-GGA TTT GTA CCT CGA GTG CGG CGG CCA TCA CCA TCA CCA CCA CCA CCA CCA CCA CTG AGA TCC GGC-3')

A7Gly2Cys_rev
(SEQ ID NO: 19)
(5'-GCC GGA TCT GAG TGG TGG TGG TGG TGG TGG TGA TGG TGA TGG CCG CCG CAC TCG AGG TAC AAA TCC-3')

A7Gly2Ser_for
(SEQ ID NO: 20)
(5'-GGA TTT GTA CCT CGA GTC CGG CGG CCA TCA CC-3')
and A7Gly2Ser rev
(SEQ ID NO: 21)
(5'-GGT GAT GGC CGC CGG ACT CGA GGT ACA AAT CC-3')

A7Gly2Ser_rev
(SEQ ID NO: 22)
(5'-GGT GAT GCC GGC CGC ACT CGA GGT ACA AAT CC-3')

Gly4SerCys_HindIII
(SEQ ID NO: 23)
(5'-GGG GGA AGC TTT TAT CAG TGG TGG TGG TGG TGG TGG TGA TGG TGA TGG CAA GAT-3')

A7Cys4Ser_Nde
(SEQ ID NO: 24)
(5'-GGA GAT ATA CAT ATG GGT CTG ATC TCT TTC TCT G-3')

SEQ ID NO: 25:
ATGAAATACC TATTGCCTAC GGCAGCCGCT GGATTGTTAT TACTCGCGGC CCAGCCGGCC    60

ATGGCCATGC AAATCTTCGT TAAAACCCTG ACGGGAAAGA CTATCACCCT GGAGGTAGAA   120

CCGTCCGACA CCATCGAAAA TGTCAAAGCT AAAATCCAAG ACAAAGAAGG AATTCCACCT   180

GACCAGCAAC GCCTAGCTTT CGCAGGACGA CAACTAGAGG ACGGGCTCAC CCTGTCTGAC   240

TACAACATCC AAAAGAATC CACCCTCCAC CTGGCACTCC TCCTGCGGGC C             291

SEQ ID NO: 26
ATGCAAATCT TCGTTAAAAC CCTGACGGGA AAGACTATCA CCCTGGAGGT              50

SEQ ID NO: 27
GGATTTTAGC TTTGACATTT TCGATGGTGT CGGACGGTTC TACCTCCAGG GTG          53

SEQ ID NO: 28
GTCAAAGCTA AAATCCAAGA CAAAGAAGGA ATTCCACCTG ACCAGCAACG CCT          53

SEQ ID NO: 29
GGGTGAGCCC GTCCTCTAGT TGTCGTCCTG CGAAAGCTAG GCGTTGCTGG              50

SEQ ID NO: 30
GACGGGCTCA CCCTGTCTGA CTACAACATC AAAAAGAAT CCACCCTCCA               50

SEQ ID NO: 31
GAGTGCTCGC AGCAGGAGTG CCAGGTGGAG GGTGGATTC                          39

SEQ ID NO: 32
GATATACATA TGCAAATCTT CG                                            22

SEQ ID NO: 33
GTGGTGCTCG AGTGCTCG                                                 18

SEQ ID NO: 34
CCAGCCGGCC ATGGCCATGN NKATCNNKGT TNNKACCCTG ACGGGAAAGA CTATC         55

SEQ ID NO: 35
CAGGAGGAGT GCCAGGTGGA GMNNMNNMNN MNNMNNGATG TTGTAGTCAG ACAGG         55

SEQ ID NO: 36
GTTATTACTC GCGGCCCAGC CGGGCATGGC CATG                               34

SEQ ID NO: 37
GAGTTTTTGT TCGGCCTCGA GGGCGCGCAG GAGGAGTGCC AGGTGGAG                48

REFERENCES

Ausuebel, F. M., Brent, R., Kinston, R. E., Moore, D. D., Seidmann, J. G., Smith, J. A. and Struhl, K. (1994): Current protocols in molecular biology. John Wiley & Sons, Inc.

Berman, H. M., Westbrook, J., Feng, Z., Gilliland, G., Bhat, T. N., Weissig, H., Shindyalov, I. N. and Bourne, P. E. (2000) The Protein Data Bank. *Nucleic Acid Res.*, 28, 235-242.

Blundell, T., Lindley, P., Miller, L., Moss, D., Slingsby, C., Tickle, I., Turnell, B., and Wistow, G. (1981). The molecular structure and stability of the eye lens: x-ray analysis of gamma-crystallin II. Nature 289, 771-777.

Buchberger A, Howard M J, Proctor M, Bycroft M, National Library of Medicine, J Mol. Bil. 2001 Mr 16; 307(1); 17-24.

Butt, T. R., Jonnalagadda, S., Monia, B. P., Sternberg, E. J., Marsh, J. A., is Stadel, J. M., Ecker, D. J. and Crooke, S. T. (1989) Ubiquitin fusion augments the yield of cloned gene products in *Escherichia coli*. PNAS 86, 2540-2544.

Finucane, M. D., Tuna, M., Lees, J. H., and Woolfson, D. N. (1999). Core-directed protein design. I. An experimental method for selecting stable proteins from combinatorial libraries. Biochemistry 38, 11604-11612.

Finucane, M. D., and Woolfson, D. N. (1999). Core-directed protein design. II. Rescue of a multiply mutated and destabilized variant of ubiquitin. Biochemistry 38, 11613-11623.

Haber, A. F. S. A. (1972). Reaction of protein sulfhydryl groups with Ellman's reagent. In Methods Enzymology, C. H. Hirs, and S, N. Timasheff, eds., pp. 457-464.

Hanes, J. et al. (1997): In vitro selection and evolution of functional proteins by using ribosome display. Proc. Natl. Acad. Sci. USA. 94, 4937-42.

Hazes, B. and Hol, W. G. J. (1992): Comparison of the hemocyanin β-barrel with other greek key β-barrels: possible importance of the "β-zipper" in protein structure and folding. Proteins: Struct., Funct. Gen. 12, 278-298.

Hemmingsen, J. M., Gernert, K. M., Richardson, J, S, and Richardson, D. C. (1994): The tyrosine corner: a feature of most greek key β-barrel proteins. Prot. Science 3, 1927-1937.

Herrmann, J. E., and Morse, S. A. (1973) Coupling of peroxidase to poliovirus antibody: Characteristics of the conjugates and their use in virus detection. Infection and Immunity, 645-649.

Jaenicke, R. (1994). Eye-lens proteins: structure, superstructure, stability, genetics. Naturwissenschaften 81, 423-429.

Jaenicke, R. (1996). Stability and folding of ultrastable proteins: eye lens crystallins and enzymes from thermophiles. Faseb J 10, 84-92.

Jaenicke, R., and Slingsby, C. (2001). Lens crystallins and their microbial homologs: structure, stability, and function. Crit. Rev Biochem Mol Biol 36, 435-499.

Kumaraswamy, V. S., Lindley, P. F., Slingsby, C., and Glover, I. D. (1996). An eye lens protein-water structure: 1.2 angstrom resolution structure of gamma B-crystallin at 150K. Acta Crystallogr D Biol Crystallogr 52, 611.

Larsen C N, Wang H., National Library of Medicine; J Proteome Res. 2002 September-October; 1(5):411-9.

Lazar, G. A., Desjarlais, J. R., and Handel, T. M. (1997). De novo design of the hydrophobic core of ubiquitin. Protein Sci 6, 1167-1178.

Ling, M. M. (2003). Large antibody display libraries for isolation of high-affinity antibodies. Comb Chem High Throughput Screen 6, 421-432.

Lottspeich, F., and Zorbas, H. (1998). Bioanalytik (Heidelberg, Spektrum Akademischer Verlag).

Mandal, K., Chakrabart, B., Thomson, J. and Siezen, R. J. (1987): Structure and stability of β-crystallins. Denaturation and proteolysis behaviour. J. Biol. Chem. 262, 8096-8102.

Mayr, E. M., Jaenicke, R., and Glockshuber, R. (1994). Domain interactions and connecting peptides in lens crystallins. J Mol Biol 235, 84-88.

Murzin A. G., Brenner S. E., Hubbard T. and Chothia C. (1995). SCOP: a structural classification of proteins database for the investigation of sequences and structures. J. Mol. Biol. 247, 536-540.

Najmudin, S., Nalini, V., Driessen, H. P., Slingsby, C., Blundell, T., Moss, D., and Lindley, P. (1993). Structure of bovine gB (g II)-crystalline at 1.47 Å. Acta Crystallogr D Biol Crystallogr 49, 223-233.

Norledge, B. V., Mayr, E. M., Glockshuber, R., Bateman, O. A., Slingsby, C., Jaenicke, R., and Driessen, H. P. (1996). The X-ray structures of two mutant crystallin domains shed light on the evolution of multi-domain proteins. Nat Struct Biol 3, 267-274.

Reichlin, M. (1980) Use of glutaraldehyde as a coupling agent for proteins and peptides. Methods Enzymol 70, 159-165.

Richardson, J. S., Richardson, D. C., Tweedy, N. B., Gernert, K. M., Quinn, T. P., Hecht, M. H., Erickson, B. W., Yan, Y., McClain, R. D., Donlan, M. E. and Surles, M. C. (1992): Looking at proteins: representations, folding, packing and design. Biophys. J. 63, 1186-1209.

Riddle, D. S., Santiago, J. V., Bray-Hall, S. T., Doshi, N., Grantcharova, Q. Y and Baker, D. (1997): Functional rapidly folding proteins from simplified amino acid sequences. Nature structural biology 4, 805-809.

Rudolph, R., Siebendritt, R., Nesslauer, G., Sharma, A. K., and Jaenicke, R. (1990). Folding of an all-beta protein: independent domain folding in gamma II-crystallin from calf eye lens. Proc Natl Acad Sci USA 87, 4625-4629.

Sambrook, J., Maniatis, T. and Fritsch, E. F. (1989): Molecular Cloning: A laboratory manual. Cold spring Harbor. Cold Spring Harbour Laboratory Press, New York.

Sharma, A. K., Minke-Gogl, V., Gohl, P., Siebendritt, R., Jaenicke, R., and Rudolph, R. (1990). Limited proteolysis of gamma II-crystallin from calf eye lens. Physicochemical studies on the N-terminal domain and the intact two-domain protein. Eur J Biochem 194, 603-609.

Slingsby, C. (1985): Structural variation in lens crystallins. TIBS 10, 281-284.

Smith, G. P (1985): Filamentous Fusion Phage: Novel expression vectors that display cloned antigens on the virion surface. Science 228, 1315-1317.

Stahl, S, and Uhlen, M. (1997): Bacterial surface display: trends and progress. TIBTECH 15, 185-192.

Takamiya, H., Shimizu, F., and Vogt, A. (1975) A two-stage method for cross-linking antibody globulin to ferritin by glutaraldehyde.III. Size and antibody activity of the conjugates. J Immunol Methods 8(4), 301-306.

Vijay-Kumar, S., Bugg, C. E., and Cook, W. J. (1987). Structure of ubiquitin refined at 1.8 Å resolution. J Mol Biol 194, 531-544.

Voet, D., and Voet, J. G. (1995). Biochemistry, Second Edition edn (New York, John Wiley & Sons, Inc.).

Wistow, G., Turnell, B., Summers, L., Slingsby, C., Moss, D., Miller, L., Lindley, P., and Blundell, T. (1983). X-ray analysis of the eye lens protein gamma-II crystallin at 1.9 A resolution. J Mol Biol 170, 175-202.

Wistow, G. J., and Piatigorsky, J. (1988). Lens crystallins: the evolution and expression of proteins for a highly specialized tissue. Annu Rev Biochem 57, 479-504.

What is claimed is:

1. A conjugate comprising the following components:
one or more polypeptide molecules (I), wherein each polypeptide molecule (I) is a modified mammalian ubiquitin and has a binding property for specific binding to a ligand which is newly generated or altered as compared to the corresponding wildtype mammalian ubiquitin, wherein said binding property which is newly generated or altered compared to wildtype mammalian ubiquitin is based on one or more amino acid substitutions in a surface exposed region of a β sheet of the polypeptide molecule (I), and wherein the one or more amino acid substitutions are of one or more amino acid residues selected from the group consisting of residues corresponding to residues 2, 4, 6, 62, 63, 64, 65, and 66 of the wildtype mammalian ubiquitin, and, covalently linked thereto,
one or more functional component (II) selected from the group consisting of polypeptides and proteins, organic and inorganic polymers, nucleic acids, lipids, sugars, low molecular weight substances, and peptides as well as derivatives of these substances, wherein after coupling of (I) to (II) the functionality of all components is retained.

2. The conjugate according to claim 1 wherein the coupling of (I) to (II) is performed in a region outside of the surface-exposed region of the β sheet of the polypeptide molecule (I) intended for specific binding to a ligand.

3. The conjugate according to claim 2 wherein the coupling of (I) to (II) is performed in a region outside of the β sheet of the polypeptide molecule (I) which has the newly generated or altered binding property for specific binding to a ligand.

4. The conjugate according to claim 1 wherein the coupling of (I) to (II) is performed via amino acid residues of (I).

5. The conjugate according to claim 1 wherein the coupling of (I) to (II) is performed via amino acid residues in an additional terminal peptide fusion to (I).

6. The conjugate according to claim 4 wherein the coupling is performed site-specifically or selectively in an undirected manner via cysteine or lysine side chains in (I).

7. The conjugate according to claim 4 or 6 wherein side chains outside of the binding surface of (I) to the ligand are involved in coupling.

8. The conjugate according to claim 6 wherein the coupling is performed via the lysine residues 29 and 33 of the ubiquitin molecule.

9. The conjugate according to claim 5 wherein the additional terminal peptide fusion to (I) contains one or more cysteine residues or one or more lysine residues wherein these amino acid residues preferably are not involved in the interaction of (I) with the ligand.

10. The conjugate according to claim 1 wherein the functional component (II) is a peptide, polypeptide or a protein, preferably a protein chromophore, an enzyme, an immunoglobulin, an immunoglobulin derivative, a toxin or a polypeptide according to I.

11. The conjugate according to claim 1 wherein the functional component (II) is a polymer, preferably dextrane, polymethacrylate, sepharose, agarose, polyvinyl, polystyrene, silica gel, cellulose or polyethylene glycol, or a polymer derivative.

12. The conjugate according to claim 1 wherein the functional component (II) is a low molecular weight substance, preferably a dye, biotin, digoxigenin, a heavy metal, a chelating agent, a radioisotope, an antibiotic or a cytotoxic substance.

13. The conjugate according to claim 1 wherein polypeptide molecule (I) shows a newly generated or altered binding property for specific binding to a ligand selected from the group consisting of proteins, polypeptides, peptides, low molecular weight substances, lipids, sugars, nucleic acids, organic and inorganic polymers, as well as derivatives of these substances, wherein the polypeptide molecule (I) and the ligand form a complex havin a dissociation constant $K_D$ of $10^{-5}$ M or smaller.

14. The conjugate according to claim 1 wherein polypeptide molecule (I) shows a newly generated or altered binding property for specific binding to a ligand which is a polypeptide or a protein.

15. The conjugate according to claim 1 wherein polypeptide molecule (I) shows a newly generated or altered binding property for specific binding to a ligand which is a peptide.

16. The conjugate according to claim 1 wherein polypeptide molecule (I) shows a newly generated or altered binding property for specific binding to a ligand which is a low molecular weight substance.

17. The conjugate according to claim 1 wherein polypeptide molecule (I) shows a newly generated or altered binding property for specific binding to a ligand which is a lipid or lipid derivative.

18. The conjugate according to claim 1 wherein the component (II) is one or more polypeptides which is identical to (I) and covalently linked thereto whereby an enhancement of the affinity for the ligand of (I) is achieved due to avidity effects.

19. The conjugate according to claim 1 wherein the component (II) is a polypeptide, protein or polymer to which polypeptide molecule (I) is covalently linked several times whereby an enhancement of the affinity for the ligand of (I) is achieved due to avidity effects.

20. The conjugate according to claim 1 wherein the component (II) is a polypeptide or polymer which after covalent linkage to polypeptide molecule (I) undergoes a covalent or non-covalent binding to other conjugates of this type whereby an enhancement of the affinity for the ligand of (I) is achieved due to avidity effects.

21. The conjugate according to claim 14 wherein the ligand is a polypeptide or a protein selected from the group consisting of immunoglobulins and immunoglobulin derivatives, proteins obtained from blood plasma, blood clotting factors and inhibitors, growth factors, interleukins, cytokins, receptor proteins, glycoproteins, viral proteins and cell surface markers.

22. The conjugate according to claim 21 wherein the ligand is selected from CD14, CD25, and CD34.

23. The conjugate according to claim 15 wherein the peptide is an affinity tag, or a peptide of viral origin.

24. The conjugate according to claim 23, wherein the affinity tag is selected from the group consisting of S-Tag, T7-Tag, His-Tag, Strep-Tag, Myc-Tag, and FLAG-Tag.

25. The conjugate according to claim 16 wherein the low molecular weight substance is selected from the group consisting of steroids, cholesterol and noxious substances.

26. The conjugate according to claim 25, wherein the noxious substance is a halogenated hydrocarbon.

27. The conjugate according to claim 17 wherein the lipid or lipid derivative is selected from the group consisting of bacterial lipopolysaccharides, liposomes and lipoproteins.

28. A diagnostic kit containing a conjugate according to claim 1.

29. A pharmaceutical composition comprising a conjugate according to claims 1 and a pharmaceutically acceptable carrier.

30. A composition for affinity enrichment comprising a conjugate according to claim 1 wherein the functional component is a membrane, polymer bead or a chromatographic support material.

31. A conjugate comprising the following components:
one or more polypeptide molecules (I) wherein each polypeptide molecule (I) is encoded by SEQ ID NO: 12 or SEQ ID NO: 13; and covalently linked thereto,
one or more functional component (II) selected from the group consisting of polypeptides and proteins, organic and inorganic polymers, nucleic acids, lipids, sugars, low molecular weight substances, and peptides as well as derivatives of these substances, wherein after coupling of (I) to (II) the functionality of all components is retained.

32. A process for the preparation of a conjugate according to claim 1 starting with polypeptide molecule (I) having a known sequence the process comprising the following steps:
Identification of amino acid residues suitable for coupling by analysis of the spatial structure of the protein, preferably of residues outside of the surface of interaction of (I) with the ligand;
activation of a coupling partner by a suitable coupling reagent;

performing the coupling reaction;

isolation of the conjugate; and detection of the functionality of both components of the conjugate.

33. A process for the preparation of a conjugate according to claim 1 starting with polypeptide molecule (I) having a known sequence wherein no amino acid residues suitable for coupling were identified the process comprising the following steps:

Introduction of amino acid residues suitable for coupling by substitution, insertion or fusion, preferably of residues exposed to the surface outside of the surface of interaction of (I) with the ligand;

detection of the accessibility of the amino acid residues introduced;

detection of the functionality of the polypeptide molecule (I) altered in this manner;

activation of a coupling partner by a suitable coupling reagent;

performing the coupling reaction;

isolation of the conjugate; and detection of the functionality of both components of the conjugate.

34. The conjugate which can be prepared by the process according to claim 32 or 33.

* * * * *

SEQUENCE LISTING

<160> NUMBER OF SEQ ID NOS: 37

<210> SEQ ID NO 1
<211> LENGTH: 534
<212> TYPE: DNA
<213> ORGANISM: Artificial Sequence
<220> FEATURE:
<223> OTHER INFORMATION: Mutated human gamma-II-crystallin library
      constituents
<220> FEATURE:
<221> NAME/KEY: misc_feature
<222> LOCATION: (7)..(8)
<223> OTHER INFORMATION: n is a, c, g, or t
<220> FEATURE:
<221> NAME/KEY: misc_feature
<222> LOCATION: (9)..(9)
<223> OTHER INFORMATION: k is g or t
<220> FEATURE:
<221> NAME/KEY: misc_feature
<222> LOCATION: (13)..(14)
<223> OTHER INFORMATION: n is a, c, g, or t
<220> FEATURE:
<221> NAME/KEY: misc_feature
<222> LOCATION: (15)..(15)
<223> OTHER INFORMATION: k is g or t
<220> FEATURE:
<221> NAME/KEY: misc_feature
<222> LOCATION: (19)..(20)
<223> OTHER INFORMATION: n is a, c, g, or t
<220> FEATURE:
<221> NAME/KEY: misc_feature
<222> LOCATION: (21)..(21)
<223> OTHER INFORMATION: k is g or t
<220> FEATURE:
<221> NAME/KEY: misc_feature
<222> LOCATION: (46)..(47)
<223> OTHER INFORMATION: n is a, c, g, or t
<220> FEATURE:
<221> NAME/KEY: misc_feature
<222> LOCATION: (48)..(48)
<223> OTHER INFORMATION: k is g or t
<220> FEATURE:
<221> NAME/KEY: misc_feature
<222> LOCATION: (52)..(53)
<223> OTHER INFORMATION: n is a, c, g, or t
<220> FEATURE:
<221> NAME/KEY: misc_feature
<222> LOCATION: (54)..(54)
<223> OTHER INFORMATION: k is g or t
<220> FEATURE:
<221> NAME/KEY: misc_feature
<222> LOCATION: (58)..(59)
<223> OTHER INFORMATION: n is a, c, g, or t
<220> FEATURE:
<221> NAME/KEY: misc_feature
<222> LOCATION: (60)..(60)
<223> OTHER INFORMATION: k is g or t
<220> FEATURE:
<221> NAME/KEY: misc_feature
<222> LOCATION: (109)..(110)
<223> OTHER INFORMATION: n is a, c, g, or t
<220> FEATURE:
<221> NAME/KEY: misc_feature
<222> LOCATION: (111)..(111)
<223> OTHER INFORMATION: k is g or t
<220> FEATURE:
<221> NAME/KEY: misc_feature
<222> LOCATION: (115)..(116)
<223> OTHER INFORMATION: n is a, c, g, or t
<220> FEATURE:
<221> NAME/KEY: misc_feature
<222> LOCATION: (117)..(117)
<223> OTHER INFORMATION: k is g or t

<400> SEQUENCE: 1

```
atgggtnnka tcnnkttcnn kgaagaccgt gctttccagg gtcgtnnkta cnnktgcnnk      60
accgactgcc cgaacctgca gccgtacttc tcccgttgca actccatcnn kgttnnktcc     120
ggttgctgga tgatctacga acgtccgaac taccagggtc accgtcacca gtacttcctg    180
cggcgtgggg agtaccccga ctaccagcaa tggatgggcc tcagcgactc catccgctcc    240
tgctgcctca tccccccca ctctggcgct tacagaatga agatctacga cagagatgaa    300
ttgaggggac aaatgtcaga gctcacagac gactgtctct ctgttcagga ccgcttccac   360
ctcactgaaa ttcactccct caatgtgctg gagggcagct ggatcctcta tgagatgccc   420
aactacaggg ggaggcagta tctgctgagg ccggggagt acaggaggtt tcttgattgg    480
ggggctccaa atgccaaagt tggctctctt agacgagtca tggatttgta cgcg          534
```

<210> SEQ ID NO 2
<211> LENGTH: 534
<212> TYPE: DNA
<213> ORGANISM: Artificial Sequence
<220> FEATURE:
<223> OTHER INFORMATION: Artificially synthesized
      gamma-II-crystallin-based Affilin - SPC1-A1

<400> SEQUENCE: 2

```
atgggttta tctggttcat ggaagaccgt gctttccagg gtcgtaggta cgattgcggt      60
accgactgcc cgaacctgca gccgtacttc tcccgttgca actccatcaa ggttaagtcc    120
ggttgctgga tgatctacga acgtccgaac taccagggtc accgtcacca gtacttcctg    180
cggcgtgggg agtaccccga ctaccagcaa tggatgggcc tcagcgactc catccgctcc    240
tgctgcctca tccccccca ctctggcgct tacagaatga agatctacga cagagatgaa    300
ttgaggggac aaatgtcaga gctcacagac gactgtctct ctgttcagga ccgcttccac   360
ctcactgaaa ttcactccct caatgtgctg gagggcagct ggatcctcta tgagatgccc   420
aactacaggg ggaggcagta tctgctgagg ccggggagt acaggaggtt tcttgattgg    480
ggggctccaa atgccaaagt tggctctctt agacgagtca tggatttgta cgcg          534
```

<210> SEQ ID NO 3
<211> LENGTH: 534
<212> TYPE: DNA
<213> ORGANISM: Artificial Sequence
<220> FEATURE:
<223> OTHER INFORMATION: Artificially synthesized
      gamma-II-crystallin-based Affilin - SPC1-A7

<400> SEQUENCE: 3

```
atgggtctga tctgtttctc tgaagaccgt gctttccagg gtcgtaggta catgtgcctg      60
accgactgcc cgaacctgca gccgtacttc tcccgttgca actccatcaa tgtttggtcc    120
ggttgctgga tgatctacga acgtccgaac taccagggtc accgtcacca gtacttcctg    180
cggcgtgggg agtaccccga ctaccagcaa tggatgggcc tcagcgactc catccgctcc    240
tgctgcctca tccccccca ctctggcgct tacagaatga agatctacga cagagatgaa    300
ttgaggggac aaatgtcaga gctcacagac gactgtctct ctgttcagga ccgcttccac   360
ctcactgaaa ttcactccct caatgtgctg gagggcagct ggatcctcta tgagatgccc   420
aactacaggg ggaggcagta tctgctgagg ccggggagt acaggaggtt tcttgattgg    480
ggggctccaa atgccaaagt tggctctctt agacgagtca tggatttgta cgcg          534
```

<210> SEQ ID NO 4
<211> LENGTH: 534
<212> TYPE: DNA
<213> ORGANISM: Artificial Sequence
<220> FEATURE:
<223> OTHER INFORMATION: Artifically synthesized
    amma-II-crystallin-based Affilin - SPC1-G3

<400> SEQUENCE: 4

```
atgggttcta tcattttcct tgaagaccgt gctttccagg gtcgtattta cggttgcact    60
accgactgcc cgaacctgca gccgtacttc tcccgttgca actccatcgt ggttcagtcc   120
ggttgctgga tgatctacga acgtccgaac taccagggtc accgtcacca gtacttcctg   180
cggcgtgggg agtaccccga ctaccagcaa tggatgggcc tcagcgactc catccgctcc   240
tgctgcctca tcccccccca ctctggcgct tacagaatga agatctacga cagagatgaa   300
ttgaggggac aaatgtcaga gctcacagac gactgtctct ctgttcagga ccgcttccac   360
ctcactgaaa ttcactccct caatgtgctg gagggcagct ggatcctcta tgagatgccc   420
aactacaggg ggaggcagta tctgctgagg ccggggagt acaggaggtt tcttgattgg   480
ggggctccaa atgccaaagt tggctctctt agacgagtca tggatttgta cgcg         534
```

<210> SEQ ID NO 5
<211> LENGTH: 549
<212> TYPE: DNA
<213> ORGANISM: Artificial Sequence
<220> FEATURE:
<223> OTHER INFORMATION: Artifically synthesized
    gamma-II-crystallin-based Affilin - SPC1-A7BB

<400> SEQUENCE: 5

```
atgggtctga tctctttctc tgaagaccgt gctttccagg gtcgtaggta catgtgcctg    60
accgactgcc cgaacctgca gccgtacttc tcccgttgca actccatcaa tgtttggtcc   120
ggttgctgga tgatctacga acgtccgaac taccagggtc accagtactt cctgcggcgt   180
ggggagtacc ccgactacca gcaatggatg ggcctcagcg actccatccg ctcctgctgc   240
ctcatccccc ccactctgg cgcttacaga atgaagatct acgacagaga tgaattgagg   300
gacaaatgt cagagctcac agacgactgt ctctctgttc aggaccgctt ccacctcact   360
gaaattcact ccctcaatgt gctggagggc agctggatcc tctatgagat gcccaactac   420
agggggaggc agtatctgct gaggccgggg gagtacagga ggtttcttga ttgggggct   480
ccaaatgcca agttggctc tcttagacga gtcatggatt tgtacctcga gcaccaccac   540
caccaccac                                                           549
```

<210> SEQ ID NO 6
<211> LENGTH: 570
<212> TYPE: DNA
<213> ORGANISM: Artificial Sequence
<220> FEATURE:
<223> OTHER INFORMATION: Artifically synthesized
    gamma-II-crystallin-based Affilin - SPC1-A7JJ

<400> SEQUENCE: 6

```
atgggtctga tctctttctc tgaagaccgt gctttccagg gtcgtaggta catgtgcctg    60
accgactgcc cgaacctgca gccgtacttc tcccgttgca actccatcaa tgtttggtcc   120
ggttgctgga tgatctacga acgtccgaac taccagggtc accagtactt cctgcggcgt   180
ggggagtacc ccgactacca gcaatggatg ggcctcagcg actccatccg ctcctgctgc   240
ctcatccccc ccactctgg cgcttacaga atgaagatct acgacagaga tgaattgagg   300
```

-continued

```
ggacaaatgt cagagctcac agacgactgt ctctctgttc aggaccgctt ccacctcact    360
gaaattcact ccctcaatgt gctggagggc agctggatcc tctatgagat gcccaactac    420
aggggagggc agtatctgct gaggccgggg gagtacagga ggtttcttga ttggggggct    480
ccaaatgcca aagttggctc tcttagacga gtcatggatt tgtacctcga gtgcggcggc    540
catcaccatc accaccacca ccaccaccac                                     570
```

<210> SEQ ID NO 7
<211> LENGTH: 588
<212> TYPE: DNA
<213> ORGANISM: Artificial Sequence
<220> FEATURE:
<223> OTHER INFORMATION: Artificially synthesized
      gamma-II-crystallin-based Affilin - SPC1-A7-Cys

<400> SEQUENCE: 7

```
atgggtctga tctctttctc tgaagaccgt gctttccagg gtcgtaggta catgtgcctg     60
accgactgcc cgaacctgca gccgtacttc tcccgttgca actccatcaa tgtttggtcc    120
ggttgctgga tgatctacga acgtccgaac taccagggtc accagtactt cctgcgcgcgt   180 ggggagtacc ccgactacca gcaatggatg ggcctcagcg actccatccg ctcctgctgc    240
ctcatccccc cccactctgg cgcttacaga atgaagatct acgacagaga tgaattgagg    300
ggacaaatgt cagagctcac agacgactgt ctctctgttc aggaccgctt ccacctcact    360
gaaattcact ccctcaatgt gctggagggc agctggatcc tctatgagat gcccaactac    420
aggggagggc agtatctgct gaggccgggg gagtacagga ggtttcttga ttggggggct    480
ccaaatgcca aagttggctc tcttagacga gtcatggatt tgtacctcga gtccggcggc    540
ggggggggag gatcttgcca tcaccatcac caccaccacc accaccac                 588
```

<210> SEQ ID NO 8
<211> LENGTH: 549
<212> TYPE: DNA
<213> ORGANISM: Artificial Sequence
<220> FEATURE:
<223> OTHER INFORMATION: Artificially synthesized
      gamma-II-crystallin-based Affilin - SPC7-E9

<400> SEQUENCE: 8

```
atgggttttta tctgtttctt ggaagaccgt gctttccagg gtcgttctta cgcttgcgat     60
actgactgcc cgaacctgca gccgtacttc tcccgttgca actccatcag tgttctgtcc    120
ggttgctgga tgatctacga acgtccgaac taccagggtc accagtactt cctgcggcgt   180
ggggagtacc ccgactacca gcaatggatg ggcctcagcg actccatccg ctcctgctgc    240
ctcatccccc cccactctgg cgcttacaga atgaagatct acgacagaga tgaattgagg    300
ggacaaatgt cagagctcac agacgactgt ctctctgttc aggaccgctt ccacctcact    360
gaaattcact ccctcaatgt gctggagggc agctggatcc tctatgagat gcccaactac    420
aggggagggc agtatctgct gaggccgggg gagtacagga ggtttcttga ttggggggct    480
ccaaatgcca aagttggctc tcttagacga gtcatggatt tgtacctcga gcaccaccac    540
caccaccac                                                           549
```

<210> SEQ ID NO 9
<211> LENGTH: 228
<212> TYPE: DNA
<213> ORGANISM: Artificial Sequence -continued

```
<220> FEATURE:
<223> OTHER INFORMATION: Artificially synthesized human ubiquitin
      library - wild type ubiquitin

<400> SEQUENCE: 9
atgcagatct tcgtgaagac cctgaccggc aagaccatca ctctggaggt ggagcccagt      60
gacaccatcg aaaatgtgaa ggccaagatc caagataaag aaggcattcc ccccgaccag     120
cagaggctca tctttgcagg caagcagctg aagatggcc gcactctttc tgactacaac      180
atccagaaag agtcgaccct gcacctggtc ctccgcctga ggggcggc                  228

<210> SEQ ID NO 10
<211> LENGTH: 225
<212> TYPE: DNA
<213> ORGANISM: Artificial Sequence
<220> FEATURE:
<223> OTHER INFORMATION: Artificially synthesized modified ubiquitin

<400> SEQUENCE: 10
atgcaaatct tcgttaaaac cctgacggga aagactatca ccctggaggt agaaccgtcc      60
gacaccatcg aaaatgtcaa agctaaaatc caagacaaag aaggaattcc acctgaccag     120
caacgcctag ctttcgcagg acgacaacta gaggacgggc tcaccctgtc tgactacaac     180
atccaaaaag aatccaccct ccacctggca ctcctcctgc gggcc                     225

<210> SEQ ID NO 11
<211> LENGTH: 225
<212> TYPE: DNA
<213> ORGANISM: Artificial Sequence
<220> FEATURE:
<223> OTHER INFORMATION: Mutated UB10 ubiquin library constituents
<220> FEATURE:
<221> NAME/KEY: misc_feature
<222> LOCATION: (4)..(5)
<223> OTHER INFORMATION: n is a, c, g, or t
<220> FEATURE:
<221> NAME/KEY: misc_feature
<222> LOCATION: (6)..(6)
<223> OTHER INFORMATION: k is g or t
<220> FEATURE:
<221> NAME/KEY: misc_feature
<222> LOCATION: (10)..(11)
<223> OTHER INFORMATION: n is a, c, g, or t
<220> FEATURE:
<221> NAME/KEY: misc_feature
<222> LOCATION: (12)..(12)
<223> OTHER INFORMATION: k is g or t
<220> FEATURE:
<221> NAME/KEY: misc_feature
<222> LOCATION: (16)..(17)
<223> OTHER INFORMATION: n is a, c, g, or t
<220> FEATURE:
<221> NAME/KEY: misc_feature
<222> LOCATION: (18)..(18)
<223> OTHER INFORMATION: k is g or t
<220> FEATURE:
<221> NAME/KEY: misc_feature
<222> LOCATION: (184)..(185)
<223> OTHER INFORMATION: n is a, c, g, or t
<220> FEATURE:
<221> NAME/KEY: misc_feature
<222> LOCATION: (186)..(186)
<223> OTHER INFORMATION: k is g or t
<220> FEATURE:
<221> NAME/KEY: misc_feature
<222> LOCATION: (187)..(188)
<223> OTHER INFORMATION: n is a, c, g, or t
<220> FEATURE:
<221> NAME/KEY: misc_feature
<222> LOCATION: (189)..(189)
<223> OTHER INFORMATION: k is g or t
```

```
<220> FEATURE:
<221> NAME/KEY: misc_feature
<222> LOCATION: (190)..(191)
<223> OTHER INFORMATION: n is a, c, g, or t
<220> FEATURE:
<221> NAME/KEY: misc_feature
<222> LOCATION: (192)..(192)
<223> OTHER INFORMATION: k is g or t
<220> FEATURE:
<221> NAME/KEY: misc_feature
<222> LOCATION: (193)..(194)
<223> OTHER INFORMATION: n is a, c, g, or t
<220> FEATURE:
<221> NAME/KEY: misc_feature
<222> LOCATION: (195)..(195)
<223> OTHER INFORMATION: k is g or t
<220> FEATURE:
<221> NAME/KEY: misc_feature
<222> LOCATION: (196)..(197)
<223> OTHER INFORMATION: n is a, c, g, or t
<220> FEATURE:
<221> NAME/KEY: misc_feature
<222> LOCATION: (198)..(198)
<223> OTHER INFORMATION: k is g or t

<400> SEQUENCE: 11
atgnnkatcn nkgttnnkac cctgacggga aagactatca ccctggaggt agaaccgtcc      60
gacaccatcg aaaatgtcaa agctaaaatc caagacaaag aaggaattcc acctgaccag     120
caacgcctag ctttcgcagg acgacaacta gaggacgggc tcaccctgtc tgactacaac     180
atcnnknnkn nknnknnkct ccacctggca ctcctcctgc gggcc                     225

<210> SEQ ID NO 12
<211> LENGTH: 249
<212> TYPE: DNA
<213> ORGANISM: Artificial Sequence
<220> FEATURE:
<223> OTHER INFORMATION: Artificially synthesized ubiquitin-based
      Affilin - SPU11-3-A1

<400> SEQUENCE: 12
atgcggatcc gtgttgctac cctgacggga aagactatca ccctggaggt agaaccgtcc      60
gacaccatcg aaaatgtcaa agctaaaatc caagacaaag aaggaattcc acctgaccag     120
caacgcctag ctttcgcagg acgacaacta gaggacgggc tcaccctgtc tgactacgac     180
atccgtcatg gtacgtcgct ccacctggca ctcctcctgc gggccctcga gcaccaccac     240
caccaccac                                                             249

<210> SEQ ID NO 13
<211> LENGTH: 288
<212> TYPE: DNA
<213> ORGANISM: Artificial Sequence
<220> FEATURE:
<223> OTHER INFORMATION: Artificially synthesized ubiquitin-based
      Affilin - APU11-3-A1_Cys

<400> SEQUENCE: 13
atgcggatcc gtgttgctac cctgacggga aagactatca ccctggaggt agaaccgtcc      60
gacaccatcg aaaatgtcaa agctaaaatc caagacaaag aaggaattcc acctgaccag     120
caacgcctag ctttcgcagg acgacaacta gaggacgggc tcaccctgtc tgactacgac     180
atccgtcatg gtacgtcgct ccacctggca ctcctcctgc gggccctcga gtccggcggc     240 gggggggag gatcttgcca tcaccatcac caccaccacc accaccac                   288
```

```
<210> SEQ ID NO 14
<211> LENGTH: 26
<212> TYPE: DNA
<213> ORGANISM: Artificial Sequence
<220> FEATURE:
<223> OTHER INFORMATION: Artificially synthesized oligonucleotide primer

<400> SEQUENCE: 14
ccatgattac gccaagcttt ggagcc                                          26

<210> SEQ ID NO 15
<211> LENGTH: 31
<212> TYPE: DNA
<213> ORGANISM: Artificial Sequence
<220> FEATURE:
<223> OTHER INFORMATION: Artificially synthesized oligonucleotide primer

<400> SEQUENCE: 15
ccatgggtct gatctctttc tctgaagacc g                                    31

<210> SEQ ID NO 16
<211> LENGTH: 31
<212> TYPE: DNA
<213> ORGANISM: Artificial Sequence
<220> FEATURE:
<223> OTHER INFORMATION: Artificially synthesized oligonucleotide primer

<400> SEQUENCE: 16
cggtcttcag agaaagagat cagacccatg g                                    31

<210> SEQ ID NO 17
<211> LENGTH: 23
<212> TYPE: DNA
<213> ORGANISM: Artificial Sequence
<220> FEATURE:
<223> OTHER INFORMATION: Artificially synthesized oligonucleotide primer

<400> SEQUENCE: 17
gctagttatt gctcagcggt ggc                                             23

<210> SEQ ID NO 18
<211> LENGTH: 66
<212> TYPE: DNA
<213> ORGANISM: Artificial Sequence
<220> FEATURE:
<223> OTHER INFORMATION: Artificially synthesized oligonucleotide primer

<400> SEQUENCE: 18
ggatttgtac ctcgagtgcg gcggccatca ccatcaccac caccaccacc accactgaga     60
tccggc                                                                66

<210> SEQ ID NO 19
<211> LENGTH: 66
<212> TYPE: DNA
<213> ORGANISM: Artificial Sequence
<220> FEATURE:
<223> OTHER INFORMATION: Artificially synthesized oligonucleotide primer

<400> SEQUENCE: 19
gccggatctc agtggtggtg gtggtggtgg tgatggtgat ggccgccgca ctcgaggtac     60
aaatcc                                                                66
```

<210> SEQ ID NO 20
<211> LENGTH: 32
<212> TYPE: DNA
<213> ORGANISM: Artificial Sequence
<220> FEATURE:
<223> OTHER INFORMATION: Artificially synthesized oligonucleotide primer

<400> SEQUENCE: 20
ggatttgtac ctcgagtccg gcggccatca cc            32

<210> SEQ ID NO 21
<211> LENGTH: 32
<212> TYPE: DNA
<213> ORGANISM: Artificial Sequence
<220> FEATURE:
<223> OTHER INFORMATION: Artificially synthesized oligonucleotide primer

<400> SEQUENCE: 21
ggtgatggcc gccggactcg aggtacaaat cc            32

<210> SEQ ID NO 22
<211> LENGTH: 32
<212> TYPE: DNA
<213> ORGANISM: Artificial Sequence
<220> FEATURE:
<223> OTHER INFORMATION: Artificially synthesized oligonucleotide primer

<400> SEQUENCE: 22
ggtgatggcc gccggactcg aggtacaaat cc            32

<210> SEQ ID NO 23
<211> LENGTH: 54
<212> TYPE: DNA
<213> ORGANISM: Artificial Sequence
<220> FEATURE:
<223> OTHER INFORMATION: Artificially synthesized oligonucleotide primer

<400> SEQUENCE: 23
gggggaagct tttatcagtg gtggtggtgg tggtggtgat ggtgatggca agat        54

<210> SEQ ID NO 24
<211> LENGTH: 35
<212> TYPE: DNA
<213> ORGANISM: Artificial Sequence
<220> FEATURE:
<223> OTHER INFORMATION: Artificially synthesized oligonucleotide primer

<400> SEQUENCE: 24
ggagatatac aatatgggtc tgatctcttt ctctg          35

<210> SEQ ID NO 25
<211> LENGTH: 291
<212> TYPE: DNA
<213> ORGANISM: Artificial Sequence
<220> FEATURE:
<223> OTHER INFORMATION: Artificially synthesized sequence of a modified
      ubiquitin protein scaffold

<400> SEQUENCE: 25
atgaaatacc tattgcctac ggcagccgct ggattgttat tactcgcggc ccagccggcc        60
atggccatgc aaatcttcgt taaaaccctg acgggaaaga ctatcaccct ggaggtagaa       120
ccgtccgaca ccatcgaaaa tgtcaaagct aaaatccaag acaaagaagg aattccacct       180
gaccagcaac gcctagcttt cgcaggacga caactagagg acgggctcac cctgtctgac       240
tacaacatcc aaaaagaatc caccctccac ctggcactcc tcctgcgggc c                291

<210> SEQ ID NO 26
<211> LENGTH: 50
<212> TYPE: DNA
<213> ORGANISM: Artificial Sequence
<220> FEATURE:
<223> OTHER INFORMATION: Artificially synthesized oligonucleotide
      template

<400> SEQUENCE: 26
atgcaaatct tcgttaaaac cctgacggga aagactatca ccctggaggt        50

<210> SEQ ID NO 27
<211> LENGTH: 53
<212> TYPE: DNA
<213> ORGANISM: Artificial Sequence
<220> FEATURE:
<223> OTHER INFORMATION: Artificially synthesized oligonucleotide
      template

<400> SEQUENCE: 27
ggattttagc tttgacattt tcgatggtgt cggacggttc tacctccagg gtg     53

<210> SEQ ID NO 28
<211> LENGTH: 53
<212> TYPE: DNA
<213> ORGANISM: Artificial Sequence
<220> FEATURE:
<223> OTHER INFORMATION: Artificially synthesized oligonucleotide
      template

<400> SEQUENCE: 28
gtcaaagcta aatccaaga caaagaagga attccacctg accagcaacg cct      53

<210> SEQ ID NO 29
<211> LENGTH: 50
<212> TYPE: DNA
<213> ORGANISM: Artificial Sequence
<220> FEATURE:
<223> OTHER INFORMATION: Artificially synthesized oligonucleotide
      template

<400> SEQUENCE: 29
gggtgagccc gtcctctagt tgtcgtcctg cgaaagctag gcgttgctgg        50

<210> SEQ ID NO 30
<211> LENGTH: 50
<212> TYPE: DNA
<213> ORGANISM: Artificial Sequence
<220> FEATURE:
<223> OTHER INFORMATION: Artificially synthesized oligonucleotide
      template

<400> SEQUENCE: 30
gacgggctca ccctgtctga ctacaacatc caaaagaat ccaccctcca         50

<210> SEQ ID NO 31
<211> LENGTH: 39
<212> TYPE: DNA
<213> ORGANISM: Artificial Sequence
<220> FEATURE:
<223> OTHER INFORMATION: Artificially synthesized oligonucleotide
      template

<400> SEQUENCE: 31
gagtgctcgc agcaggagtg ccaggtggag ggtggattc                    39

<210> SEQ ID NO 32
<211> LENGTH: 22
<212> TYPE: DNA
<213> ORGANISM: Artificial Sequence
<220> FEATURE:
<223> OTHER INFORMATION: Artificially synthesized oligonucleotide primer

<400> SEQUENCE: 32
gatatacata tgcaaatctt cg                                          22

<210> SEQ ID NO 33
<211> LENGTH: 18
<212> TYPE: DNA
<213> ORGANISM: Artificial Sequence
<220> FEATURE:
<223> OTHER INFORMATION: Artificially synthesized oligonucleotide primer

<400> SEQUENCE: 33
gtggtgctcg agtgctcg                                               18

<210> SEQ ID NO 34
<211> LENGTH: 55
<212> TYPE: DNA
<213> ORGANISM: Artificial Sequence
<220> FEATURE:
<223> OTHER INFORMATION: Artificially synthesized degenerate
      oligonucleotide primer
<220> FEATURE:
<221> NAME/KEY: misc_feature
<222> LOCATION: (20)..(21)
<223> OTHER INFORMATION: n is a, c, g, or t
<220> FEATURE:
<221> NAME/KEY: misc_feature
<222> LOCATION: (22)..(22)
<223> OTHER INFORMATION: k is g or t
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (28)..(28)
<223> OTHER INFORMATION: k is g or t
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (34)..(34)
<223> OTHER INFORMATION: k is g or t

<400> SEQUENCE: 34
ccagccggcc atggccatgn nkatcnnkgt tnnkaccctg acgggaaaga ctatc       55

<210> SEQ ID NO 35
<211> LENGTH: 55
<212> TYPE: DNA
<213> ORGANISM: Artificial Sequence
<220> FEATURE:
<223> OTHER INFORMATION: Artificially synthesized degenerate
      oligonucleotide primer
<220> FEATURE:
<221> NAME/KEY: misc_feature
<222> LOCATION: (22)..(22)
<223> OTHER INFORMATION: m is a or c
<220> FEATURE:
<221> NAME/KEY: misc_feature
<222> LOCATION: (23)..(24)
<223> OTHER INFORMATION: n is a, c, g, or t

```
<220> FEATURE:
<221> NAME/KEY: misc_feature
<222> LOCATION: (25)..(25)
<223> OTHER INFORMATION: m is a or c
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (28)..(28)
<223> OTHER INFORMATION: m is a or c
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: misc_feature
<222> LOCATION: (31)..(31)
<223> OTHER INFORMATION: m is a or c
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (34)..(34)
<223> OTHER INFORMATION: m is a or c
<220> FEATURE:
<221> NAME/KEY: misc_feature
<222> LOCATION: (35)..(36)
<223> OTHER INFORMATION: n is a, c, g, or t

<400> SEQUENCE: 35
caggaggagt gccaggtgga gmnnmnnmnn mnnmnngatg ttgtagtcag acagg          55

<210> SEQ ID NO 36
<211> LENGTH: 34
<212> TYPE: DNA
<213> ORGANISM: Artificial Sequence
<220> FEATURE:
<223> OTHER INFORMATION: Artificially synthesized oligonucleotide primer

<400> SEQUENCE: 36
gttattactc gcggcccagc cggccatggc catg                                 34

<210> SEQ ID NO 37
<211> LENGTH: 48
<212> TYPE: DNA
<213> ORGANISM: Artificial Sequence
<220> FEATURE:
<223> OTHER INFORMATION: Artificially synthesized oligonucleotide primer

<400> SEQUENCE: 37 gagttttgt tcggcctcga gggcccgcag gaggagtgcc aggtggag                   48
```